(12) United States Patent
Komoriya et al.

(10) Patent No.: US 9,204,652 B2
(45) Date of Patent: Dec. 8, 2015

(54) ANTIBACTERIAL AGENT, SUBSTRATE SURFACE TREATMENT METHOD USING THE SAME, ANTIBACTERIAL AGENT COMPOSITION, AND SUBSTRATE SURFACE TREATMENT METHOD USING THE SAME

(75) Inventors: Haruhiko Komoriya, Iruma-gun (JP); Katsutoshi Suzuki, Hino (JP); Toru Tanaka, Fujimino (JP); Takamasa Kitamoto, Asaka (JP); Masayuki Shiota, Ube (JP); Ryoko Shimada, Hiratsuka (JP); Kazuki Tanaka, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 200 days.

(21) Appl. No.: 13/876,406

(22) PCT Filed: Sep. 28, 2011

(86) PCT No.: PCT/JP2011/072166
§ 371 (c)(1),
(2), (4) Date: Mar. 27, 2013

(87) PCT Pub. No.: WO2012/043619
PCT Pub. Date: Apr. 5, 2012

(65) Prior Publication Data
US 2013/0189220 A1 Jul. 25, 2013

(30) Foreign Application Priority Data

Sep. 28, 2010 (JP) .................. 2010-216979
Sep. 28, 2010 (JP) .................. 2010-216980
Sep. 26, 2011 (JP) .................. 2011-208994
Sep. 26, 2011 (JP) .................. 2011-208995

(51) Int. Cl.
| | |
|---|---|
| A01N 55/00 | (2006.01) |
| A01N 41/10 | (2006.01) |
| A01N 47/02 | (2006.01) |
| C08F 12/30 | (2006.01) |
| C08F 20/38 | (2006.01) |
| C09D 5/14 | (2006.01) |
| C08F 220/38 | (2006.01) |

(52) U.S. Cl.
CPC ............ *A01N 55/00* (2013.01); *A01N 41/10* (2013.01); *A01N 47/02* (2013.01); *C08F 12/30* (2013.01); *C08F 20/38* (2013.01); *C09D 5/14* (2013.01); *C08F 2220/382* (2013.01)

(58) Field of Classification Search
CPC ....... A01N 41/10; A01N 47/02; A01N 55/00; C08F 12/30; C08F 20/38; C08F 2220/382; C09D 5/14

USPC ............ 424/405, 409, 485, 486, 78.17; 510/199, 243, 244, 382, 466; 514/506, 514/550, 706, 709, 711, 715, 759, 772.1; 562/101, 102, 108, 109, 111, 113
See application file for complete search history.

(56) References Cited

U.S. PATENT DOCUMENTS

| | | | |
|---|---|---|---|
| 3,758,591 A | * | 9/1973 | Koshar ............... 568/30 |
| 7,781,085 B2 | * | 8/2010 | Sugiyama ............ 429/494 |
| 8,822,588 B2 | * | 9/2014 | Terui et al. .......... 524/544 |
| 2011/0065857 A1 | | 3/2011 | Terui et al. |
| 2011/0070544 A1 | | 3/2011 | Nagamori et al. |

FOREIGN PATENT DOCUMENTS

| | | |
|---|---|---|
| JP | 9-136808 A | 5/1997 |
| JP | 2001-55458 A | 2/2001 |
| JP | 2008-214396 A | 9/2008 |
| JP | 2009-242391 A | 10/2009 |
| JP | 2010-18785 A | 1/2010 |
| JP | 2010-53257 A | 3/2010 |

OTHER PUBLICATIONS

International Search Report with English translation dated Dec. 20, 2011 (four (4) pages).
Japanese Industrial Standard (JIS) Z 2801 (2006) (twenty-six (26) pages).
Japanese Industrial Standard (JIS) Z 2911 (2000) (fifty (50) pages).

* cited by examiner

*Primary Examiner* — Jane C Oswecki
(74) *Attorney, Agent, or Firm* — Crowell & Moring LLP

(57) ABSTRACT

[Problem] To provide an antibacterial agent which can be limited to the required location on the surface of a material without mixing and has excellent antibacterial, antifungal and antiviral effects even at low concentrations of the active component without elution or volatilization.
[Solution] An antibacterial agent that contains as an active component a resin having an organic group represented by general formula (I-1).

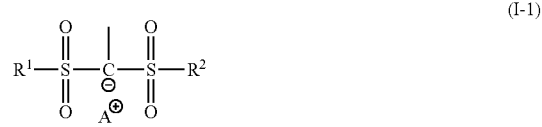

(I-1)

(In the formula (I-1), $R^1$ and $R^2$ mutually independently represent a $C_1$-$C_4$ fluoroalkyl group. "C" and "A" are bonded to each other through a covalent bond or an ionic bond, and "A" represents a hydrogen atom or a cation.)

30 Claims, No Drawings

ANTIBACTERIAL AGENT, SUBSTRATE SURFACE TREATMENT METHOD USING THE SAME, ANTIBACTERIAL AGENT COMPOSITION, AND SUBSTRATE SURFACE TREATMENT METHOD USING THE SAME

TECHNICAL FIELD

The present invention relates to an antibacterial agent having antibacterial, antifungal and antiviral properties, a substrate surface treatment method using the same and its antibacterial member, and additionally to an antibacterial agent composition and a substrate surface treatment method using the same.

BACKGROUND OF THE INVENTION

Needs for antibacterial agents are on its way to growing widely, together with the diversification of life environment and a change in awareness of life. At present, antibacterial and antifungal chemical techniques are applied not only to a field related to people's lives but also to every industrial field such as the plastic industry, the electronic component industry and the like.

An antibacterial technique of the present invention is a series of techniques of persistently preventing the generation and growth of microorganisms (bacteria and fungi in particular) so as to previously prevent or avoid damage caused thereby.

For provisional sterilization, there are various physical techniques such as a method using ultraviolet rays or radiation, a heating method, a cooling method, a pressurizing method and the like. On the contrary to the provisional sterilization, an antibacterial technique is one that keeps a level of not more than sterilization and not less than bacteriostasis for a long period of time thereby suppressing the multiplication of microorganisms persistently. Incidentally, "sterilization" means a level at which microorganisms become extinct, while "bacteriostasis" means a level at which the multiplication of the microorganisms is suppressed.

Bacteria on which an antibacterial agent exhibits antibacterial activity are exemplified by gram-positive bacteria and gram-negative bacteria. Gram-positive bacteria are exemplified by pathogens such as *Staphylococcus aureus, Streptococcus pyogenes* and *Clostridium botulinum*. On the other hand, gram-negative bacteria are exemplified by pathogens such as *Salmonella, Escherichia coli, Klebsiella pneumoniae, Haemophilus, Pseudomonas aeruginosa* and *Proteus*. Meanwhile, fungi include ones parasitic on humans to bring about diseases, such as Trichophytons.

Thus, antibacterial agents are widely applied in order to persistently suppress the multiplication of microorganisms.

Additionally, antibacterial agents are also required to have both antifungal properties and antiviral properties, for example, virus disinfection and the like.

In human life spaces, there exist a variety of fungi and viruses.

Principal kinds of fungi are exemplified by blue mold, green mold, *Mucor* and *Rhizopus*. Though one popularly known as black mold can also be cited, it is difficult to specify the kind of fungi. In addition, in Europe, *Neurospora crassa* is also popularly known and stains on walls are often *Cladosporium*.

On the other hand, principal kinds of viruses can be exemplified by Norovirus, Rotavirus, Rhinovirus, Coronavirus and respiratory syncytial virus. Viruses are classified into those having envelope and those not having envelope. Viruses having envelope are highly sensitive to a bactericidal agent effective against bacteria, while viruses not having envelope are highly resistant to the same. Of major viruses not having envelope, an RNA virus is exemplified by enterovirus such as poliovirus and Reoviridae, while a DNA virus is exemplified by adenovirus, papovavirus, the hepatitis B virus and the like. Enterovirus such as poliovirus, Coxsackievirus, echovirus and the like, i.e., RNA viruses not having envelope generally have strong resistance to various bactericidal agents, followed by adenovirus; on the contrary, viruses having envelope such as herpesvirus, Vaccinia virus and influenza virus are highly sensitive to the same. Among liquid chemicals, sodium hypochlorite is said to be the most effective bactericidal agent against any virus, even in a relatively low concentration.

Additionally, antibacterial agents are wide-ranging in kind so as to be variously used according to purposes. Antibacterial agents can roughly be classified into organic compound-based ones, inorganic compound-based ones and natural product-based ones.

Organic compound-based antibacterial agents are known to include: heterocyclic compounds such as thiazoles, imidazoles, pyridines, triazine and the like: organic nitrogen compounds such as amine, quaternary ammonium compounds, nitrile compounds and the like; organic oxygen compounds such as phenol, cresol, halogenated phenols and the like; organic sulfur compounds such as thiol and the like; and organic phosphorous compounds such as thiophosphoric acid and the like. The organic compound-based antibacterial agents are characterized by having an excellent antibacterial property against fungi. However, in the case where these are added to a film or a resinous molded article, there may arise volatilization or elusion, in which the effect becomes difficult to be kept. Moreover, since not a few of the organic compound-based antibacterial agents have toxicity, the use of them is sometimes restricted particularly in the fields of food, food processing and packaging from the viewpoint of consumer protection.

On the other hand, natural product-based antibacterial agents represented by chili extract, chitin, chitosan, wasabi extract, mustard extract, tea extract and hinokitiol are know. The natural product-based antibacterial agents are sometimes preferably used in view of safety, though there are problems of elusion and volatilization as in organic compound-based ones.

Moreover, inorganic compound-based antibacterial agents represented by silver are known, and these attain high levels of performance in the uses for resinous molded articles, films, fibers and the like. Inorganic compound-based antibacterial agents have difficulty in causing elusion or volatilization and tend to maintain the antibacterial effect for a long period of time and excellent in safety, which serves as the advantage of the inorganic compound-based antibacterial agents. However, in the case of attempting to disperse particles of Ag or Ag-loaded zeolite or the like in a resin, it is difficult to disperse the particles evenly and an antibacterial agent disposed inside is hard to act on outside fungi; therefore, the concentration of the added antibacterial agent is required to be increased in order to obtain a desired antibacterial effect. Hence it is indicated that the antibacterial effect (the antifungal effect in particular) is inferior to that in the organic compound-based ones. Furthermore, the use of expensive silver limits the applicable fields, which is indicated as a problem.

Against the above-mentioned background, attempts to fix a compound group having antibacterial property in a resin have been made and disclosed by two or more prior art references.

For example, in Patent Publication 1, a polymer-bonded antibacterial agent is disclosed as a polymer bonded to 2,2,6,6-tetramethyl-4-piperidine thereby suppressing elusion and volatilization.

Additionally, Patent Publication 2 discloses an antibacterial resin film which comprises a polyamide-based resin having a phosphonium sulfonate group, in which it is said that the antibacterial resin film has both antibacterial property and practical durability.

The polymer-bonded antibacterial agent disclosed by Patent Publication 1 and the antibacterial resin film disclosed by Patent Publication 2 both succeeded in bonding a compound group that has antibacterial property to a resin to fix it.

Patent Publication 3 discloses an antimicrobial resin characterized in that a polymer having carboxyl groups is provided such that a part of the carboxyl groups link to silver while the carboxyl groups bond to polyvalent metallic ion to form cross-linking bonds, in which it is said that the antibacterial property attained by virtue of silver ion is exhibited for a long period of time.

Furthermore, an antistatic agent having a bismethide acid group is disclosed in Patent Publication 4.

REFERENCES ABOUT PRIOR ART

Patent Publication

Patent Publication 1: Japanese Patent Application Publication No. 2008-214396
Patent Publication 2: Japanese Patent Application Publication No. 2001-55458
Patent Publication 3: Japanese Patent Application Publication No. 9-136808
Patent Publication 4: Japanese Patent Application Publication No. 2010-018785

SUMMARY OF THE INVENTION

Problems to be Solved by the Invention

Although the polymer-bonded antibacterial agent disclosed by Patent Publication 1 and the antibacterial resin film disclosed by Patent Publication 2 both succeeded in bonding a compound group that has antibacterial property to a resin to fix it, there lies a problem that the antibacterial property is inferior to the case where the compound group that has antibacterial property is merely mixed and therefore not fixed.

On an inorganic antibacterial agent, an attempt to evenly disperse the antibacterial agent in a resin has been made. For example, in the antimicrobial resin of Patent Publication 3, a polymer having carboxyl groups is provided such that a part of the carboxyl groups link to silver while the carboxyl groups bond to polyvalent metallic ion to form cross-linking bonds, in which the antibacterial property attained by virtue of silver ion seems to be exhibited for a long period of time. However, the antimicrobial resin of Patent Publication 3 is not such a one as to contain an antibacterial organic group in the chemical structure of a resin.

Additionally, conventional antibacterial resins have involved a problem that a long-term antibacterial effect is difficult to be obtained in the case of using an organic compound-based or a natural product-based one due to elusion, volatilization or the like.

Meanwhile, in the case of using an inorganic compound-based antibacterial agent (e.g., silver) the heat resistant temperature is so high that an operation such as kneading it into a resin and the like is practicable. However, the antibacterial effect is not sufficiently obtained particularly in antifungal property, and additionally the added antibacterial agent is difficult to be limitedly stationed at a required site of a material surface or the like which requires the antifungal property. As a result, an excessively large amount of the antibacterial agent becomes necessary so as to bring about an economical problem.

An object of the present invention is to provide: an antibacterial agent which can be limitedly stationed at a required site of a material surface or the like and can persistently provide effects excellent in antifungal and antiviral properties in addition to antibacterial property; a substrate surface treatment method using the same; an antibacterial member using the same; an antibacterial agent composition; and a substrate surface treatment method using the same.

Means for Solving the Problems

In this specification, the present invention will be discussed separately from a first aspect "I" and a second aspect "II", as a matter of convenience.

<Invention "I">

An antibacterial agent according to the present invention is an antibacterial agent that will be discussed as Invention I-1.

The present invention is an antibacterial agent including as an active component a resin having a bismethide acid group or a bismethide acid salt, i.e., a resin having an organic group represented by general formula (I-1).

[Invention I-1]

An antibacterial agent including as an active component a resin having an organic group represented by general formula (I-1).

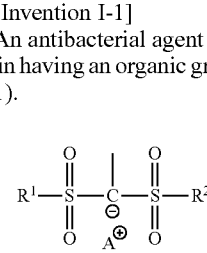

(I-1)

(In the formula (I-1), $R^1$ and $R^2$ mutually independently represent a $C_1$-$C_4$ fluoroalkyl group. "C" and "A" are bonded to each other through a covalent bond or an ionic bond, and "A" represents a hydrogen atom or a cation.)

When "A" is a hydrogen atom, a carbon of bismethide acid group can easily dissociate the hydrogen atom into the form of $H^+$ ion by a strong electron-withdrawing property of perfluoromethide, so that a C—H bond has both a covalent bond property and an ionic bond property. Since bismethide acid can easily become a bismethide acid salt in the presence of a cation, the organic group contained in the antibacterial agent of the present invention to act as an antibacterial active component is required only to be either a bismethide acid group or an organic group having a bismethide acid salt.

Additionally, the antibacterial agent according to the present invention is an antibacterial agent as will be discussed in Invention I-2 to I-8.

Antibacterial agents as will be discussed in Inventions I-2 to I-8 contain as an active component a resin where a bismethide acid group is bonded to a specific polymer chain. Thus a bismethide acid group or an organic group having a bismethide acid group is bonded to the polymer chain, volatilization and elusion of the active component is suppressed and the antibacterial property is sustained for a long period of time as compared with the case where the antibacterial agent is merely kneaded into a resin.

A repeating unit having an organic group (a bismethide acid group, or an organic group having a bismethide acid salt)

represented by general formula (I-1) is exemplified by a repeating unit (I-a) contained in the resin of Invention I-2 and represented by general formula (I-2). As examples of the repeating unit represented by general formula (I-2), it is possible to cite: a repeating unit (I-a-1) having an ester bond and represented by general formula (I-3) as discussed in Invention I-3; a repeating unit (I-a-2) having a styrene chain in a main chain and represented by general formula (I-4) as discussed in Invention I-4; and a repeating unit (I-a-3) having a norbornene ring in a main chain and represented by general formula (I-5) as discussed in Invention I-5.

[Invention I-2]

An antibacterial agent as discussed in Invention I-1, wherein the resin is a resin having a repeating unit (I-a) represented by general formula (I-2).

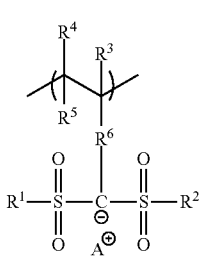

(I-2)

(In the formula (I-2), $R^1$ and $R^2$ mutually independently represent a $C_1$-$C_4$ fluoroalkyl group. $R^3$ represents a hydrogen atom, a $C_1$-$C_4$ alkyl group, a halogen atom or a $C_1$-$C_4$ fluoroalkyl group. $R^4$ and $R^5$ mutually independently represent a hydrogen atom, a $C_1$-$C_4$ alkyl group or a halogen atom. $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with fluorine atom or hydroxyl group. $R^3$ and $R^4$, or $R^5$ and $R^6$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

$R^1$ and $R^2$ as mentioned above and shown in general formulas (I-1) and (I-2) are exemplified by $CF_3$, $C_2F_5$, and linear or branched $C_3F_7$ and $C_4F_9$. In view of easiness of synthesis of the antibacterial agent according to the present invention, $CF_3$ is preferably used.

[Invention I-3]

An antibacterial agent as discussed in Invention I-2, wherein the repeating unit (I-a) is a repeating unit (I-a-1) represented by general formula (I-3).

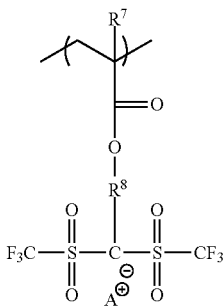

(I-3)

(In the formula (I-3), $R^7$ represents a hydrogen atom, an alkyl group, a halogen atom or a trifluoromethyl group. $R^8$ represents a single bond, a $C_1$-$C_{12}$ linear, branched or cyclic divalent hydrocarbon group, or a divalent hydrocarbon group having any combination of these, wherein $R^8$ may have an ether bond, an ester bond, an amide bond or an urethane bond, some carbon atoms contained in $R^8$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention I-4]

An antibacterial agent as discussed in Invention I-2, wherein the repeating unit (I-a) is a repeating unit (I-a-2) represented by general formula (I-4).

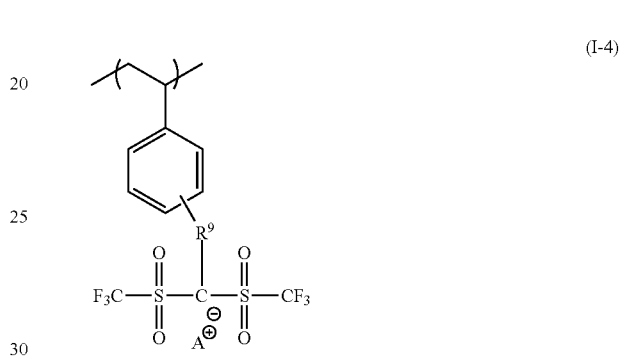

(I-4)

(In the formula (I-4), $R^9$ represents a single bond, a $C_1$-$C_{12}$ linear, branched or cyclic divalent hydrocarbon group, or a divalent hydrocarbon group having any combination of these, wherein $R^9$ may have an ether bond, an ester bond, an amide bond or an urethane bond, some carbon atoms contained in $R^9$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention I-5]

An antibacterial agent as discussed in Invention I-2, wherein the repeating unit (I-a) is a repeating unit (I-a-3) represented by general formula (I-5).

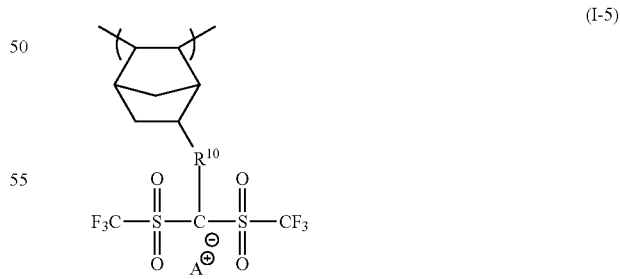

(I-5)

(In the formula (I-5), $R^{10}$ represents a single bond, a $C_1$-$C_{12}$ linear, branched or cyclic divalent hydrocarbon group, or a divalent hydrocarbon group having any combination of these, wherein $R^{10}$ may have an ether bond, an ester bond, an amide bond or an urethane bond, some carbon atoms contained in $R^{10}$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention I-6]

An antibacterial agent as discussed in Invention I-2, wherein the resin is a resin further having a repeating unit (I-b-1) represented by general formula (I-6).

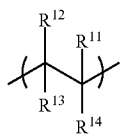
(I-6)

(In the formula (I-6), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group. Additionally, $R^{11}$ and $R^{12}$, or $R^{13}$ and $R^{14}$ may be bonded to each other to form a ring and may contain a $C_3$-$C_{12}$ single, double or multi ring structure.)

[Invention I-7]

An antibacterial agent as discussed in Invention I-2, wherein the resin is a resin further having a repeating unit (I-b-2) represented by general formula (I-7).

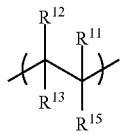
(I-7)

(In the formula (I-7), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ has a group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.)

[Invention I-8]

A curable antibacterial agent as discussed in Invention I-7, containing a cross-linking agent, characterized in that the resin is cross-linked by a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group.

More specifically, there is used at least one cross-linking agent selected from the group consisting of hexamethylene diisocyanate, 1,4-butanediol diglycidyl ether, paraformaldehyde, dimethyldichlorosilane, dimethyldimethoxysilane, methylolated melamine and its derivative with sulfur, benzoyl peroxide and azobisisobutyronitrile.

Referring now to Inventions I-9 to I-14, a substrate surface treatment method using an antibacterial agent according to the present invention will be discussed.

An antibacterial agent containing as an active component a bismethide acid group or an organic group having a bismethide acid salt as discussed in Invention I-1, and more specifically, antibacterial agents containing as an active component a resin where a bismethide acid group or an organic group having a bismethide acid salt is bonded to a specific polymer chain as discussed in Inventions I-2 to I-8 can be applied in a variety of forms.

For example, it is possible to apply a substrate surface treatment method where a resin is dissolved in a solvent and then applied onto a substrate thereby forming an antibacterial film, a method of shaping a resin into a sheet and then attaching it to a substrate surface, and the like.

It is also possible to employ a surface treatment method of adding a cross-linking agent to a state of a polymerizable compound serving as a precursor of a resin or a state of a polymerizable compound serving as a precursor of a repeating unit of a resin as necessary and then applying or attaching it to a substrate and then heating it or irradiating it with light such as ultraviolet rays or the like to cause polymerization or cross-linking thereby forming a rigid antibacterial resin film.

According to the substrate surface treatment method of the present invention, it is possible to coat a surface of an object with an antibacterial agent composition or it is possible to apply or attach the antibacterial agent composition to a substrate surface. With this, antibacterial property can be efficiently imparted to an antibacterial member.

[Invention I-9]

A substrate surface treatment method characterized by applying or attaching an antibacterial agent as discussed in any of Inventions I-1 to I-8 to a substrate surface thereby forming a film.

[Invention I-10]

A substrate surface treatment method characterized by applying or attaching a polymerizable compound to a substrate surface thereby forming a film formed of an antibacterial agent as discussed in any of Inventions I-1 to I-8, the polymerizable compound being a precursor of a repeating unit represented by general formula (II-1).

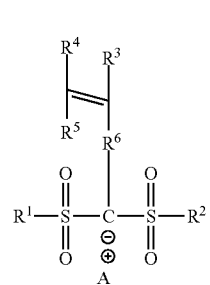
(II-1)

(In the formula (II-1), $R^1$ and $R^2$ mutually independently represent a $C_1$-$C_4$ fluoroalkyl group. $R^3$ represents a hydrogen atom, a $C_1$-$C_4$ alkyl group, a halogen atom or a $C_1$-$C_4$ fluoroalkyl group. $R^4$ and $R^5$ mutually independently represent a hydrogen atom, a $C_1$-$C_4$ alkyl group or a halogen atom. $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with fluorine atom or hydroxyl group. $R^3$ and $R^4$, or $R^5$ and $R^6$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

[Invention I-11]

A substrate surface treatment method as discussed in Invention I-10, characterized by adding another polymerizable compound represented by general formula (II-5) or (II-6) to the polymerizable compound represented by general formula (II-1) and then applying or attaching it to a substrate surface thereby forming a film formed of an antibacterial agent as discussed in Invention I-6 or I-7.

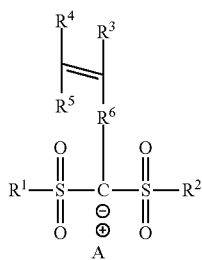

(II-1)

(In the formula (II-1), $R^1$ and $R^2$ mutually independently represent a $C_1$-$C_4$ fluoroalkyl group. $R^3$ represents a hydrogen atom, a $C_1$-$C_4$ alkyl group, a halogen atom or a $C_1$-$C_4$ fluoroalkyl group. $R^4$ and $R^5$ mutually independently represent a hydrogen atom, a $C_1$-$C_4$ alkyl group or a halogen atom. $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with fluorine atom or hydroxyl group. $R^3$ and $R^4$, or $R^5$ and $R^6$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

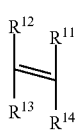

(II-5)

(In the formula (II-5), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group. Additionally, $R^{11}$ and $R^{12}$, or $R^{13}$ and $R^{14}$ may be bonded to each other to form a ring and may contain a $C_3$-$C_{12}$ single, double or multi ring structure.)

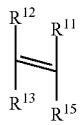

(II-6)

(In the formula (II-6), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ has a group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.)

Incidentally, the polymerizable compounds provided as a precursor of a repeating unit and represented by general formulas (II-1), (II-5) and (I-6-3) is not limited to a monomer and may be an oligomer that combines the monomers.

[Invention I-12]

A substrate surface treatment method as discussed in any of Inventions I-9 to I-11, characterized in that the film of an antibacterial agent of Invention I-8 is formed after further adding a cross-linking agent.

In the substrate surface treatment method according to the present invention, the cross-linking agent is exemplified by a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group.

More specifically, there is used at least one cross-linking agent selected from the group consisting of hexamethylene diisocyanate, 1,4-butanediol diglycidyl ether, paraformaldehyde, dimethyldichlorosilane, dimethyldimethoxysilane methylolated melamine and its derivative with sulfur, benzoyl peroxide and azobisisobutyronitrile.

[Invention I-13]

A substrate surface treatment method as discussed in Invention I-12, characterized by heating the film to cause polymerization or cross-linking thereby curing the film.

In the substrate surface treatment method according to the present invention, tert-butyl peroxypivalate is preferably used as a polymerization initiator for the polymerization.

[Invention I-14]

A substrate surface treatment method as discussed in Invention I-12, characterized by irradiating the film with light to cause polymerization or cross-linking thereby curing the film.

In the substrate surface treatment method according to the present invention, 1-hydroxycyclohexyl phenyl ketone is preferably used as an initiator for the photopolymerization.

Moreover, the substrate surface treatment method according to the present invention is not limited to the above-mentioned polymerizable compound, initiators and cross-linking agent, and may employ a solvent. As the solvent, 2-butanone or cyclohexanone is preferably usable.

[Invention I-15]

A method for producing an antibacterial member, characterized by conducting a surface treatment according to a surface treatment method as discussed in Inventions I-9 to I-14.

<Invention "II">

An antibacterial agent composition according to the present invention includes a fluorine-containing polymerizable compound represented by general formula (II-1) and fluorine-containing polymerizable compounds represented by general formulas (II-2) to (II-4), the compounds having a bismethide acid group or an organic group including a bis-methide acid salt. By causing a polymerization between fluorine-containing polymerizable compounds or between a fluorine-containing polymerizable compound and another polymerizable compound after initiating cross-linking or adding a solvent, the antibacterial agent composition becomes an antibacterial resin.

In general formula (II-1), "C" (carbon) and "A" are bonded to each other through a covalent bond or an ionic bond, and "A" represents a hydrogen atom or a cation.

When "A" is a hydrogen atom, a carbon of bismethide acid group can easily dissociate the hydrogen atom by a strong electron-withdrawing property of perfluoromethide, so that a C—H bond has both a covalent bond property and an ionic bond property.

Since bismethide acid can easily become a bismethide acid salt due to the cation, the organic group contained in the antibacterial agent compound of the present invention to act as an antibacterial active component is required only to be either a bismethide acid group or an organic group having a bismethide acid salt.

[Invention II-1]

An antibacterial agent composition including a fluorine-containing polymerizable compound represented by general formula (II-1).

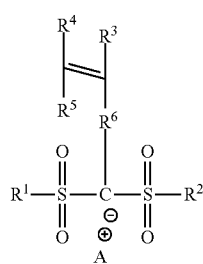

(II-1)

(In the formula (II-1), $R^1$ and $R^2$ mutually independently represent a $C_1$-$C_4$ fluoroalkyl group. $R^3$ represents a hydrogen atom, a $C_1$-$C_4$ alkyl group, a halogen atom or a $C_1$-$C_4$ fluoroalkyl group. $R^4$ and $R^5$ mutually independently represent a hydrogen atom, a $C_1$-$C_4$ alkyl group or a halogen atom. $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with fluorine atom or hydroxyl group. $R^3$ and $R^4$, or $R^5$ and $R^6$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

$R^1$ and $R^2$ as mentioned above and shown in general formulas (II-1) and (II-2) are exemplified by $CF_3$, $C_2F_5$, and linear or branched $C_3F_7$ and $C_4F_9$. In view of easiness of synthesis of the antibacterial agent composition according to the present invention, $CF_3$ is preferably used.

A fluorine-containing polymerizable compound (II-a) represented by general formula (II-1) can be exemplified by: a fluorine-containing polymerizable compound (II-a-1) having an ester bond and represented by general formula (II-2) as discussed in Invention II-2; a fluorine-containing polymerizable compound (II-a-2) having a styrene chain in a main chain and represented by general formula (II-3) as discussed in Invention II-3; and a fluorine-containing polymerizable compound (II-a-3) having a norbornene ring in a main chain and represented by general formula (II-4) as discussed in Invention II-4.

[Invention II-2]

An antibacterial agent composition as discussed in Invention II-1, including a fluorine-containing polymerizable compound represented by general formula (II-2).

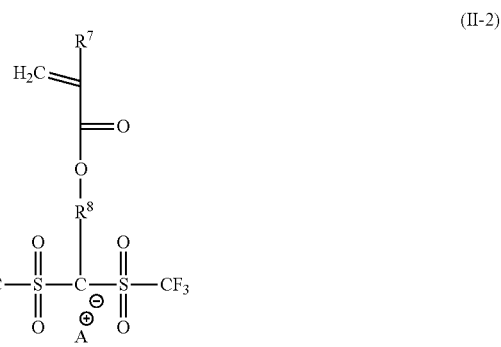

(II-2)

(In the formula (II-2), $R^7$ represents a hydrogen atom, an alkyl group, a halogen atom or a trifluoromethyl group. $R^8$ represents a single bond, a $C_1$-$C_{12}$ linear, branched or cyclic divalent hydrocarbon group, or a divalent hydrocarbon group having any combination of these, wherein $R^8$ may have an ether bond, an ester bond, an amide bond or an urethane bond, some carbon atoms contained in $R^8$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention II-3]

An antibacterial agent composition as discussed in Invention II-1, including a fluorine-containing polymerizable compound represented by general formula (II-3).

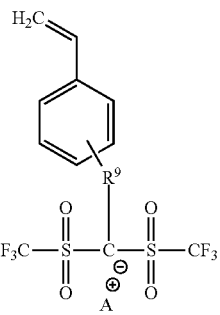

(II-3)

(In the formula (II-3), $R^9$ represents a single bond, a $C_1$-$C_{12}$ linear, branched or cyclic divalent hydrocarbon group, or a divalent hydrocarbon group having any combination of these, wherein $R^9$ may have an ether bond, an ester bond, an amide bond or an urethane bond, some carbon atoms contained in $R^9$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention II-4]

An antibacterial agent composition as discussed in Invention II-1, including a fluorine-containing polymerizable compound represented by general formula (II-4).

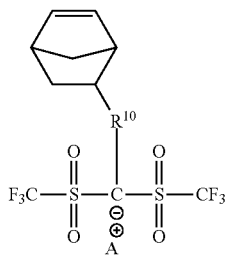

(II-4)

(In the formula (II-4), $R^{10}$ represents a single bond, a $C_1$-$C_{12}$ linear, branched or cyclic divalent hydrocarbon group, or a divalent hydrocarbon group having any combination of these, wherein $R^{10}$ may have an ether bond, an ester bond, an amide bond or an urethane bond, some carbon atoms contained in $R^{10}$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

It is also possible in the antibacterial agent composition according to the present invention to use a polymerizable compound (II-b-1) represented by general formula (II-5) as discussed in Invention II-5 or a polymerizable compound (II-b-2) represented by general formula (II-6) as discussed in Invention II-6, in addition to the fluorine-containing polymerizable compound (II-a), for the purpose of adjusting the content of the active component (i.e., a bismethide acid group or a organic group including a bismethide acid salt) in the antibacterial agent or adjusting the solvent solubility, applicability and mechanical properties of a resin or introducing a cross-linkable functional group. The polymerizable compound (II-b-1) is a polymerizable compound having no cross-linkable group and the polymerizable compound (II-b-2) is a polymerizable compound having a cross-linkable group.

[Invention II-5]

An antibacterial agent composition as discussed in Inventions II-1 to II-4, further including a polymerizable compound represented by general formula (II-5).

(II-5)

(In the formula (II-5), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group. Additionally, $R^{11}$ and $R^{12}$, or $R^{13}$ and $R^{14}$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

[Invention II-6]

An antibacterial agent composition as discussed in Inventions II-1 to II-5, further including a polymerizable compound represented by general formula (II-6).

(II-6)

(In the formula (II-6), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ has one or more kinds of functional groups selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.)

In the substrate surface treatment method according to the present invention, the cross-linking agent is exemplified by a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group.

More specifically, there is used at least one cross-linking agent selected from the group consisting of hexamethylene diisocyanate, 1,4-butanediol diglycidyl ether, paraformaldehyde, dimethyldichlorosilane, dimethyldimethoxysilane methylolated melamine and its derivative with sulfur, benzoyl peroxide and azobisisobutyronitrile.

[Invention II-7]

An antibacterial agent composition as discussed in Invention II-5 or II-6, further containing a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group.

[Invention II-8]

An antibacterial resin obtained by polymerization reaction or cross-linking reaction of an antibacterial agent composition as discussed in Inventions II-1 to II-7.

Referring now to Inventions II-9 to II-13, a substrate surface treatment method using an antibacterial agent composition according to the present invention will be discussed.

An antibacterial agent composition that includes a fluorine-containing polymerizable compound as discussed in Inventions II-1 to II-7 can be applied in a variety of forms.

For example, the resin obtained by polymerization of the composition of the antibacterial agent may be dissolved in a solvent and applied onto a substrate, then it is possible to form an antibacterial film.

It is also possible to employ a surface treatment method of adding another polymerizable compound or a cross-linking agent to a fluorine-containing polymerizable compound (that has a bismethide acid group or an organic group including a bismethide acid salt) as necessary to obtain a antibacterial agent composition, and then applying or attaching it to a substrate and then heating it or irradiating it with light such as ultraviolet rays or the like to cause polymerization or cross-linking thereby forming a rigid antibacterial resin film.

According to the substrate surface treatment method of the present invention, it is possible to coat a surface of an object with an antibacterial agent composition or it is possible to apply or attach the antibacterial agent composition to a substrate surface. With this, antibacterial property can be efficiently imparted to an antibacterial member.

[Invention II-9]

A substrate surface treatment method characterized by applying or attaching an antibacterial agent composition as discussed in Inventions II-1 to II-7 to a substrate surface.

[Invention II-10]

A treatment method as discussed in Invention II-9, characterized by applying or attaching an antibacterial agent composition to which a polymerizable compound represented by general formula (II-5) or (II-6) is further added, to a substrate surface.

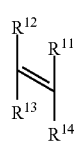

(II-5)

(In the formula (II-5), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group. Additionally, $R^{11}$ and $R^{12}$, or $R^{13}$ and $R^{14}$ may be bonded to each other to form a ring and may contain a $C_3$-$C_{12}$ single, double or multi ring structure.)

(II-6)

(In the formula (II-6), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ has a group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.)

[Invention II-11]

A method as discussed in Invention II-10, characterized in that the film is formed after further adding a cross-linking agent.

[Invention II-12]

A method as discussed in Inventions II-9 to II-11, characterized by heating the film to cause polymerization or cross-linking thereby curing the film.

In the substrate surface treatment method according to the present invention, tert-butyl peroxypivalate is preferably used as a polymerization initiator for the polymerization.

[Invention II-13]

A method as discussed in Inventions II-9 to II-11, characterized by irradiating the film with light to cause polymerization or cross-linking thereby curing the film.

In the substrate surface treatment method according to the present invention, 1-hydroxycyclohexyl phenyl ketone is preferably used as an initiator for the photopolymerization.

Moreover, the substrate surface treatment method according to the present invention is not limited to the above-mentioned polymerizable compound, initiators and cross-linking agent, and may employ a solvent. As the solvent, 2-butanone or cyclohexanone is preferably usable.

[Invention II-14]

A method for producing an antibacterial member, characterized by conducting a surface treatment according to a method as discussed in Inventions II-9 to II-13.

[Invention II-15]

A fluorine-containing polymerizable compound represented by general formula (II-7).

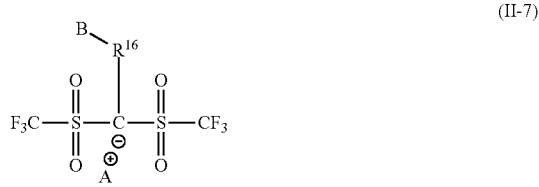

(In the formula (II-7), $R^{16}$ represents a $C_1$-$C_{12}$ linear, branched or cyclic divalent hydrocarbon group, or a divalent group having any combination of these and having carbon atoms partially or entirely substituted with silicon, wherein $R^{16}$ may have an ether bond, an ester bond, an amide bond or an urethane bond, and some or all hydrogen atoms contained in $R^{16}$ may be substituted with fluorine atom or hydroxyl group. "C" and "A" are bonded to each other through a covalent bond or an ionic bond, and "A" represents a hydrogen atom or a cation. "B" is either one of groups represented as follows.)

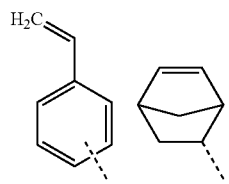

Effects of the Invention

<Effects of Invention "I">

An antibacterial agent including as an active component a resin having an organic group represented by general formula (I-1), i.e., a resin having a bismethide acid group or an organic group including a bismethide acid salt can exhibit an antibacterial activity even if the content or concentration of a bismethide acid group or an organic group including a bismethide acid salt is low. When the content of "$(CF_3SO_2)_2C-$" (a bismethide acid group or an organic group including a bismethide acid salt) in a resin is at least not lower than 0.1 mass % relative to the resin, the antibacterial effect is shown. When the content is not lower than 1 mass %, there is exhibited an effect of high antibacterial activity.

Additionally, in an antibacterial agent including as an active component a resin where a bismethide acid group or an organic group containing a bismethide acid salt is bonded to a polymer chain, the active component (i.e., a bismethide acid group or an organic group having a bismethide acid group) is bonded to a polymer chain. With this, volatilization and elusion of the active component is suppressed and the antibacterial property is sustained for a long period of time as compared with conventional antibacterial agents obtained by kneading an antibacterial agent into a resin.

More specifically, by employing the antibacterial agent of the present invention and the surface treatment method using the same, a methide group can be limitedly stationed at a required site of a material surface or the like, and additionally, an antibacterial agent persistently exhibiting great antibacterial, antifungal and antiviral effects and an antibacterial member using the same are provided.

Furthermore, an antibacterial agent containing as an active component a resin having a bismethide acid group or an organic group including a bismethide acid salt, according to the present invention exhibits an antibacterial property even if the content or concentration of a bismethide acid group or an organic group including a bismethide acid salt is low.

An antibacterial agent that contains as an active component a resin having a bismethide acid group or an organic group including a bismethide acid salt, and more particularly an antibacterial agent that contains as an active component a resin where a bismethide acid group or an organic group including a bismethide acid salt is bonded to a specific polymer chain is provided such that an active component (a bismethide acid group or an organic group including a bismethide acid salt) according to the present invention is bonded to a polymer chain, so that volatilization and elusion of the active component is suppressed and the antibacterial property is sustained for a long period of time as compared with the case where the antibacterial agent is merely kneaded into a resin. In the antibacterial agent of the present invention, it is easy to evenly distribute a bismethide acid group or an organic group including a bismethide acid salt in the specific resin. A bismethide acid group or an organic group including a bismethide acid salt never be biased, so that a great safety is ensured.

An antibacterial agent containing as an active component a resin having a bismethide acid group or an organic group including a bismethide acid salt according to the present invention can be applied in a variety of forms. For example, by coating a surface of an object with an antibacterial agent according to a surface treatment method such as application and the like, it becomes possible to efficiently impart an antibacterial property to an antibacterial member. This results in the effect of reducing the used amount of the antibacterial agent.

Furthermore, an antibacterial agent containing as an active component a resin having a bismethide acid group or an organic group including a bismethide acid salt according to the present invention provides the antibacterial activity against a wide range of fungi. Not only an antibacterial property but also the effect of suppressing fungi and virus are effectively provided.

According to the present invention, there are provided: an antibacterial agent which has both antifungal and antiviral properties in addition to an excellent antibacterial property and has the persistence thereof and efficiently achieves the mass production thereof and applicable and usable in various fields including not only the household field but also the industrial field such as electronic materials and the like; a substrate surface treatment method using the same; and an antibacterial member using the same.

<Effects of Invention "II">

An antibacterial agent composition that includes a fluorine-containing polymerizable compound represented by general formula (II-1) and having a bismethide acid group or an organic group including a bismethide acid salt according to the present invention, and more specifically, an antibacterial agent composition that includes a fluorine-containing polymerizable compound represented by general formulas (II-2) to (II-4) (these general formulas are included in general formula (II-1)) can exhibit a great antibacterial activity even if the content or concentration of a bismethide acid group or an organic group including a bismethide acid salt is low. For example, when the content of "$(CF_3SO_2)_2C-$" (a bismethide acid group or an organic group including a bismethide acid salt) in a resin that had been polymerized is at least not lower than 0.1 mol % relative to the antibacterial agent composition, the antibacterial effect is confirmed. When the content is not lower than 1 mol %, there is exhibited a higher antibacterial effect.

Additionally, in the case of using the antibacterial agent composition of the present invention and applying a fluorine-containing polymerizable compound that includes a bismethide acid group or an organic group having a bismethide acid salt to a substrate and then causing polymerization to form a resin, there is obtained a film containing a resin where an active component (i.e., a bismethide acid group or an organic group containing a bismethide acid salt) is bonded to a polymer chain. With this, volatilization and elusion of the active component is suppressed and the antibacterial property is sustained for a long period of time as compared with conventional antibacterial agents obtained by merely kneading an antibacterial agent into a resin.

More specifically, by employing the antibacterial agent composition of the present invention and the surface treatment method using the same, a methide group can be limitedly stationed at a required site of a material surface or the like, and additionally, an antibacterial agent composition persistently exhibiting great antibacterial, antifungal and antiviral effects and an antibacterial member using the same are provided. It is easy to evenly distribute a bismethide acid group or an organic group including a bismethide acid salt in the film. A bismethide acid group or an organic group including a bismethide acid salt never be biased, so that a great safety is ensured.

Thus, an antibacterial agent composition that includes a fluorine-containing polymerizable compound including a resin having a bismethide acid group or an organic group including a bismethide acid salt according to the present invention can be applied in a variety of forms. For example, by coating a surface of an object according to a surface treatment method such as application and the like, it becomes possible to efficiently impart an antibacterial property to an antibacterial member. This results in the effect of reducing the used amount of the antibacterial agent.

Furthermore, an antibacterial agent composition that includes a fluorine-containing polymerizable compound including a resin having a bismethide acid group or an organic group including a bismethide acid salt according to the present invention provides the antibacterial activity against a wide range of fungi. Not only an antibacterial property but also the effect of suppressing fungi and virus are effectively provided.

According to the present invention, there are provided: an antibacterial agent composition which has both antifungal and antiviral properties in addition to an excellent antibacterial property and has the persistence thereof and efficiently achieves the mass production thereof and applicable and usable in various fields including not only the household field but also the industrial field such as electronic materials and the like; a substrate surface treatment method using the same; and an antibacterial member using the same.

MODE(S) FOR CARRYING OUT THE INVENTION

<Mode(s) for Carrying Out Invention "I">
1. Antibacterial Agent
First of all, an antibacterial agent according to the present invention will be discussed.

[Invention I-1]
An antibacterial agent including as an active component a resin having an organic group represented by general formula (I-1).

(I-1)

(In the formula (I-1), $R^1$ and $R^2$ mutually independently represent a $C_1$-$C_4$ fluoroalkyl group. "C" and "A" are bonded to each other through a covalent bond or an ionic bond, and "A" represents a hydrogen atom or a cation.)

When "A" is a hydrogen atom, a carbon of bismethide acid group can easily dissociate the hydrogen atom into the form of $H^+$ ion by a strong electron-withdrawing property of perfluoromethide, so that a C—H bond has both a covalent bond property and an ionic bond property. Since bismethide acid can easily become a bismethide acid salt in the presence of a cation, the organic group contained in the antibacterial agent of the present invention to act as an antibacterial active component is required only to be either a bismethide acid group or an organic group having a bismethide acid salt.

"A" represents either a hydrogen atom or a cation. When "A" is a monovalent cation, it may be bonded to an anion of the organic group represented by general formula (I-1) through an ionic bond to form a 1:1 bismethide acid salt. Furthermore, in the case where "A" is a polyvalent cation, it may form a salt together with an anion that has a corresponding valence number.

A cation to be bonded to "C" may be either a monovalent cation or a polyvalent cation. As the above-mentioned monovalent cation, it is possible to cite hydrogen ion ($H^+$), lithium ion ($Li^+$), sodium ion ($Na^+$), potassium ion ($K^+$), silver ion ($Ag^+$), copper(II) ion ($Cu^+$), mercury(II) ion ($Hg^+$), ammonium ion ($NH_4^+$), alkylammonium ion, anilinium ion, phenylammonium ion, pyridinium ion, pyrimidinium ion, pyrazolium ion, imidazolium ion, benzimidazolium ion, triazinium ion, hexahydro triazinium ion, triazolium ion, isoxazolium ion, thiazolium ion, isothiazolium ion, pyrrolium ion, benzthiazolium ion, thiazolin-2-onium ion, isothiazolin-3-onium ion, benzoisothiazolin-3-onium ion, benzothiazolin-2-onium ion, tetrahydro thiadiazine-2-thionium ion and the like.

Moreover, an alkylammonium ion can be exemplified by monoalkylammonium ion ($NRH_3^+$), dialkylammonium ion ($NR_2H_2^+$), trialkylammonium ion ($NR_3H^+$), tetraalkylammonium ion ($NR_4^+$) and the like. Furthermore, trialkylammonium ion can be exemplified by trimethylammonium ion ($N(CH_3)_3H^+$), triethylammonium ion ($N(C_2H_5)_3H^+$), tributylammonium ion ($N(C_4H_9)_3H^+$) and the like.

Furthermore, tetraalkylammonium ion can be exemplified by tetramethylammonium ion ($N(CH_3)_4^+$), tetraethylammonium ion ($N(C_2H_5)_4^+$), tetrabutylammonium ion ($N(C_4H_9)_4^+$) and the like.

Additionally, a divalent cation can be exemplified by magnesium ion ($Mg^{2+}$), calcium ion ($Ca^{2+}$), strontium ion ($Sr^{2+}$), barium ion ($Ba^{2+}$), cadmium ion ($Cd^{2+}$), nickel(II) ion ($Ni^{2+}$), zinc ion ($Zn^{2+}$), copper(II) ion ($Cu^{2+}$), mercury(II) ion ($Hg^{2+}$), iron(II) ion ($Fe^{2+}$), cobalt(II) ion ($Co^{2+}$), tin(II) ion ($Sn^{2+}$), lead(II) ion ($Pb^{2+}$), manganese(II) ion ($Mn^{2+}$) and the like.

Additionally, a trivalent cation can be exemplified by aluminium ion ($Al^{3+}$), iron(III) ion ($Fe^{3+}$), chromium(III) ion ($Cr^{3+}$) and the like.

Additionally, a tetravalent cation can be exemplified by tin(IV) ion ($Sn^{4+}$) and the like.

"A" may be a complex ion and may be exemplified by diammine silver ion ($[Ag(NH_3)_2]^+$), vioreo ($[CoCl_2(NH_3)_4]^+$), tetraammine zinc(II) ion ($[Zn(NH_3)_4]^{2+}$), tetraammine copper(II) ion ($[Cu(NH_3)_4]^{2+}$), tetraaqua copper(II) ion ($[Cu(H_2O)_4]^{2+}$), thiocyano iron(III) ion ($[Fe(SCN)]^{2+}$), hexaammine nickel(II) ion ($[Ni(NH_3)_6]^{2+}$), purpureo ($[CoCl(NH_3)_5]^{2+}$), hexaammine cobalt(III) ion ($[Co(NH_3)_6]^{3+}$), hexaaqua cobalt(III) ion ($[Co(H_2O)_6]^{3+}$), hexaammine chromium(III) ion ($[Cr(NH_3)_6]^{3+}$), roseo ($[Co(NH_3)_4(H_2O)_2]^{3+}$) and the like.

Additionally, the antibacterial agent according to the present invention is an antibacterial agent as discussed in Invention I-2 to I-8.

Antibacterial agents as discussed in Inventions I-2 to I-8 contain as an active component a resin where a bismethide acid group or an organic group including a bismethde acid salt is bonded to a specific polymer chain. Thus a bismethide acid "$(CF_3SO_2)_2C-$" that serves as the active component is bonded to the polymer chain, with which volatilization and elusion of the active component is suppressed and the antibacterial property is sustained for a long period of time as compared with the case where the antibacterial agent is merely kneaded into a resin.

Moreover, the resin having an organic group represented by general formula (I-1) exhibits an antibacterial activity even if the content or concentration of a bismethide acid group or an organic group including a bismethide acid salt is low. The antibacterial effect is observed only if the content of the organic group "$(CF_3SO_2)_2C-$" that is represented by general formula (I-1) (i.e., the content of a bismethide acid group or an organic group including a bismethide acid salt) in a resin is at least not lower than 0.1 mol % relative to the antibacterial agent. When the content is not lower than 1 mol %, there is provided the effect of higher antibacterial activity. The effect does not change even if the organic group is added to have a content of higher than 80 mol %, or rather the acidity is so increased as to be difficult to handle. Hence the content is preferably not lower than 0.1 mol % and not higher than 80 mol %. Accordingly, it is preferable that the antibacterial agent is prepared to have a content of "$(CF_3SO_2)_2C-$" (i.e., a content of a bismethide acid group or an organic group including a bismethide acid salt) of not lower than 0.1 mol % and not higher than 80 mol %.

A repeating unit having an organic group (a bismethide acid group, or an organic group having a bismethide acid salt) represented by general formula (I-1) is exemplified by a repeating unit (I-a) contained in the resin of Invention I-2 and represented by general formula (I-2). As examples of the repeating unit represented by general formula (I-2), it is possible to cite: a repeating unit (I-a-1) having an ester bond and represented by general formula (I-3) as discussed in Invention I-3; a repeating unit (I-a-2) having a styrene chain in a main chain and represented by general formula (I-4) as discussed in Invention I-4; and a repeating unit (I-a-3) having a norbornene ring in a main chain and represented by general formula (I-5) as discussed in Invention I-5.

[Invention I-2]

An antibacterial agent as discussed in Invention I-1, wherein the resin is a resin having a repeating unit (I-a) represented by general formula (I-2).

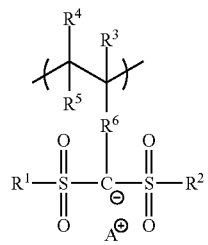

(I-2)

(In the formula (I-2), $R^1$ and $R^2$ mutually independently represent a $C_1$-$C_4$ fluoroalkyl group. $R^3$ represents a hydrogen atom, a $C_1$-$C_4$ alkyl group, a halogen atom or a $C_1$-$C_4$ fluoroalkyl group. $R^4$ and $R^5$ mutually independently represent a hydrogen atom, a $C_1$-$C_4$ alkyl group or a halogen atom. $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with fluorine atom or hydroxyl group. $R^3$ and $R^4$, or $R^5$ and $R^6$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

$R^1$ and $R^2$ as mentioned above and shown in general formulas (I-1) and (I-2) are exemplified by $CF_3$, $C_2F_5$, and linear or branched $C_3F_7$ and $C_4F_9$. In view of easiness of synthesis of the antibacterial agent according to the present invention, $CF_3$ is preferably used.

[Invention I-3]

An antibacterial agent as discussed in Invention I-2, wherein the repeating unit (I-a) is a repeating unit (I-a-1) represented by general formula (I-3).

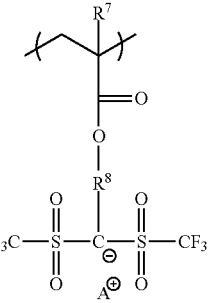

(I-3)

(In the formula (I-3), $R^7$ represents a hydrogen atom, an alkyl group, a halogen atom or a trifluoromethyl group. $R^8$ represents a single bond, a $C_1$-$C_{12}$ linear, branched or cyclic divalent hydrocarbon group, or a divalent hydrocarbon group having any combination of these, wherein $R^8$ may have an ether bond, an ester bond, an amide bond or an urethane bond, some carbon atoms contained in $R^8$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention I-4]

An antibacterial agent as discussed in Invention I-2, wherein the repeating unit (I-a) is a repeating unit (I-a-2) represented by general formula (I-4).

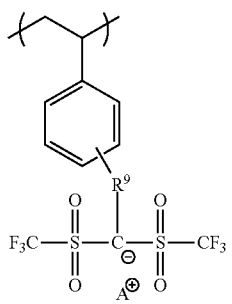

(I-4)

(In the formula (I-4), $R^9$ represents a single bond, a $C_1$-$C_{12}$ linear, branched or cyclic divalent hydrocarbon group, or a divalent hydrocarbon group having any combination of these, wherein $R^9$ may have an ether bond, an ester bond, an amide bond or an urethane bond, some carbon atoms contained in $R^9$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention I-5]

An antibacterial agent as discussed in Invention I-2, wherein the repeating unit (I-a) is a repeating unit (I-a-3) represented by general formula (I-5).

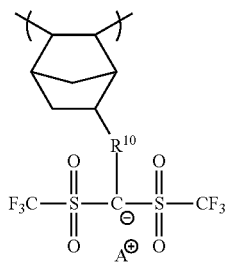

(I-5)

(In the formula (I-5), $R^{10}$ represents a single bond, a $C_1$-$C_{12}$ linear, branched or cyclic divalent hydrocarbon group, or a divalent hydrocarbon group having any combination of these, wherein $R^{10}$ may have an ether bond, an ester bond, an amide bond or an urethane bond, some carbon atoms contained in $R^{10}$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

It is also possible in the antibacterial agent according to the present invention to use a repeating unit (I-b-1) as discussed in Invention I-6 or a repeating unit (I-b-2) as discussed in Invention I-7, in addition to the repeating unit (I-a), for the purpose of adjusting the content of the active component (i.e., a bismethide acid group or a organic group including a bismethide acid salt) in the antibacterial agent or adjusting the solvent solubility, applicability and mechanical properties of a resin or introducing a cross-linkable functional group. The repeating unit (I-b-1) is a repeating unit having no cross-linkable group and the repeating unit (I-b-2) is a repeating unit having a cross-linkable group.

2. Repeating Unit

Then, a repeating unit (I-a) having a bismethide acid group and serving as a component of the antibacterial agent of the present invention will be discussed.

A repeating unit having a bismethide acid group represented by general formula (I-1) is exemplified by a repeating unit (I-a) contained in the resin of Invention I-2 and represented by general formula (I-2). As examples of the repeating unit represented by general formula (I-2), it is possible to cite: a repeating unit (I-a-1) having an ester bond and represented by general formula (I-3) as discussed in Invention I-3; a repeating unit (I-a-2) having a styrene chain in a main chain and represented by general formula (I-4) as discussed in Invention I-4; and a repeating unit (I-a-3) having a norbornene ring in a main chain and represented by general formula (I-5) as discussed in Invention I-5. In addition, it is possible to cite a resin containing a vinyl-based repeating unit (I-a), and a repeating unit (I-a) having an amide bond.

Thus, a resin contained in the antibacterial agent of Invention I-2 and having a bismethide acid group is exemplified by resins such as: a repeating unit (I-a-1) having an ester bond and represented by general formula (I-3) as discussed in Invention I-3; a repeating unit (I-a-2) having a styrene chain in a main chain and represented by general formula (I-4) as discussed in Invention I-4; and a repeating unit (I-a-3) having a norbornene ring in a main chain as discussed in Invention I-5. In addition, it is possible to cite a resin containing a vinyl-based repeating unit (I-a), and a resin containing a repeating unit (I-a) having an amide bond.

A repeating unit (I-a-1) having an ester bond and represented by general formula (I-3) as discussed in Invention I-3 can be exemplified by the following ester-based repeating units (I-a-1)-1 to (I-a-1)-3.

Ester-Based Repeating Unit (I-a-1)-1

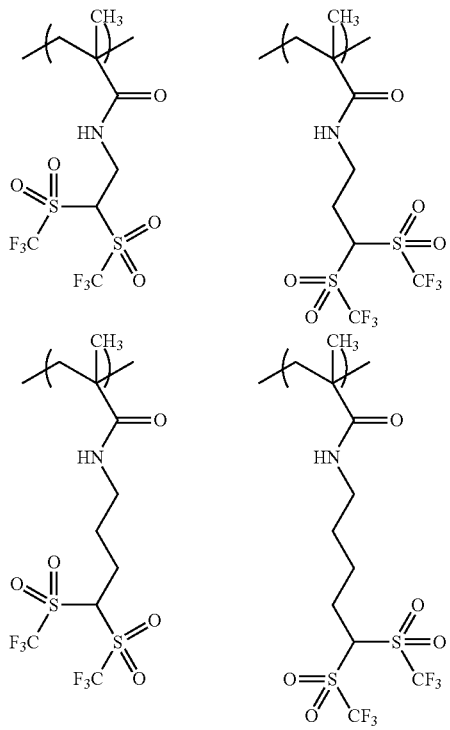

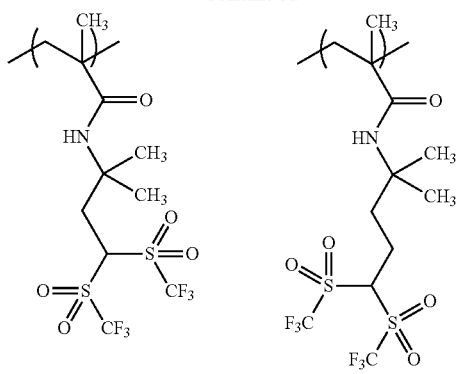
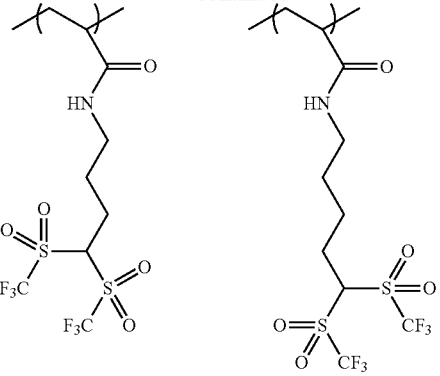
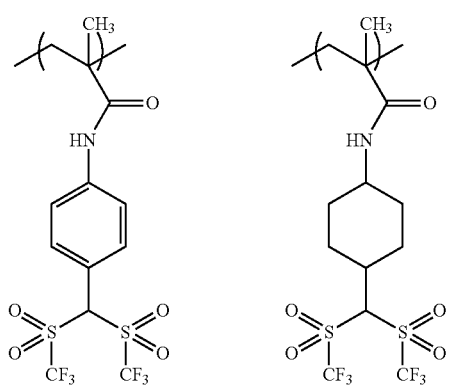
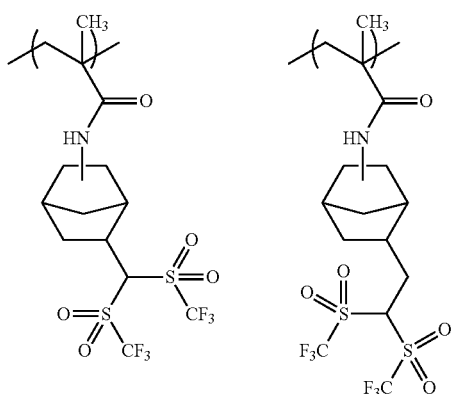
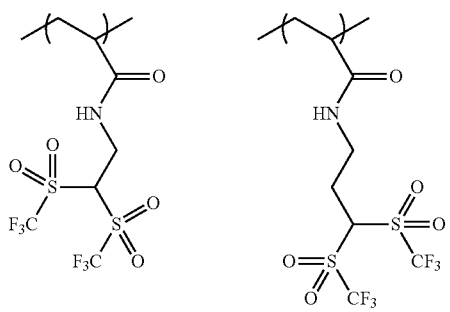

Ester-Based Repeating Unit (I-a-1)-2
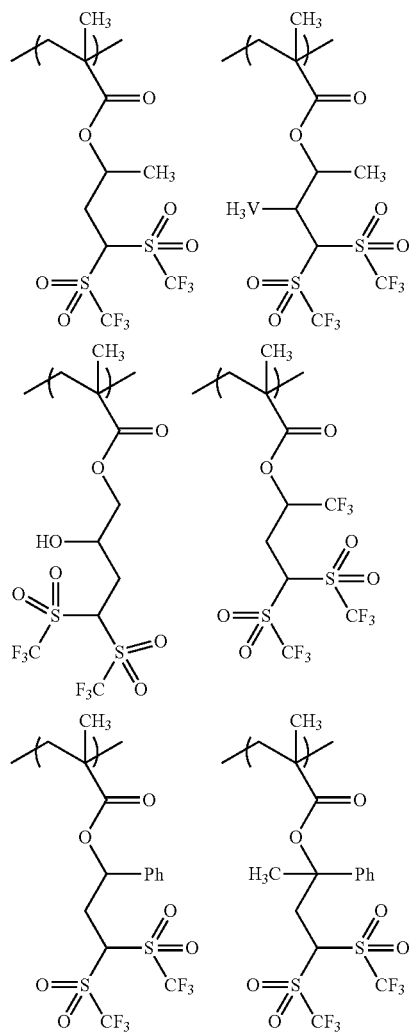
Ester-Based Repeating Unit (I-a-1)-3
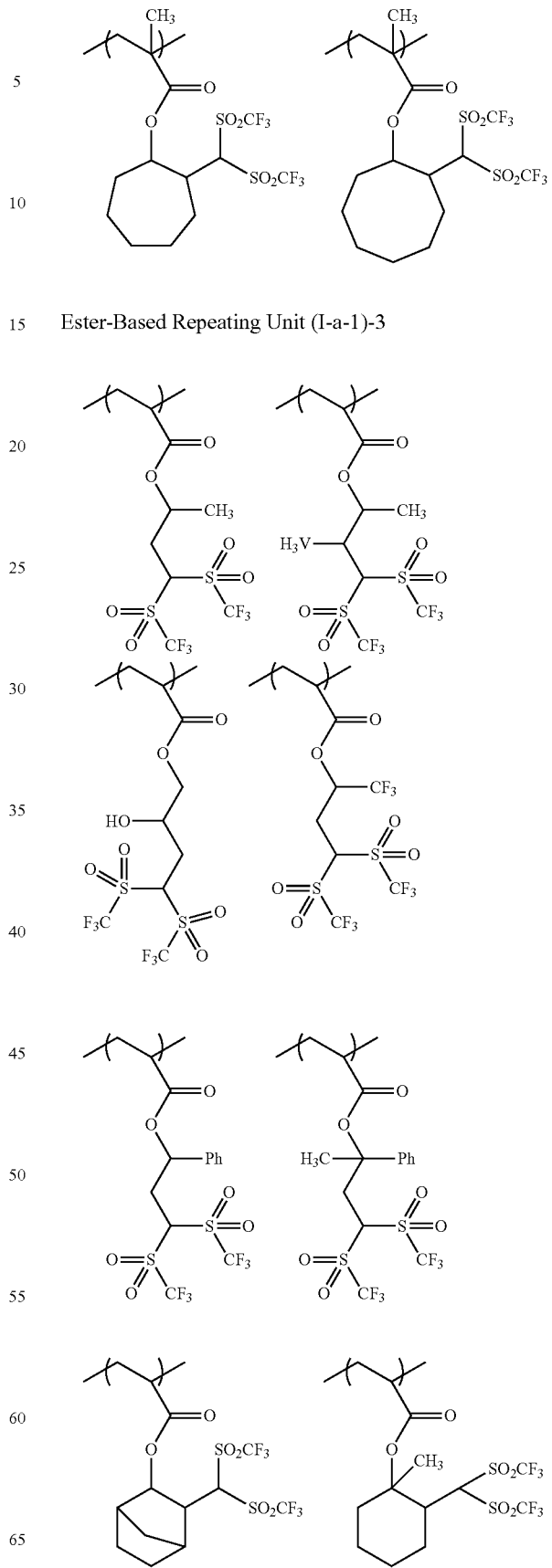

-continued

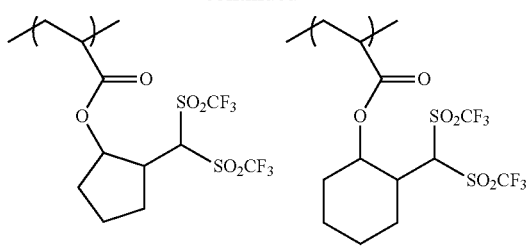

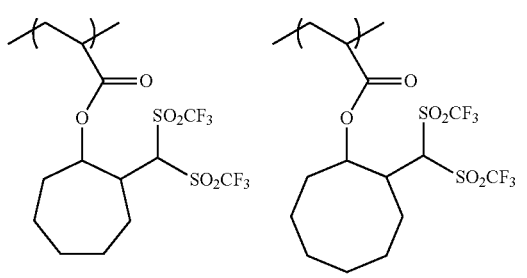

A repeating unit (I-a-2) having a styrene bond and represented by general formula (I-4) as discussed in Invention I-4 is exemplified by the following styrene-based repeating unit (I-a-2).

Styrene-Based Repeating Unit (I-a-2)

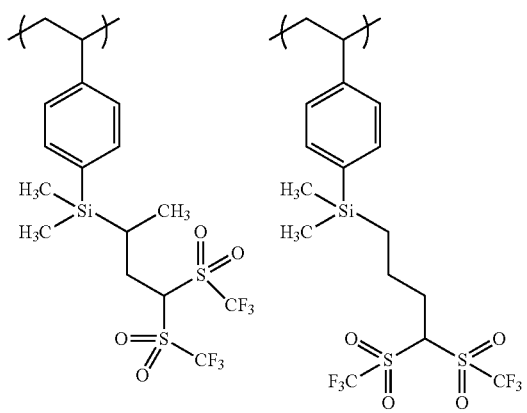

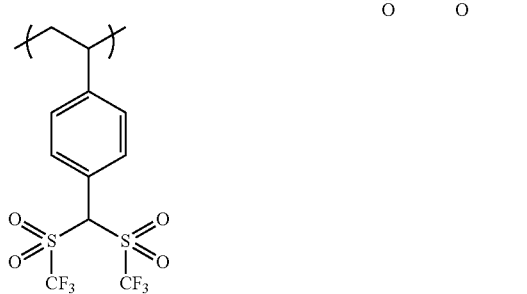

A repeating unit (I-a-3) represented by general formula (I-5) as discussed in Invention I-5 is exemplified by a repeating unit (I-a-3) having a norbornene ring in a main chain.

Repeating Unit (I-a-3) Having Norbornene Ring in Main Chain

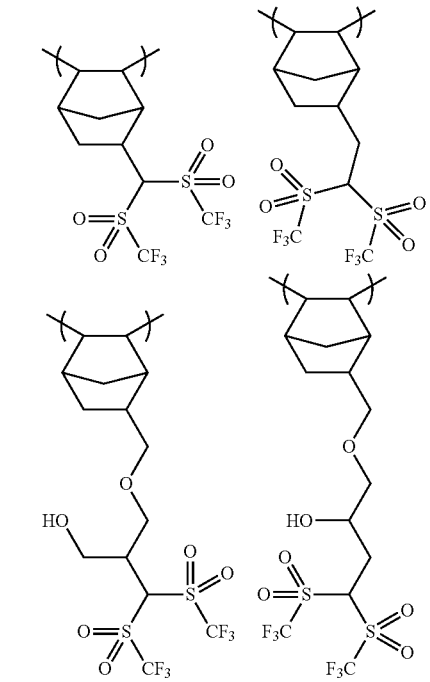

A repeating unit (I-a) represented by general formula (I-2) as discussed in Invention I-2 is exemplified by a vinyl-based repeating unit (I-a), an amide-based repeating unit (I-a)-1, (I-a)-2 and the like, a repeating unit (I-a) having a trismethide acid group, and the like.

Vinyl-Based Repeating Unit (I-a)

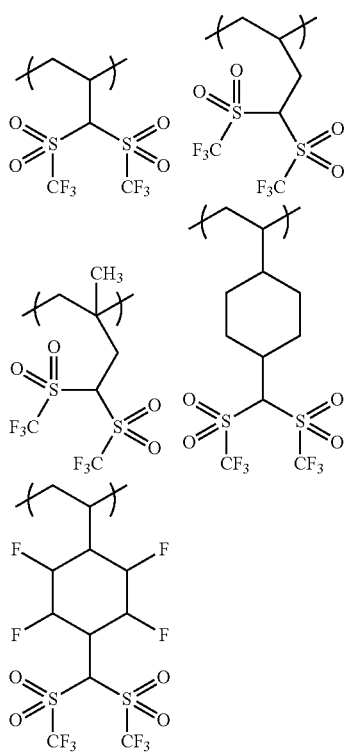

31
Amide-Based Repeating Unit (I-a)-1
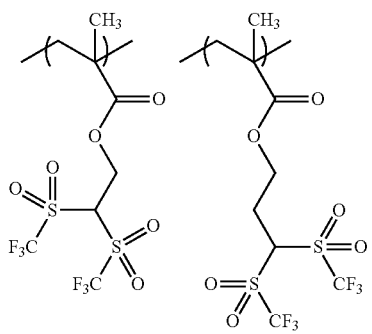
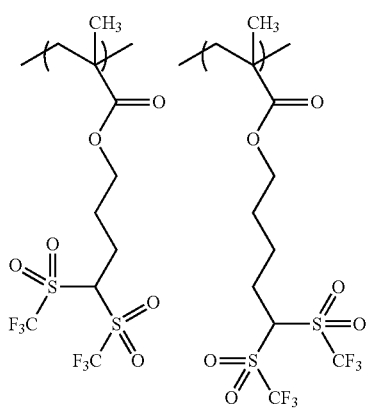
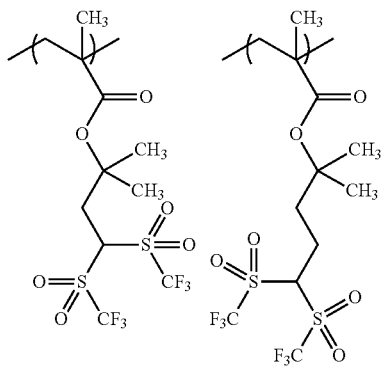
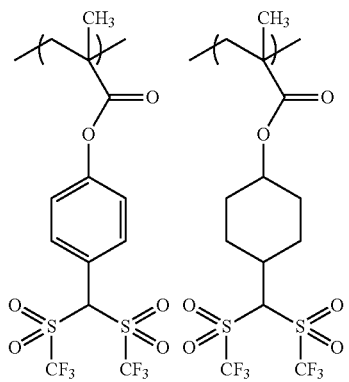
32
-continued
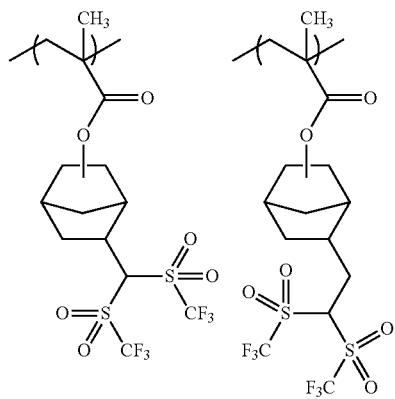
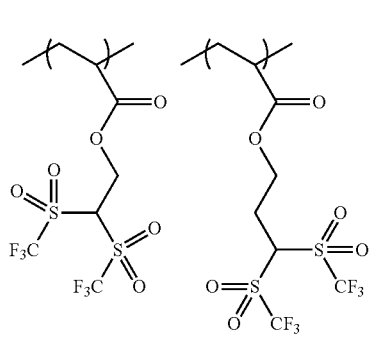
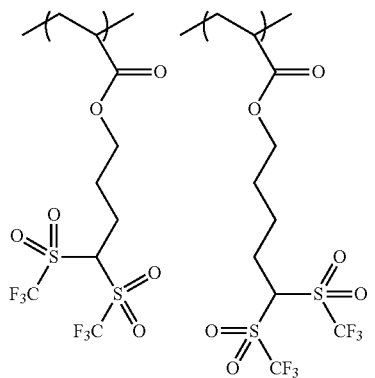
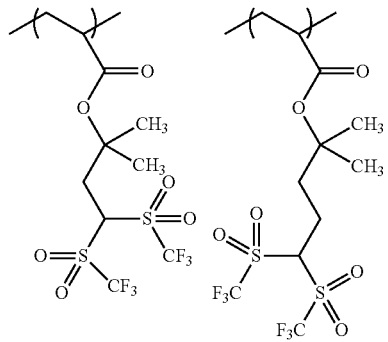

33
-continued
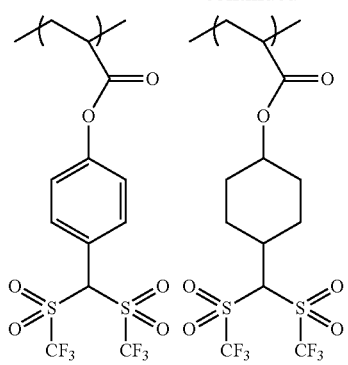
Amide-Based Repeating Unit (I-a)-2
34
-continued
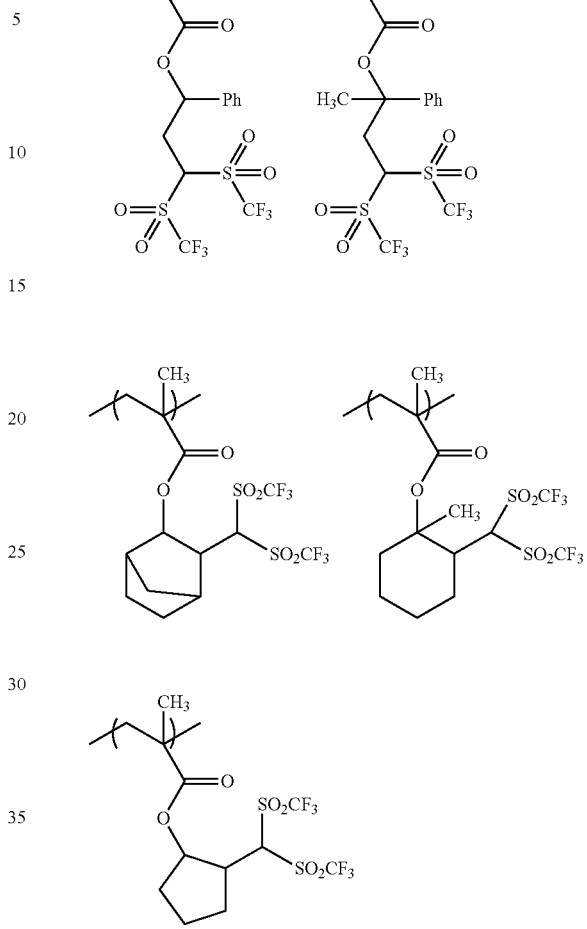
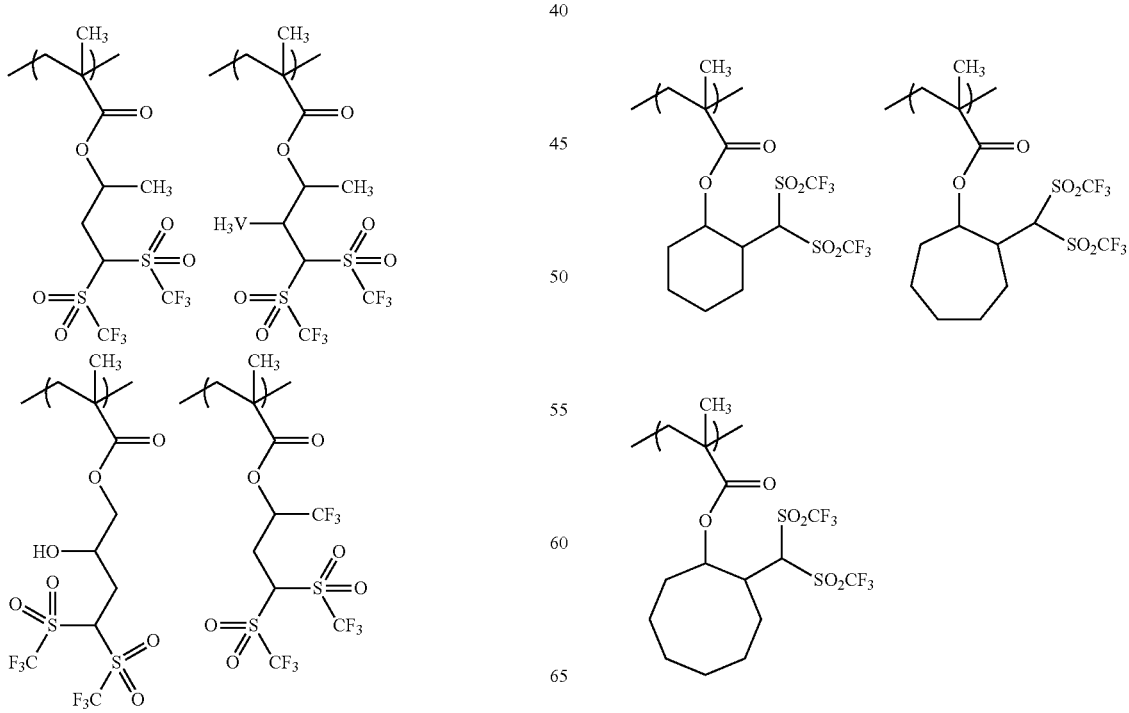

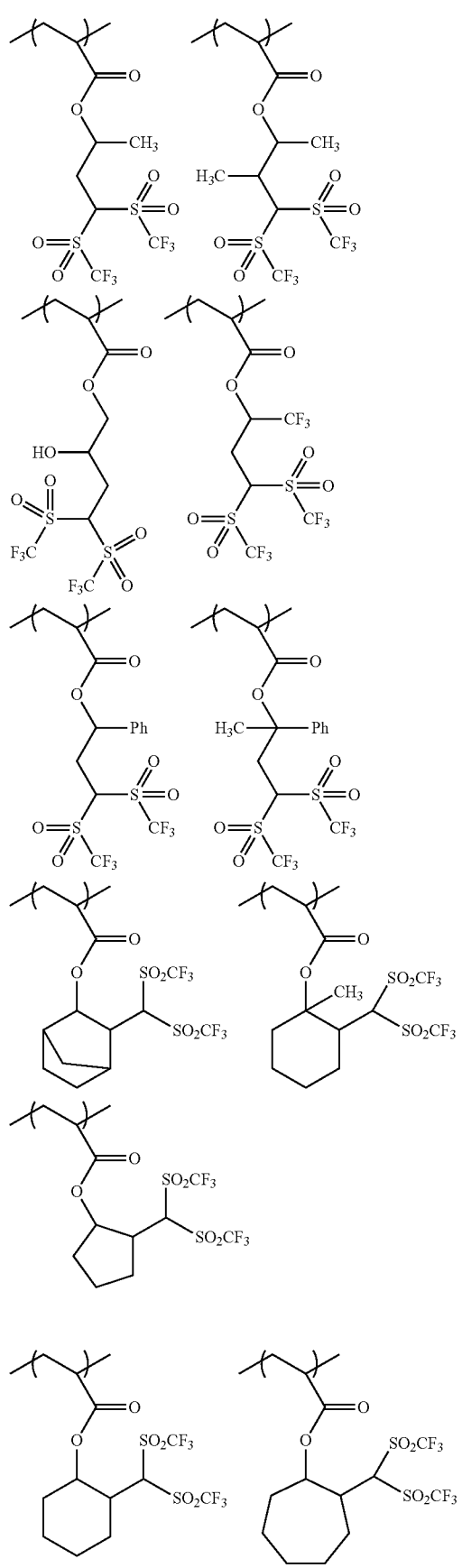
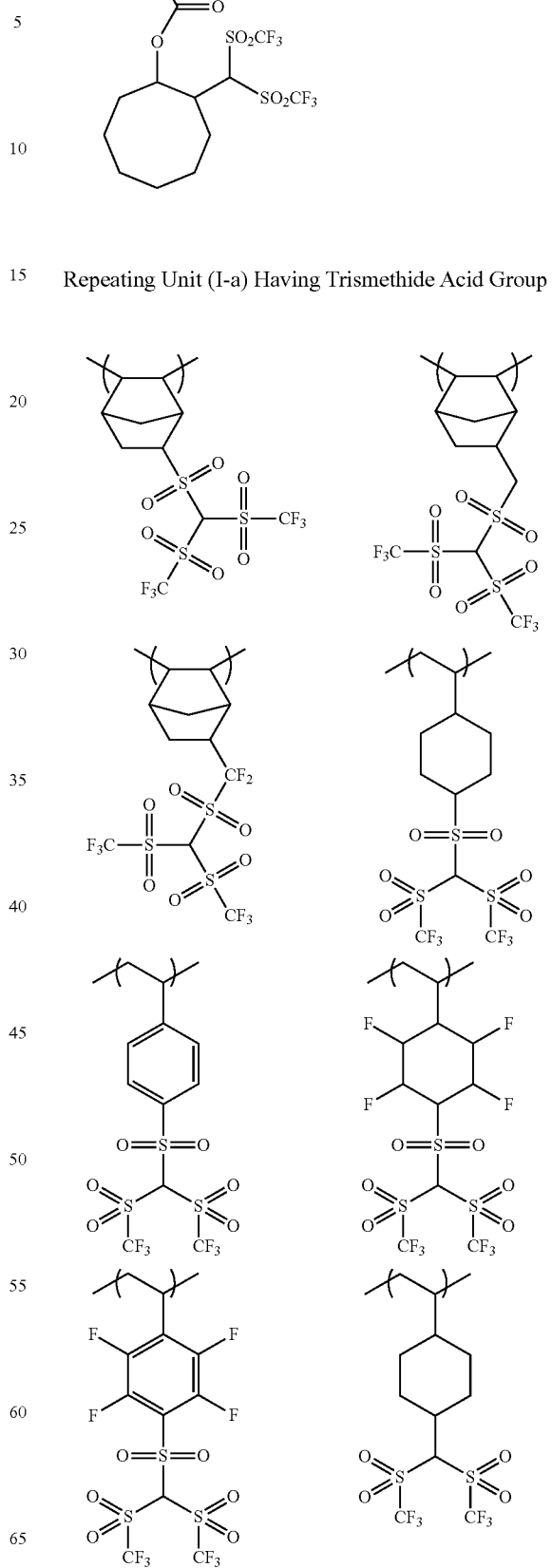
Repeating Unit (I-a) Having Trismethide Acid Group

-continued

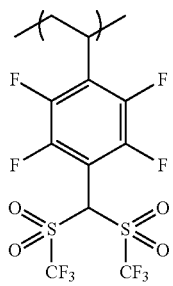 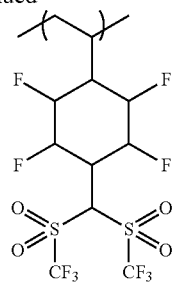

3. Repeating Units (I-b-1) and (I-b-2)

Then, repeating units (I-b-1) and (I-b-2) contained in the resin used for the antibacterial agent of the present invention will be discussed.

It is also possible in the antibacterial agent according to the present invention to use a repeating unit (I-b-1) as discussed in Invention I-6 or a repeating unit (I-b-2) as discussed in Invention I-7, in addition to the repeating unit (I-a), for the purpose of adjusting the content of the active component (i.e., the organic group represented by general formula (I-1)) in the antibacterial agent or adjusting the solvent solubility, applicability and mechanical properties of a resin or introducing a cross-linkable functional group. The repeating unit (I-b-1) is a repeating unit having no cross-linkable group and the repeating unit (I-b-2) is a repeating unit having a cross-linkable group.

A resin contained in the antibacterial agent of the present invention may be a polymer including a repeating unit (I-a) alone, or may be a polymer including a repeating unit (I-a) and a repeating unit (I-b-1) or a repeating unit (I-b-2).

In a case of using a multifunctional polymerizable compound such as a multifunctional acrylate and the like as a repeating unit (I-b-1), a resin is allowed to have high mechanical strength and therefore preferably adopted.

Additionally, a resin having a cross-linkable moiety such as hydroxyl group and the like at the repeating unit (I-b-1) or the repeating unit (I-b-2) is allowed to be a resin which is reacted with a curing agent such as isocyanate compound and the like to form a cross-linking structure, and allowed to have high mechanical strength. Therefore, this resin is preferably adopted.

A repeating unit (I-b-1) that the resin contained in the antibacterial agent of the present invention may have is represented by general formula (I-6).

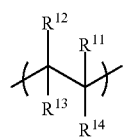

(I-6)

In this formula, $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group.

Additionally, $R^{11}$ and $R^{12}$, or $R^{13}$ and $R^{14}$ may be bonded to each other to form a ring and may contain a $C_3$-$C_{12}$ single, double or multi ring structure.

A repeating unit (I-b-2) that the resin contained in the antibacterial agent of the present invention may have is represented by general formula (I-7).

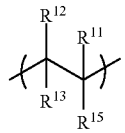

(I-7)

In this formula, $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ is characterized by being at least one group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.

As a repeating unit (I-b-2), there is adopted at least one kind of compound selected from maleic anhydride, acrylic ester, fluorine-containing acrylic ester, methacrylic ester, fluorine-containing methacrylic ester, styrene-based compound, fluorine-containing styrene-based compound, vinyl ether, fluorine-containing vinyl ether, allyl ether, fluorine-containing allyl ether, olefins, fluorine-containing olefins, norbornene compound and fluorine-containing norbornene compound.

Acrylic ester or methacrylic ester, serving as a repeating unit (I-b-2) is required only to be able to form a copolymer together with a repeating unit (I-a), a repeating unit (I-a-1), a repeating unit (I-a-2) or a repeating unit (I-a-3), and therefore usable with no particular limit on its ester side chain.

If exemplifying acrylic ester and methacrylic ester by known compounds, it is possible to cite: alkyl esters of acrylic acid or methacrylic acid, such as methyl acrylate, methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, n-hexyl acrylate, n-hexyl methacrylate, n-octyl acrylate, n-octyl methacrylate, 2-ethylhexyl acrylate, 2-ethylhexyl methacrylate, lauryl acrylate, lauryl methacrylate, 2-hydroxyethyl acrylate, 2-hydroxyethyl methacrylate, 2-hydroxypropyl acrylate, 2-hydroxypropyl methacrylate and the like; and acrylates or methacrylates containing ethylene glycol, propylene glycol or tetramethylene glycol group. It is also possible to cite unsaturated amides such as acrylamide, methacrylamide, N-methylol acrylamide, N-methylol methacrylamide, diacetone acrylamide and the like. Furthermore, it is also possible to cite vinyl silanes and acrylic or methacrylic esters containing acrylonitrile, methacrylonitrile or alkoxysilane, tert-butyl acrylate, tert-butyl methacrylate, 3-oxocyclohexyl acrylate, 3-oxocyclohexyl methacrylate, adamantyl acrylate, adamantyl methacrylate, alkyladamantyl acrylate, alkyladamantyl methacrylate, cyclohexyl acrylate, cyclohexyl methacrylate, tricyclodecanyl acrylate, tricyclodecanyl methacrylate, an acrylate or methacrylate containing a ring structure selected from a lactone ring and a norbornene ring, acrylic acid, methacrylic acid, etc. Furthermore, it is also possible to cite the above-mentioned acrylate compounds containing a cyano group at its α-position, and analogous compounds such as maleic acid, fumaric acid and maleic anhydride.

A fluorine-containing acrylic ester or a fluorine-containing methacrylic ester serving as a repeating unit (I-b-2) can be exemplified by: a monomer containing a fluorine atom or a group having fluorine atom, at α-position of acryl; an acrylic ester or a methacrylic ester which includes at its ester moiety a substituent containing fluorine atom; and a fluorine-containing compound which contains fluorine at both α-position and the ester moiety. Furthermore, a cyano group may be introduced into α-position. As a polymerizable compound having α-position into which a fluorine-containing alkyl group is introduced, there may be adopted a polymerizable compound obtained by introducing a fluorine-containing group selected from a trifluoromethyl group, trifluoroethyl group and nonafluoro-n-butyl group into α-position of the non-fluorine-containing acrylic or methacrylic ester.

On the other hand, polymerizable compounds containing fluorine at its ester moiety are polymerizable compounds that have a fluorine alkyl group (perfluoroalkyl group or fluoroalkyl group) at ester moiety or polymerizable compounds having an ester moiety where a cyclic structure and a fluorine atom are coexistent, and exemplified by acrylic or methacrylic ester which contains a unit having a fluorine-containing benzene ring, a fluorine-containing cyclopentane ring, a fluorine-containing cyclohexane ring, a fluorine-containing cycloheptane ring and the like (i.e., a unit of which cyclic structure is substituted with a fluorine atom, a trifluoromethyl group or hexafluorocarbinol group). Additionally, acrylic or methacrylic esters of which ester moiety is a fluorine-containing t-butyl ester group are also usable.

It is also possible to use a polymerizable compound obtained by combining these fluorine-containing functional groups and a fluorine-containing alkyl group of α-position. Such a polymerizable compound can be exemplified by 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, 6-[3,3,3-trifluoro-2-hydroxy-2-(trifluoromethyl)propyl]bicyclo[2.2.1]hept-2-yl acrylate, 6-[3,3,3-trifluoro-2-hydroxy-2-(trifluoromethyl)propyl]bicyclo[2.2.1]hept-2-yl 2-(trifluoromethyl)acrylate, 6-[3,3,3-trifluoro-2-hydroxy-2-(trifluoromethyl)propyl]bicyclo[2.2.1]hept-2-yl methacrylate, 1,4-bis(1,1,1,3,3,3-hexafluoro-2-hydroxyisopropyl)cyclohexyl acrylate, 1,4-bis (1,1,1,3,3,3-hexafluoro-2-hydroxyisopropyl)cyclohexyl methacrylate, and 1,4-bis(1,1,1,3,3,3-hexafluoro-2-hydroxyisopropyl)cyclohexyl 2-trifluoromethyl acrylate. Fluorine-containing polymerizable compounds are effective at improving the solvent solubility of the obtained resin and improving surface properties and water repellency, so as to be preferably adoptable as a polymerizable compound providing a repeating unit (I-b-1) which is contained in a resin and serves as an active component of an antibacterial agent of the present invention.

As a repeating unit (I-b-1), it is possible to cite a styrene-based compound and a fluorine-containing styrene-based compound, such as styrene, fluorinated styrene and hydroxystyrene. In addition, a compound to which one or a plurality of hexafluorocarbinol groups or functional groups formed by protecting the hexafluorocarbinl groups at hydroxyl group are bonded can be cited also. More specifically, it is possible to cite: styrene or hydroxystyrene where hydrogen is substituted with a fluorine atom or trifluoromethyl group; styrene having α-position to which halogen, alkyl group or a fluorine-containing alkyl group is bonded; and styrene having a perfluorovinyl group. Fluorine-containing styrene-based compounds are effective at improving solvent solubility and improving the surface properties and the water repellency of the obtained resin, similarly to fluorine-containing acrylic esters, so as to be preferably adoptable as a polymerizable compound providing a repeating unit (I-b-1) which is contained in a resin and serves as an active component of an antibacterial agent of the present invention.

As a repeating unit (I-b-1), it is possible to cite: vinyl ethers; fluorine-containing vinyl ethers; allyl ethers; fluorine-containing allyl ethers; and alkyl vinyl ethers and alkyl allyl ethers having a methyl group, ethyl group, propyl group, butyl group or a hydroxyl group selected from hydroxyethyl group and hydroxybutyl group. Additionally, it is also possible to cite: cyclic vinyls and allyl ethers having a cyclohexyl group, norbornyl group or aromatic ring and those having hydrogen or a carbonyl bond in its cyclic structure; and fluorine-containing vinyl ethers and fluorine-containing allyl ethers in which some or all hydrogen atoms of the above-mentioned functional groups are substituted with fluorine atom(s).

Moreover, a repeating unit (I-b-1) is usable with no particular limitation insofar as it is a vinyl ester, vinyl silane, olefin, a fluorine-containing olefin, a norbornene compound, a fluorine-containing norbornene compound or other compound having a polymerizable unsaturated bond.

A hydrocarbon-based olefin that serves as a repeating unit (I-b-1) can be exemplified by ethylene, propylene, isobutene, cyclopentene and cyclohexene. A fluorinated hydrocarbon-based olefin can be exemplified by vinyl fluoride, vinylidene fluoride, trifluoroethylene, chlorotrifluoroethylene, tetrafluoroethylene, hexafluoropropylene and hexafluoroisobutene.

Additionally, a norbornene compound serving as a repeating unit (I-b-1) can be exemplified by norbornene, 1-methyl norbornene, 5-methyl norbornene, 5-ethyl norbornene, 5,6-dimethyl norbornene, 7-methyl norbornene, 5,5,6-trimethyl norbornene, tricyclo[4.3.0.12.5]-3-decene, tricyclo[4.4.0.12.5]-3-undecene, tetracyclo[4.4.0.12.5.17.10]-3-dodecene, 8-methyltetracyclo[4.4.0.12.5.17.10]-3-dodecene and 8-ethyltetracyclo[4.4.0.12.5.17.10]-3-dodecene. Incidentally, the above-mentioned polymerizable compounds may be used singly or in combination of two or more kinds.

As a repeating unit (I-b-2), it is particularly preferable to use the following polymerizable compounds.

It is possible to cite the following multifunctional polymerizable compounds including 2-hydroxyethyl acrylate, hydroxypropyl acrylate, 4-hydroxybutyl acrylate, 3-(trimethoxysilyl)propyl acrylate, 3-chloro-2-hydroxypropyl methacrylate, ethyl 2-(hydroxymethyl)acrylate, 2-hydroxyethyl methacrylate, hydroxypropyl methacrylate, 3-(trimethoxysilyl)propyl methacrylate, 3-[tris(trimethylsilyloxy)silyl]propyl methacrylate, 2-(trimethylsilyloxy)ethyl methacrylate, 2-(triethoxysilyl)propyl methacrylate, allytriethoxysilane, allytrimethoxysilane, 3-(acryloxy)propyltrimethoxysilane, [bicycle[2.2.1]hept-5-en-2-yl]triethoxysilane, vinyltrimethoxysilane, triethoxyvinylsilane, vinyltris(2-methoxyethoxy)silane, N-[2-(N-vinylbenzylamino)ethyl]-3-aminopropyltrimethoxysilane hydrochloride, allytrichlorosilane, trichlorovinylsilane, 3-methyl-1-penten-4-yn-3-ol, 2-(furfurylthio)ethylamine, trans-aconitic acid, acrylic acid, 4-aminocinnamic acid, angelic acid, 2-acetamideacrylic acid, 3-butene-1,2,3-tricarboxylic acid, 2-bromocinnamic acid, 2-benzylacrylic acid, caffeic acid, 4-chlorocinnamic acid, trans-cinnamic acid, citraconic acid, trans-p-coumaric acid, trans-o-coumaric acid, trans-m-coumaric acid, crotonic acid, α-cyanocinnamic acid, 1-cyclohexene-1-carboxylic acid, 1-cyclopentenecarboxylic acid, α-cyano-4-hydroxycinnamic acid, traumatic acid, trans-2-decenoic acid, 3,4-dimethoxycinnamic acid, trans-2,3-dimethoxycinnamic acid, trans-2,5-dichlorocinamic acid, fumaric acid, monoethyl fumarate, trans-2-hexenoic acid, 2-heptenoic acid, monoethyl itaconate, monoamide maleate, mesaconic acid, methacrylic acid, 4-methyl-2-pentenoic acid, trans, trans-muconic acid, mucobromic acid, mucochloric acid, 3-methylcrotonic acid, 4-methoxycinnamic acid, mono(2-acryloyloxyethyl) succinate, 3-(5-nitro-2-furyl)acrylic acid, 3-(3-pyridyl)crylic acid, α-phenylcinnamic acid, shikimic acid, tiglic acid, 2-thiopheneacrylic acid, 2-(trifluoromethyl)acrylic acid, 3-(trifluoromethyl)cinnamic acid, 4-(trifluoromethyl)cinnamic acid, 2-(trifluoromethyl)cinnamic acid, allyl mercaptan, allyl glycidyl ether, 1,3-butadiene monoepoxide, 1,2-epoxy-5-hexene, 1,2-epoxy-9-decene, allobarbital, 1,9-decadiene, 1,11-dodecadiene, dicyclopentadiene, 2,3-dimethyl-1,3-butadiene, diethyl diallylmalonate, 1,3-dibenzylidene-2-cyclohexanone, 2,6-dimethyl-2,4,6-octatriene, 1,5,9-decatriene, 9,10-epoxy-1,5-cyclododecadiene, farnesyl acetate, geranyl-linalool, geranyl nitrile, 1,5-hexadiene, 1,4-hexadiene, 1,5-hexadiene-3,4-diol, isoprene, (±)-limonene, myrcene, methylcyclopentadiene, 2,5-norbornadiene, 1,7-octadiene, monoethyl fumarate, ethyl hydrogen maleate, monooctyl maleate, monomethyl maleate, monoisopropyl fumarate, mono(2-acryloyloxyethyl) succinate, 6-acrylamide hexanoic acid, acrylamide, allylamine, 1-allyl-2-thiourea, 1-allyl-3-(2-hydroxyethyl)-2-thiourea, allylurea, methyl 3-aminocrotonate, 3-amino-5,5-dimethyl-2-cyclohexen-1-one, S-allyl-L-cysteine, ethyl 3-amino-4,4,4-trifluorocrotonate, 3-amino-2-cyclohexen-1-one, 3-benzalbutyramide, crotonamide, cinnamamide, 2-(1-cyclohexenyl)ethylamine, glycidyl methacrylate and polyethylene glycol diacrylate.

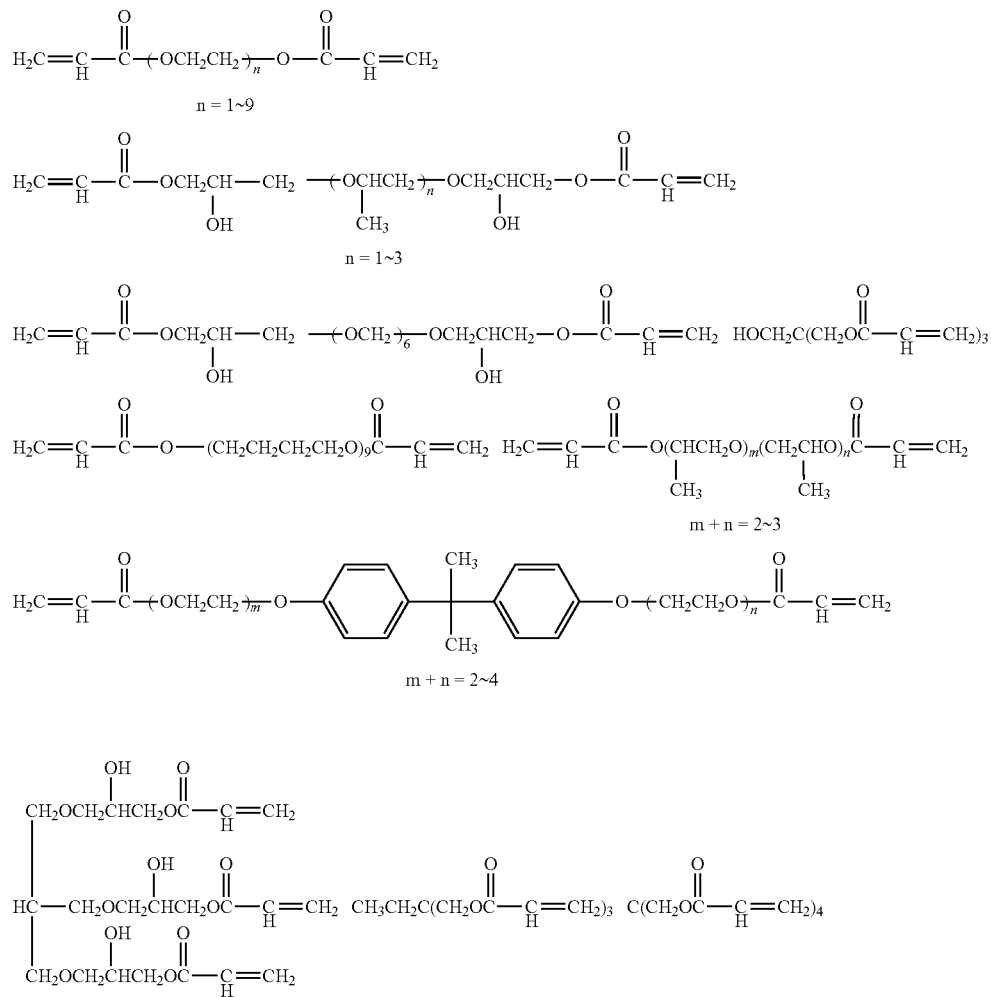

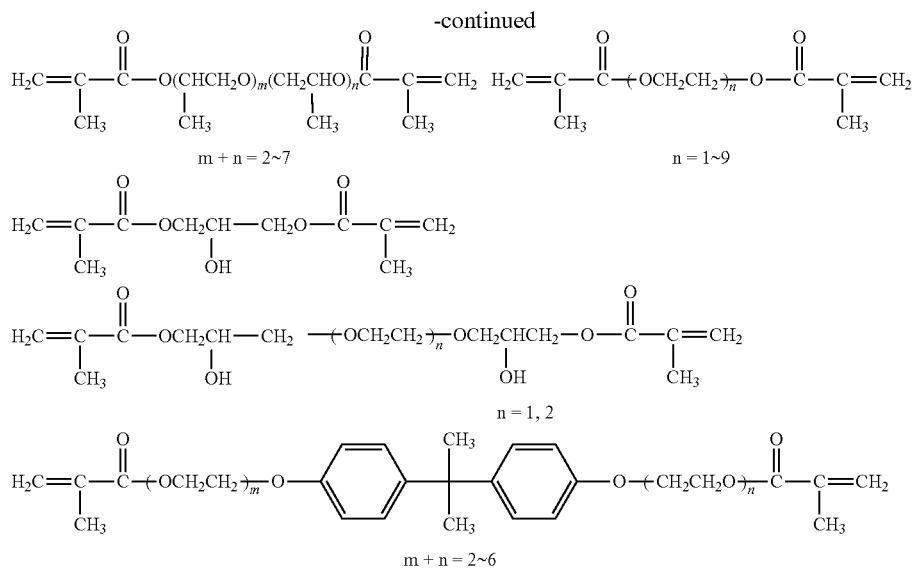

In particular, polyethylene glycol diacrylate, styrene, 2,3,4,5,6-pentafluorostyrene, 2-hydroxyethyl methacrylate, acrylonitrile, 2-norbornene and the like are preferably usable.

4. Cross-Linking Agent

A cross-linking agent will be discussed.

In the present invention, it is possible to use a cross-linking agent reactive with a functional group such as hydroxyl group, mercapto group, carboxyl group, amino group, epoxy group, alkenyl group, alkynyl group, acryloyl group, methacryloyl group, chlorosilyl group, alkoxysilyl group, hydrosilyl group and the like, for the purpose of improving the durability of an antibacterial agent.

The cross-linking agent is exemplified by isocyanate compounds, epoxy compounds, aldehyde-based compounds, chlorosilanes, alkoxysilanes, melamine-based compounds, sulfur and sulfur compounds. Of these compounds, multifunctional compounds are preferably adopted from the fact that when a resin serving as an active component of an antibacterial agent of the present invention is synthesized it becomes possible to increase the cross-linking density of the resin and the fact that a resin excellent in mechanical strength can be obtained.

In synthesizing a resin that serves as an active component of an antibacterial agent of the present invention, it is possible to employ a resin synthesis method where a peroxide compound or azo compound is used as a cross-linking agent and cross-linking is initiated by free-radical reaction. In that the resin is obtained to have durability, this method is particularly preferably adopted for the antibacterial agent of the present invention.

An isocyanate compound to be used as a cross-linking agent when synthesizing a resin that serves as an active component of an antibacterial agent of the present invention and reacted with hydroxyl group, amino group or the like to form a cross-linking structure in the resin is exemplified by diisocyanate compounds such as 1,4-phenylene diisocyanate, 4,4'-diphenylmethane diisocyanate, 3,3'-dichlorobiphenyl-4,4'-diisocyanate, dicyclohexylmethane-4,4'-diisocyanate, hexamethylene diisocyanate, m-xylylene diisocyanate, trilene-2,6-diisocyanate, trimethyl hexamethylene diisocyanate, naphthalene diisocyanate, isophorone diisocyanate and the like. Additionally, it is also possible to cite the above-mentioned diisocyanate compounds in the form of an uretidinedione-type dimer, a biuret-type trimer or an isocyanurate-type trimer, adducts of polyol such as 1,3-propanediol, trimethylol propane and the like. Furthermore, it is also possible to cite triisocyanates such as triphenylmethane isocyanate and tris(isocyanatephenyl)thiophosphate, and the like.

In synthesizing a resin that serves as an active component of an antibacterial agent of the present invention, hexamethylene diisocyanate is particularly preferably employed since it exhibits stability as a compound and the resin is obtained to have flexibility.

An epoxy compound to be used as a cross-linking agent when synthesizing a resin that serves as an active component of an antibacterial agent of the present invention and reacted with carboxyl group or the like to form a cross-linking structure is exemplified by glycidyl ether-based compounds, glycidyl ester-based compounds, glycidyl amine-based compounds, alicyclic compounds and the like. For example, it is possible to cite 1,4-butanediol diglycidyl ether, 2,2-bis(4-glycidyloxyphenyl)propane, diglycidyl 1,2-cyclohexanedicarboxylate, 1,7-octadiene diepoxide, 1,5-hexadiene diepoxide, triglycidyl isocyanurate, neopentyl glycol diglycidyl ether, 1,3-butadiene monoepoxide, 1,2-epoxy-5-hexene, 1,2-epoxy-9-decene and the like. In synthesizing a resin that serves as an active component of an antibacterial agent of the present invention, 1,4-butanediol diglycidyl ether is particularly preferably employed since it has a moderate reactivity.

An aldehyde-based compound to be used as a cross-linking agent when synthesizing a resin that serves as an active component of an antibacterial agent of the present invention and reacted with phenolic hydroxyl group or the like to form a cross-linking structure is exemplified by formaldehyde, formalin, paraformaldehyde, trioxane, acetaldehyde, polyoxymethylene and propionaldehyde. In synthesizing a resin that serves as an active component of an antibacterial agent of the present invention, paraformaldehyde is particularly preferably employed since it has a moderate reactivity and easy to handle.

Chlorosilanes to be used as a cross-linking agent when synthesizing a resin that serves as an active component of an antibacterial agent of the present invention and useful for the cross-linking reaction that forms siloxane bonds is exemplified by dimethyldichlorosilane, diethyldichlorosilane, diphenyldichlorosilane, divinyldichlorosilane, methyldichlorosilane, ethyldichlorosilane, phenyldichlorosilane, vinyldichlorosilane, dichlorosilane, methyltrichlorosilane, ethyltrichlorosilane, phenyltrichlorosilane, vinyltrichlorosilane, trichlorosilane, tetrachlorosilane, 1,2-bis(trichlorosilyl)ethane, bis(trichlorosilyl)acetylene, 3-chloropropyltrichlorosilane, cyclohexyltrichlorosilane, trichloro(1H,1H,2H,2H-tridecafluoro-n-octyl)silane, trichloro-2-cyanoethylsilane, phenyltrichlorosilane and the like. In synthesizing a resin that serves as an active component of an antibacterial agent of the present invention, dimethyldichlorosilane is particularly preferably employed since it is well reactive, inexpensive and easily available.

Alkoxysilanes to be used as a cross-linking agent when synthesizing a resin that serves as an active component of an antibacterial agent of the present invention and useful for the cross-linking reaction that forms siloxane bonds is exemplified by dimethyldimethoxysilane, diethyldimethoxysilane, diphenyldimethoxysilane, divinyldimethoxysilane, methyldimethoxysilane, ethyldimethoxysilane, phenyldimethoxysilane, vinyldimethoxysilane, dimethoxysilane, methyltrimethoxysilane, ethyltrimethoxysilane, phenyltrimethoxysilane, vinyltrimethoxysilane, trimethoxysilane, tetramethoxysilane, dimethyldiethoxysilane, diethyldiethoxysilane, diphenyldiethoxysilane, divinyldiethoxysilane, methyldiethoxysilane, ethyldiethoxysilane, phenyldiethoxysilane, vinyldiethoxysilane, diethoxysilane, methyltriethoxysilane, ethyltriethoxysilane, phenyltriethoxysilane, vinyltriethoxysilane, triethoxysilane, tetraethoxysilane, 3-aminopropyltriethoxysilane, 3-(2-aminoethylamino)propyltrimethoxysilane, 3-(2-aminoethylamino)propyltriethoxysilane, bis[3-(trimethoxysilyl)propyl]amine, 1,2-bis(trimethoxysilyl)ethane, benzyltriethoxysilane, (3-bromopropyl)trimethoxysilane, 3-trimethoxysilylpropyl chloride, 2-cyanoethyltriethoxysilane, (chloromethyl)triethoxysilane, cyclohexyltrimethoxysilane, 2-(3,4-epoxycyclohexyl)ethyltrimethoxysilane, 3-glycidyloxypropyltrimethoxysilane, (3-mercaptopropyl)trimethoxysilane, (3-mercaptopropyl)triethoxysilane, 1,1,1-trifluoro-3-(trimethoxysilyl)propane, triethoxyphenylsilane, trimethoxyphenylsilane, trimethoxy(4-methoxyphenyl)silane and trimethoxy(p-tolyl)silane. In synthesizing a resin that serves as an active component of an antibacterial agent of the present invention, dimethyldimethoxysilane is particularly preferably employed since it is well reactive, inexpensive and easily available.

Melamine-based compounds to be used as a cross-linking agent when synthesizing a resin that serves as an active component of an antibacterial agent of the present invention and reacted with hydroxyl group or the like to form a cross-linking structure is exemplified by melamine, methylolated melamine, and a methylolated melamine derivative. Furthermore, it is also possible to use a compound partially or entirely etherified by reacting methylolated melamine with a lower alcohol. Additionally, the melamine-based compounds may be either a monomer or a polymer (having two or more monomers), and may be a combination of these.

In synthesizing a resin that serves as an active component of an antibacterial agent of the present invention, methylolated melamine and a derivative thereof are particularly preferably employed since these have good reactivity and easy to handle.

Sulfur or a sulfur compound to be used as a cross-linking agent when synthesizing a resin that serves as an active component of an antibacterial agent of the present invention and reacted with alkenyl group, alkynyl group, acryloyl group, methacryloyl group or the like to form a cross-linking structure is exemplified by sulfur, tetramethylthiuram disulfide, tetraethylthiuram disulfide, tetrabutylthiuram disulfide, tetrakis(2-ethylhexyl)thiuram disulfide, dipentamethylenethiuram tetrasulfide, morpholine disulfide, 2-(4'-morpholinodithio)benzothiazol and the like.

In synthesizing a resin that serves as an active component of an antibacterial agent of the present invention, sulfur is particularly preferably employed since it is inexpensive and easy to handle.

A peroxide compound to be used as a cross-linking agent when synthesizing a resin that serves as an active component of an antibacterial agent of the present invention and useful for cross-linking initiated by free-radical reaction (i.e., a radical reaction forming alkyl group and the like) is exemplified by benzoyl peroxide, dichlorobenzoyl peroxide, dicumyl peroxide, di-tert-butyl peroxide, 2,5-dimethyl-2,5-di(peroxybenzoate)hexyne-3,1,4-bis(tert-butylperoxyisopropyl)benzene, lauroyl peroxide, tert-butyl peracetate, 2,5-dimethyl-2,5-di(tert-butylperoxy)hexyne-3,2,5-trimethyl-2,5-di(tert-butylperoxy)hexane, tert-butyl perbenzoate, tert-butyl perphenylacetate, tert-butyl perisobutylate, tert-butyl per-sec-octoate, tert-butyl peroxypivalate, cumyl perpivalate, and tert-butyl perdiethylacetate.

In synthesizing a resin that serves as an active component of an antibacterial agent of the present invention, benzoyl peroxide is particularly preferably employed since it has a good reactivity and the resin is obtained to have great mechanical properties.

An azo compound to be used as a cross-linking agent when synthesizing a resin that serves as an active component of an antibacterial agent of the present invention and useful for cross-linking initiated by free-radical reaction (i.e., a radical reaction forming alkyl group and the like) is exemplified by azobisisobutyronitrile and dimethyl azoisobutyrate.

In synthesizing a resin that serves as an active component of an antibacterial agent of the present invention, azobisisobutyronitrile is particularly preferably employed since it is low-cost and easy to handle.

These cross-linking agents may be used singly or in combination by selecting two or more. It is also possible to adjust the cure rate, the pot life and the properties of a resin to be obtained suitably according to the kind or the amount of the cross-linking agent to be used.

5. Polymerization Method

Hereinafter, a method for providing a resin that serves as an active component of an antibacterial agent of the present invention with a repeating unit (I-a), a repeating unit (I-a-1), a repeating unit (I-a-2) or a repeating unit (I-a-3), and more specifically, a polymerization method for polymerizing a polymerizable compound (i.e., a precursor of the above-mentioned repeating units) singly to obtain a resin will be discussed. In addition, there will be discussed also a polymerization method of copolymerizing the polymerizable compound providing a resin that serves as an active component of an antibacterial agent of the present invention with a repeating unit (I-a-1), a repeating unit (I-a-2) or a repeating unit (I-a-3) (i.e., a precursor of the above-mentioned repeating units) with a polymerizable compound providing a repeating unit (I-b-1) or a repeating unit (I-b-2) or serving as a precursor of these repeating units to obtain a resin.

A polymerization method is exemplified by radical polymerization and a polymerization using a transition metal.

First of all, radical polymerization will be explained.

A polymerization method for obtaining a resin that serves as an active component of an antibacterial agent of the present invention is not particularly limited insofar as the method is a generally usable one, but radical polymerization and ionic polymerization are preferable. It is also possible to employ coordination anionic polymerization, living anionic polymerization, cationic polymerization, ring-opening metathesis polymerization or vinylene polymerization.

Radical polymerization is conducted according to a known polymerization method selected from bulk polymerization, solution polymerization, suspension polymerization and emulsion polymerization in the presence of a radical polymerization initiator or a radical initiating source, with a batch-wise, semi-continuous or continuous operation.

The radical polymerization initiator is not particularly limited but exemplified by azo compounds, peroxide compounds and redox compounds. In order to synthesize a resin that serves as an active component of an antibacterial agent of the present invention, azobisisobutyronitrile, t-butylperoxypivalate, di-t-butylperoxide, i-butyrylperoxide, lauroyl peroxide, succinic acid peroxide, dicinnamylperoxide, di-n-propylperoxydicarbonate, t-butylperoxyallyl monocarbonate, benzoyl peroxide, hydrogen peroxide, and ammonium persulfate are preferably used to a polymerization reaction for obtaining a resin that serves as an active component of an antibacterial agent of the present invention.

In polymerization reaction for obtaining a resin that serves as an active component of an antibacterial agent of the present invention, a reaction vessel used for the polymerization reaction is not particularly limited. Additionally, a polymerization solvent may be used in the polymerization reaction. As the polymerization solvent used in the polymerization reaction for obtaining a resin that serves as an active component of an antibacterial agent of the present invention, one that does not interfere with radical polymerization is preferable, and usable examples thereof are: ester-based ones selected from ethyl acetate and n-butyl acetate; ketone-based ones selected from acetone and methyl isobutyl ketone; hydrocarbon-based ones selected from toluene and cyclohexane; and alcohol-based solvents selected from methanol, isopropyl alcohol, methyl isobutyl carbinol and ethylene glycol monomethyl ether. Additionally, it is also possible to use various types of solvents selected from water, ether-based ones, cyclic ether-based ones, fluorohydrocarbon-based ones and aromatic ones. These solvents may be used singly or in combination of not less than two kinds of them. Additionally, a molecular weight adjusting agent such as mercaptan may be used together therewith. In the polymerization reaction for obtaining a resin that serves as an active component of an antibacterial agent of the present invention, the reaction temperature in a copolymerization reaction is suitably changed according to the radical polymerization initiator or radical polymerization initiating source, and is preferably within a range of not lower than 20° C. and not higher than 200° C. in general, particularly preferably within a range of not lower than 30° C. and not higher than 140° C.

Then, a polymerization using a transition metal will be discussed.

Ring-opening metathesis polymerization is required only to use a transition metal catalyst of the group IV, V, VI or VII in the presence of a co-catalyst and to use a known method in the presence of a solvent. The transition metal catalyst is not particularly limited and exemplified by Ti-based, V-based, Mo-based and W-based catalysts. In particular, titanium(IV) chloride, vanadium(IV) chloride, vanadium trisacetylacetonate, vanadium bisacetylacetonatedichloride, molybdenum (VI) chloride and tungsten(VI) chloride are preferable in the polymerization reaction for obtaining a resin that serves as an active component of an antibacterial agent of the present invention. The amount of the catalyst is not lower than 0.001 mol % and not higher than 10 mol %, preferably not lower than 0.01 mol % and not higher than 1 mol % relative to the used monomer.

As a co-catalyst, it is possible to cite alkylaluminium and alkyltin. In particular, it is possible to cite: aluminium-based ones represented by trialkylaluminiums selected from trimethylaluminium, triethylaluminium, tripropylaluminium, triisopropylaluminium, triisobutylaluminium, tri-2-methylbutylaluminium, tri-3-methylbutylaluminium, tri-2-methylpentylaluminium, tri-3-methylpentylaluminium, tri-4-methylpentylaluminium, tri-2-methylhexylaluminium, tri-3-methylhexylaluminium and trioctylaluminium, dialkylaluminium halides selected from dimethylaluminium chloride, diethylaluminium chloride, diisopropylaluminium chloride and diisobutylaluminium chloride, monoalkylaluminium halides selected from methylaluminium dichloride, ethylaluminium dichloride, ethylaluminium diiodide, propylaluminium dichloride, isopropylaluminium dichloride, butylaluminium dichloride and isobutylaluminium dichloride, and alkylaluminium sesquichlorides selected from methylaluminium sesquichloride, ethylaluminium sesquichloride, propylaluminium sesquichloride and isobutylaluminium sesquichloride; tetra-n-butyltin; tetraphenyltin; and triphenylchlorotin. The amount of the co-catalyst to be used is within a range of 100 equivalents or less, preferably 30 equivalents or less by molar ratio relative to the transition metal catalyst.

A polymerization solvent will do unless it interferes with the polymerization reaction, and representative examples thereof are: aromatic hydrocarbon-based ones selected from benzene, toluene, xylene, chlorobenzene and dichlorobenzene; hydrocarbon-based ones selected from hexane, heptane and cyclohexane; and halogenated hydrocarbons selected from carbon tetrachloride, chloroform, methylene chloride and 1,2-dichloroethane. In the polymerization reaction for obtaining a resin that serves as an active component of an antibacterial agent of the present invention, these polymerization solvents may be used singly or in combination of two or more kinds. The reaction temperature is preferably not lower than −70° C. and not higher than 200° C. in general, particularly preferably not lower than −30° C. and not higher than 60° C.

Vinylene polymerization is required only to use a transition metal catalyst of the group VIII such as iron, nickel, rhodium, palladium, platinum and the like, or a metal catalyst of the groups IVB to VIB selected from zirconium, titanium, vanadium, chromium, molybdenum and tungsten in the presence of a co-catalyst, and to adopt a known method in the presence of a solvent. The polymerization catalyst is not particularly limited but, in the polymerization reaction for obtaining a resin that serves as an active component of an antibacterial agent of the present invention, it is particularly preferable to use: transition metal compounds of the group VIII, selected from iron(II) chloride, iron(III) chloride, iron(II) bromide, iron(III) bromide, iron(II) acetate, iron(III) acetylacetonate, ferrocene, nickelocene, nickel(II) acetate, nickel bromide, nickel chloride, dichlorohexylnickel acetate, nickel lactate, nickel oxide, nickel tetrafluoroborate, bis(allyl)nickel, bis(cyclopentadienyl)nickel, nickel(II) hexafluoroacetylacetonatetetrahydrate, nickel(II) trifluoroacetylacetonatedihydrate, nickel(II) acetylacetonatetetrahydrate, rhodium(III) chloride, rhodium tris(triphenylphosphine)trichloride, palladium(II) bis(trifluoroacetate), palladium(II) bis(acetylacetonate), palladium(II) 2-ethylhexanoate, palladium(II) bromide, palladium(II) chloride, palladium(II) iodide, palladium (II) oxide, monoacetonitriletris(triphenylphosphine) palladium(II) tetrafluoroborate, tetrakis(acetonitrile)

palladium(II) tetrafluoroborate, dichlorobis(acetonitrile)palladium(II), dichlorobis(triphenylphosphine)palladium (II), dichlorobis(benzonitrile)palladium(II), palladium acetylacetonate, palladium bis(acetonitrile)dichloride, palladium bis(dimethylsulfoxide)dichloride and platinum bis(triethylphosphine)hydrobromide; and transition metal compounds of the groups IVB to VIB, selected from vanadium (IV) chloride, vanadium trisacetylacetonate, vanadium bisacetylacetonatedichloride, trimethoxy(pentamethylcyclopentadienyl)titanium(IV), bis(cyclopentadienyl)titanium dichloride and bis(cyclopentadienyl)zirconium dichloride. The amount of the catalyst is not lower than 0.001 mol % and not higher than 10 mol %, preferably not lower than 0.01 mol % and not higher than 1 mol % relative to the used monomer. The co-catalyst is exemplified by alkylaluminoxane and alkylaluminium, and in the polymerization reaction for obtaining a resin that serves as an active component of an antibacterial agent of the present invention, it is possible to particularly cite: methylaluminoxane (MAO); trialkylaluminiums such as trimethylaluminium, triethylaluminium, tripropylaluminium, triisopropylaluminium, triisobutylaluminium, tri-2-methylbutylaluminium, tri-3-methylbutylaluminium, tri-2-methylpentylaluminium, tri-3-methylpentylaluminium, tri-4-methylpentylaluminium, tri-2-methylhexylaluminium, tri-3-methylhexylaluminium, trioctylaluminium and the like; dialkylaluminium halides selected from dimethylaluminium chloride, diethylaluminium chloride, diisopropylaluminium chloride and diisobutylaluminium chloride; monoalkylaluminium halides selected from methylaluminium dichloride, ethylaluminium dichloride, ethylaluminium diiodide, propylaluminium dichloride, isopropylaluminium dichloride, butylaluminium dichloride and isobutylaluminium dichloride; and alkylaluminium sesquichlorides selected from methylaluminium sesquichloride, ethylaluminium sesquichloride, propylaluminium sesquichloride and isobutylaluminium sesquichloride. In the case of methylaluminoxane, the amount of the co-catalyst is not lower than 50 equivalents and not higher than 500 equivalents in terms of Al conversion. In the case of other alkylaluminiums, the amount of the co-catalyst is within a range of 100 equivalents or less, preferably 30 equivalents or less by molar ratio relative to the transition metal catalyst. Additionally, the polymerization solvent will do unless it interferes with the polymerization reaction, and representative examples thereof are aromatic hydrocarbon-based ones selected from benzene, toluene, xylene, chlorobenzene and dichlorobenzene, hydrocarbon-based ones selected from hexane, heptane and cyclohexane, halogenated hydrocarbon-based ones selected from carbon tetrachloride, chloroform, methylene chloride and 1,2-dichloroethane, dimethylformamide, N-methylpyrolidone and N-cyclohexylpyrolidone. These polymerization solvents may be used singly or in combination of two or more kinds. The reaction temperature is preferably not lower than −70° C. and not higher than 200° C. in general, particularly preferably not lower than −40° C. and not higher than 80° C.

As a method of removing a medium such as an organic solvent and water from the thus obtained solution or dispersion liquid (of a resin that serves as an active component of an antibacterial agent of the present invention), any known method can be used. For example, it is possible to cite methods such as reprecipitation, filtration, heating distillation under reduced pressure and the like.

6. Substrate Surface Treatment Method

It is possible to conduct a substrate surface treatment in such a manner as to coat a target substrate with a resin that serves as an active component of an antibacterial agent of the present invention. It is possible to dissolve a resin that has previously been obtained by polymerization reaction in a solvent and then apply it to a substrate and then dry it to form a film. Additionally, it is also possible to use a curing agent in such a manner as to mix at the time of application to improve the strength of the film, which is preferably adopted in coating a resin that serves as an active component of an antibacterial agent of the present invention.

Furthermore, it is also possible to cure a film by applying a polymerizable compound or a polymerizable compound with which a curing agent is mixed to a substrate and then reacting it with heat, light or a catalyst. Application with no solvent is also possible, which is especially effective at improving the fabrication environment.

A solvent in which a resin that serves as an active component of an antibacterial agent of the present invention is dissolved is not particularly limited insofar as the resin is soluble therein, and usable ones are ketones selected from acetone, methyl ethyl ketone, cyclohexanone, methyl isoamyl ketone and 2-heptanone, polyalcohols selected from ethylene glycol, ethylene glycol monoacetate, diethylene glycol, diethylene glycol monoacetate, propylene glycol, propylene glycol monoacetate, dipropylene glycol, dipropylene glycol monoacetate, monomethyl ether, monoethyl ether, monopropyl ether, monobutyl ether and monophenyl ether, monovalent alcohols selected from methanol, ethanol, isopropyl alcohol and methyl isobutyl carbinol and derivatives of these, cyclic ethers such as dioxane, esters selected from methyl lactate, ethyl lactate, methyl acetate, ethyl acetate, butyl acetate, methyl pyruvate, ethyl pyruvate, methyl methoxypropionate and ethyl ethoxypropionate, aromatic solvents selected from xylene and toluene, fluorine-based solvents selected from chlorofluorocarbons, alternative chlorofluorocarbons, perfluoro compounds and hexafluoroisopropyl alcohol, and terpene-based petroleum naphtha solvents and paraffinic solvents serving as high-boiling-point weak solvents for the purpose of increasing the application properties. These may be used singly or in combination of two or more kinds.

In the present invention, an antibacterial agent containing as an active component a resin having a bismethide acid group as discussed in Invention I-1, and an antibacterial agent containing as an active component a resin where a bismethide acid group is bonded to a specific polymer chain as discussed in Inventions I-2 to I-8 are applied to a substrate surface, thereby forming a film.

More specifically, the present invention is a substrate surface treatment method characterized by applying an antibacterial agent as discussed in any of Inventions I-2 to I-8 to a substrate surface thereby forming a film.

In addition to a polymerizable compound providing a repeating unit (I-a) of Invention I-2, a repeating unit (I-a-1) of Invention I-3, a repeating unit (I-a-2) of Invention I-4 or a repeating unit (I-a-3) of Invention I-5, it is possible to add a polymerizable compound providing a repeating unit (I-b-1) of Invention I-6 or a repeating unit (I-b-2) of Invention I-7, and it is also possible to add a cross-linking agent of Invention I-8.

There was prepared a multifunctional polymerizable compound having two or more polymerizable double bonds, for synthesizing a resin that serves as an active component of an antibacterial agent of Inventions I-1 to I-8. More specifically, there were prepared a polymerizable compound providing a repeating unit (I-a) that has a bismethide acid group as discussed in Inventions I-2 to I-5 and a polymerizable compound providing a repeating unit (I-b-1) of Invention I-6 or a repeating unit (I-b-2) of Invention I-7. These compounds were polymerized after being applied directly to a glass substrate with no solvent by a bar coater, spraying, spin coating or the like or after being applied to a glass substrate in the form of a solution containing these compounds by a bar coater, spraying, spin coating or the like, thereby obtaining a film of a colorless and transparent antibacterial agent of the present invention (i.e., an antibacterial film).

According to compound, it is possible to apply it directly to a substrate surface with no solvent and therefore a drying step is not necessary after polymerization, contrary to a case where a compound is made into a solution by using a solvent. It is therefore preferable to obtain a film with no solvent.

Incidentally, at the time of applying a solution, it is preferable to use as the solvent a solvent usable for polymerization. In this case, there can be employed an ester-based solvent such as ethyl acetate, n-butyl acetate and the like, a ketone-based solvent such as acetone, methyl isobutyl ketone, cyclohexanone and the like, a hydrocarbon-based solvent such as n-hexane, n-heptane and the like, an alcohol-based solvent such as methanol, isopropyl alcohol, ethylene glycol monomethyl ether and the like, water, an ether-based solvent, a cyclic ether-based solvent, a chlorofluorocarbon-based solvent, and aromatic solvent such as toluene, xylene and the like. These solvents may be used singly or in combination of two or more kinds, as a polymerization solvent.

An initiator for radical polymerization reaction is exemplified by azo compounds, peroxide compounds and redox compounds. It is particularly preferable to use azobisisobutyronitrile, tert-butyl peroxypivalate, di-tert-butylperoxide, i-butyrylperoxide, lauroyl peroxide, succinic acid peroxide, dicinnamylperoxide, di-n-propylperoxydicarbonate, tert-butylperoxyallyl monocarbonate, benzoyl peroxide, hydrogen peroxide, and ammonium persulfate. In view of availability and good reactivity, t-butylperoxypivalate is particularly preferably used in the present invention.

In order to initiate radical polymerization reaction, a photopolymerization initiator may be used. It is preferable to use alkylphenones such as 2,2-dimethoxy-1,2-diphenylethan-1-one, 1-hydroxycyclohexyl phenyl ketone, 2-hydroxy-2-methyl-1-phenylpropan-1-one, 1-[4-(2-hydroxyethoxyl)phenyl]-2-hydroxy-2-methyl-1-propan-1-one, 2-hydroxy-1-{4-[4-(2-hydroxy-2-methylpropionyl)benzyl]phenyl}-2-methylpropan-1-one, 2-methyl-1-(4-methylphenyl)-2-morpholinopropan-1-one, 2-benzyl-2-dimethylamino-1-(4-morpholinophenyl)butanone-1,2,-(dimethylamino)-2-[(4-methylphenyl)methyl]-1-[4-(4-morpholinyl)phenyl]-1-butanone and oligo{2-hydroxy-2-methyl-[4-(1-methylvinyl) phenyl]}propanone, and acylphosphone oxides such as 2,4,6-trimethylbenzoylphenylphosphineoxide and bis(2,4,6-trimethylbenzoyl)phenylphosphineoxide. As the photopolymerization initiator, it is particularly preferable to use 1-hydroxycyclohexyl phenyl ketone in view of its availability and good reactivity.

The reaction temperature for polymerization differs according to the kind of an initiator to be used. In the case of using a thermal polymerization initiator, the temperature is preferably not lower than 50° C. and not higher than 150° C. in general, particularly preferably from 80° C. to 120° C. in terms of handling.

Meanwhile, in the case of using a photopolymerization initiator, it is possible to initiate radical polymerization on a substrate relatively low in heat resistance, such as a PET film. The substrate is irradiated with a high-pressure mercury lamp for 10 minutes under a condition of about 10 mW/cm² thereby accomplishing photo-curing. The reaction temperature for the polymerization reaction is preferably not lower than 0° C. and not higher than 100° C. in general, particularly preferably not lower than 20° C. and not higher than 50° C. in terms of handling.

A substrate which can be subjected to application is exemplified by glass, plastic, metal and the like, and more specifically electrical components, electronic appliances, building materials, craft products, apparel industrial products, medical supplies and the like.

It is possible to immerse an antibacterial resin in an aqueous solution of hydrochloric acid or sulfuric acid as necessary thereby rinsing it with ion exchange water.

Moreover, it is also possible to impregnate a porous film with a raw material solution containing a polymerizable compound and a cross-linkable compound or to mix a filler such as nano-silica particles, glass fibers and the like in the raw material solution to enhance the mechanical strength of an antibacterial resin.

The thickness of an antibacterial resin is not particularly limited but it is preferably not smaller than 20 nm and not larger than 1 mm. It is difficult to apply the resin to have a thickness of smaller than 20 nm, and it is not necessary to make the thickness larger than 1 mm. The film thickness is adjusted by the thickness of application to a substrate, i.e., application quantity per unit area.

<Mode(s) for Carrying Out Invention "II">

1. Antibacterial Agent Composition

An antibacterial agent composition according to the present invention will be discussed.

[Invention II-1]

An antibacterial agent composition including a fluorine-containing polymerizable compound represented by general formula (II-1).

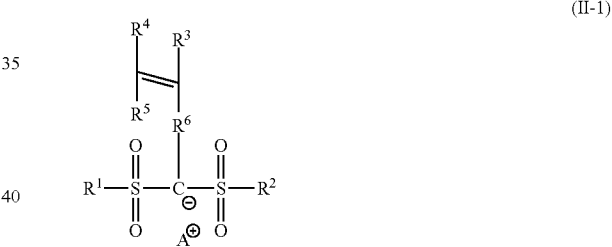

(II-1)

(In the formula (II-1), $R^1$ and $R^2$ mutually independently represent a $C_1$-$C_4$ fluoroalkyl group. $R^3$ represents a hydrogen atom, a $C_1$-$C_4$ alkyl group, a halogen atom or a $C_1$-$C_4$ fluoroalkyl group. $R^4$ and $R^5$ mutually independently represent a hydrogen atom, a $C_1$-$C_4$ alkyl group or a halogen atom. $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with fluorine atom or hydroxyl group. $R^3$ and $R^4$, or $R^5$ and $R^6$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

A cation to be bonded to "C" may be either a monovalent cation or a polyvalent cation. As the above-mentioned monovalent cation, it is possible to cite hydrogen ion ($H^+$), lithium ion ($Li^+$), sodium ion ($Na^+$), potassium ion ($K^+$), silver ion ($Ag^+$), copper(II) ion ($Cu^+$), mercury(II) ion ($Hg^+$), ammonium ion ($NH_4^+$), alkylammonium ion, anilinium ion, phenylammonium ion, pyridinium ion, pyrimidinium ion, pyrazolium ion, imidazolium ion, benzimidazolium ion, triazinium ion, hexahydro triazinium ion, triazolium ion, isoxazolium ion, thiazolium ion, isothiazolium ion, pyrrolium ion, benzthiazolium ion, thiazolin-2-onium ion, isothiazolin-3-onium ion, benzoisothiazolin-3-onium ion, benzothiazolin-2-onium ion, tetrahydro thiadiazine-2-thionium ion and the like.

Moreover, an alkylammonium ion can be exemplified by monoalkylammonium ion ($NRH_3^+$), dialkylammonium ion ($NR_2H_2^+$), trialkylammonium ion ($NR_3H^+$), tetraalkylammonium ion ($NR_4^+$) and the like. Furthermore, trialkylammonium ion can be exemplified by trimethylammonium ion ($N(CH_3)_3H^+$), triethylammonium ion ($N(C_2H_5)_3H^+$), tributylammonium ion ($N(C_4H_9)_3H^+$) and the like.

Furthermore, tetraalkylammonium ion can be exemplified by tetramethylammonium ion ($N(CH_3)_4^+$), tetraethylammonium ion ($N(C_2H_5)_4^+$), tetrabutylammonium ion ($N(C_4H_9)_4^+$) and the like.

Additionally, a divalent cation can be exemplified by magnesium ion ($Mg^{2+}$), calcium ion ($Ca^{2+}$), strontium ion ($Sr^{2+}$), barium ion ($Ba^{2+}$), cadmium ion ($Cd^{2+}$), nickel(II) ion ($Ni^{2+}$), zinc ion ($Zn^{2+}$), copper(II) ion ($Cu^{2+}$), mercury(II) ion ($Hg^{2+}$), iron(II) ion ($Fe^{2+}$), cobalt(II) ion ($Co^{2+}$), tin(II) ion ($Sn^{2+}$), lead(II) ion ($Pb^{2+}$), manganese(II) ion ($Mn^{2+}$) and the like.

Additionally, a trivalent cation can be exemplified by aluminium ion ($Al^{3+}$), iron(III) ion ($Fe^{3+}$), chromium(III) ion ($Cr^{3+}$) and the like.

Additionally, a tetravalent cation can be exemplified by tin(IV) ion ($Sn^{4+}$) and the like.

"A" may be a complex ion and may be exemplified by diammine silver ion ($[Ag(NH_3)_2]^+$), vioreo ($[CoCl_2(NH_3)_4]^+$), tetraammine zinc(II) ion ($[Zn(NH_3)_4]^{2+}$), tetraammine copper(II) ion ($[Cu(NH_3)_4]^{2+}$), tetraaqua copper(II) ion ($[Cu(H_2O)_4]^{2+}$), thiocyano iron(III) ion ($[Fe(SCN)]^{2+}$), hexaammine nickel(II) ion ($[Ni(NH_3)_6]^{2+}$), purpureo ($[CoCl(NH_3)_5]^{2+}$), hexaammine cobalt(III) ion ($[Co(NH_3)_6]^{3+}$), hexaaqua cobalt(III) ion ($[Co(H_2O)_6]^{3+}$), hexaammine chromium(III) ion ($[Cr(NH_3)_6]^{3+}$), roseo ($[Co(NH_3)_4(H_2O)_2]^{3+}$) and the like.

Moreover, an antibacterial agent composition including a fluorine-containing polymerizable compound represented by general formula (II-1) exhibits an antibacterial activity even if the content or concentration of a bismethide acid group or an organic group including a bismethide acid salt is low. The antibacterial effect is observed if the content of the organic group "$(CF_3SO_2)_2C—$" that is an organic group represented by general formula (II-1) (i.e., the content of a bismethide acid group or an organic group including a bismethide acid salt) in a resin is at least not lower than 0.1 mol % relative to the antibacterial agent composition. When the content is not lower than 1 mol %, there is provided the effect of higher antibacterial activity. The effect does not change even if the organic group is added to have a content of higher than 80 mol %, or rather the acidity is so increased as to be difficult to handle. Hence the content is preferably not lower than 0.1 mol % and not higher than 80 mol %. Accordingly, it is preferable that the antibacterial agent composition is prepared to have a content of "$(CF_3SO_2)_2C—$" (i.e., a content of a bismethide acid group or an organic group including a bismethide acid salt) of not lower than 0.1 mol % and not higher than 80 mol %.

[Invention II-2]

An antibacterial agent composition as discussed in Invention II-1, including a fluorine-containing polymerizable compound (II-a-1) represented by general formula (II-2).

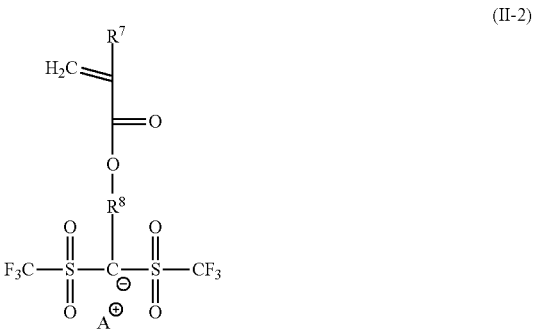

(II-2)

(In the formula (II-2), $R^7$ represents a hydrogen atom, an alkyl group, a halogen atom or a trifluoromethyl group. $R^8$ represents a single bond, a $C_1$-$C_{12}$ linear, branched or cyclic divalent hydrocarbon group, or a divalent hydrocarbon group having any combination of these, wherein $R^8$ may have an ether bond, an ester bond, an amide bond or an urethane bond, some carbon atoms contained in $R^8$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention II-3]

An antibacterial agent composition as discussed in Invention II-1, including a fluorine-containing polymerizable compound (II-a-2) represented by general formula (II-3).

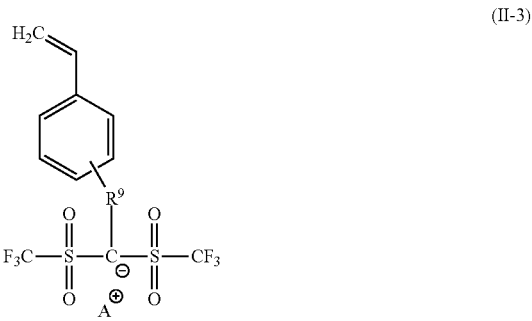

(II-3)

(In the formula (II-3), $R^9$ represents a single bond, a $C_1$-$C_{12}$ linear, branched or cyclic divalent hydrocarbon group, or a divalent hydrocarbon group having any combination of these, wherein $R^9$ may have an ether bond, an ester bond, an amide bond or an urethane bond, some carbon atoms contained in $R^9$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention II-4]

An antibacterial agent composition as discussed in Invention II-1, including a fluorine-containing polymerizable compound (II-a-3) represented by general formula (II-4).

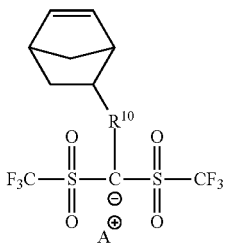

(II-4)

(In the formula (II-4), $R^{10}$ represents a single bond, a $C_1$-$C_{12}$ linear, branched or cyclic divalent hydrocarbon group, or a divalent hydrocarbon group having any combination of these, wherein $R^{10}$ may have an ether bond, an ester bond, an amide bond or an urethane bond, some carbon atoms contained in $R^{10}$ may be substituted with silicon, and some or all hydrogen atoms may be substituted with fluorine atom or hydroxyl group. "C" and "A" are bonded to each other through a covalent bond or an ionic bond, and "A" represents a hydrogen atom or a cation.)

[Invention II-5]

An antibacterial agent composition as discussed in Inventions II-1 to II-4, further including a polymerizable compound (II-b-1) represented by general formula (II-5).

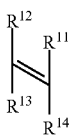

(II-5)

(In the formula (II-5), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group. Additionally, $R^{11}$ and $R^{12}$, or $R^{13}$ and $R^{14}$ may be bonded to each other to form a ring and may contain a $C_3$-$C_{12}$ single, double or multi ring structure. "C" and "A" are bonded to each other through a covalent bond or an ionic bond, and "A" represents a hydrogen atom or a cation.)

[Invention II-6]

An antibacterial agent composition as discussed in Inventions II-1 to II-5, further including a polymerizable compound (II-b-2) represented by general formula (II-6).

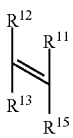

(II-6)

(In the formula (II-6), $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ has one or more kinds of functional groups selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.)

[Invention II-7]

An antibacterial agent composition as discussed in Invention II-5 or II-6, further containing a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group.

[Invention II-8]

An antibacterial resin obtained by polymerization reaction or cross-linking reaction of an antibacterial agent composition as discussed in Inventions II-1 to II-7.

2. Fluorine-Containing Polymerizable Compound (II-a)

Then, a fluorine-containing polymerizable compound (II-a) contained in an antibacterial agent composition of the present invention and having a bismethide acid group or an organic group including a bismethide acid salt will be discussed.

A fluorine-containing polymerizable compound (II-a) represented by general formula (II-1) is exemplified by: a fluorine-containing polymerizable compound (II-a-1) having an ester bond and represented by general formula (II-2) as discussed in Invention II-2; a fluorine-containing polymerizable compound (II-a-2) having a styrene chain in a main chain and represented by general formula (II-3) as discussed in Invention II-3; and a fluorine-containing polymerizable compound (II-a-3) having a norbornene ring in a main chain and represented by general formula (II-4) as discussed in Invention II-4. In addition, it is possible to cite a vinyl-based fluorine-containing polymerizable compound (II-a), and a fluorine-containing polymerizable compound (II-a) having an amide bond.

Thus, a fluorine-containing polymerizable compound represented by general formula (II-1) and having a bismethide acid group or an organic group including a bismethide acid salt as discussed in Invention II-1 is exemplified by those that include: a fluorine-containing polymerizable compound (II-a-1) having an ester bond and represented by general formula (II-2) as discussed in Invention II-2; a fluorine-containing polymerizable compound (II-a-2) having a styrene chain in a main chain and represented by general formula (II-3) as discussed in Invention II-3; and a fluorine-containing polymerizable compound (II-a-3) having a norbornene ring in a main chain and represented by general formula (II-4) as discussed in Invention II-4. In addition, the fluorine-containing polymerizable compound having a bismethide acid group or an organic group including a bismethide acid salt is exemplified by a vinyl-based fluorine-containing polymerizable compound and a fluorine-containing polymerizable compound having an amide bond.

A fluorine-containing polymerizable compound (II-a-1) having an ester bond and represented by general formula (II-3) as discussed in the invention can be exemplified by the following ester-based fluorine-containing polymerizable compounds (II-a-1)-1 to (II-a-1)-3.
Ester-Based Fluorine-Containing Polymerizable Compound (II-a-1)-1
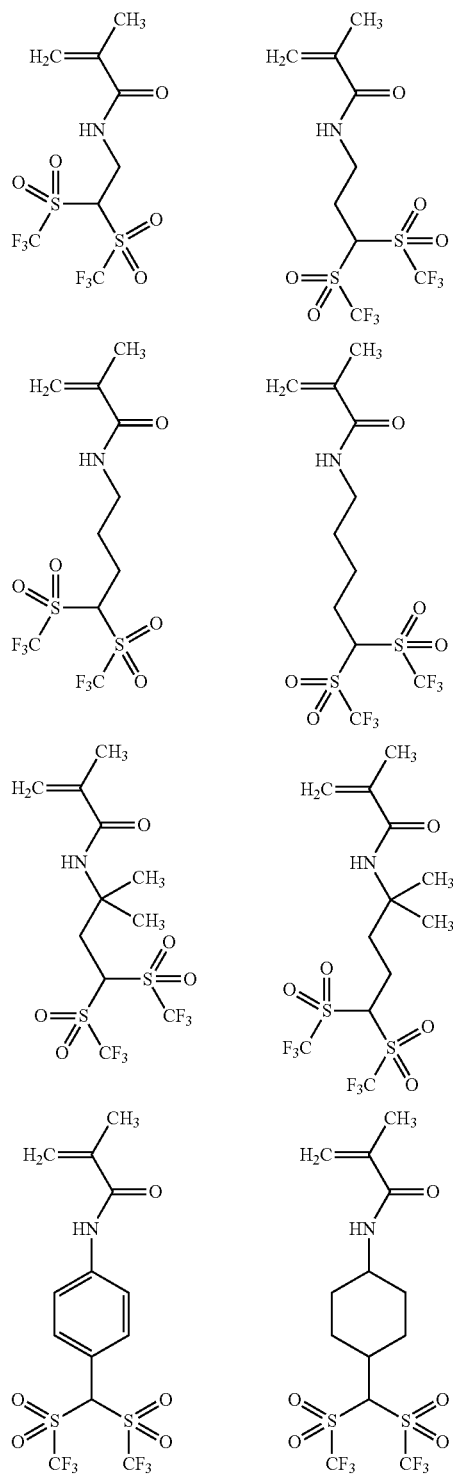
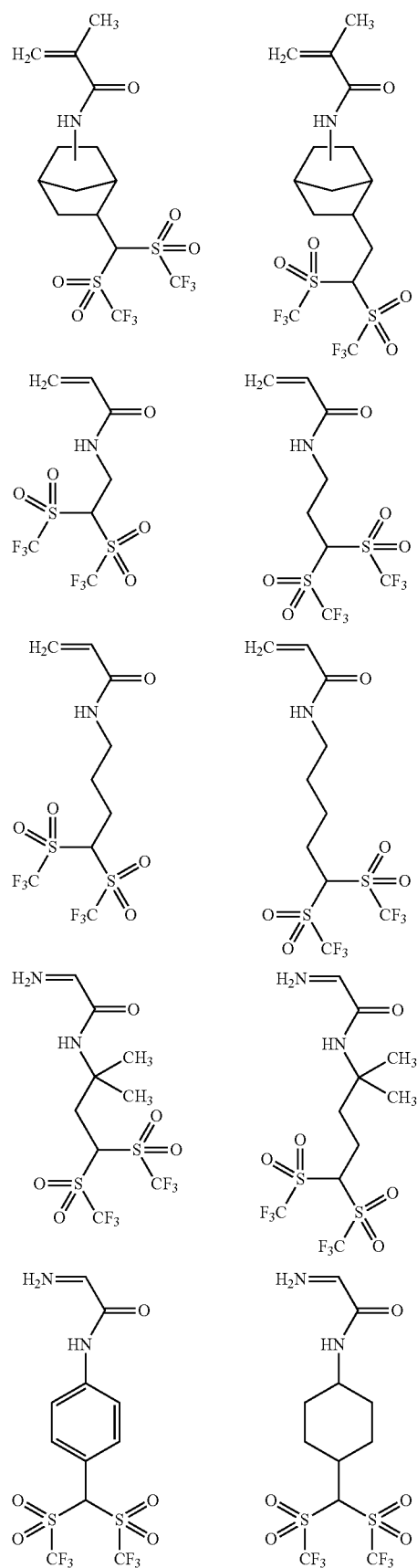

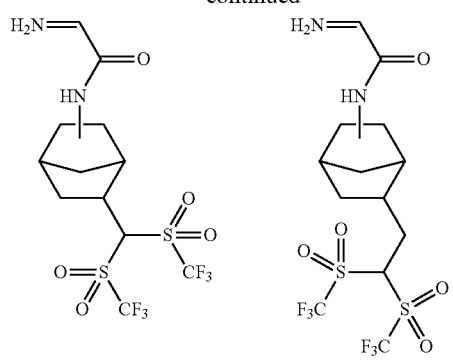
Ester-Based Fluorine-Containing Polymerizable Compound (II-a-1)-2
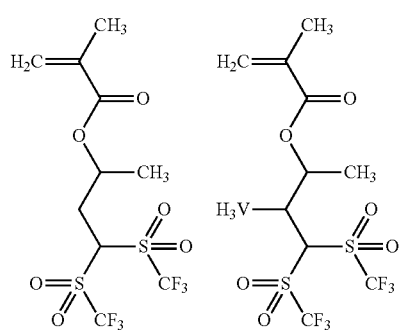
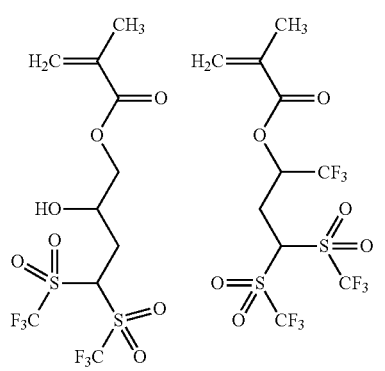
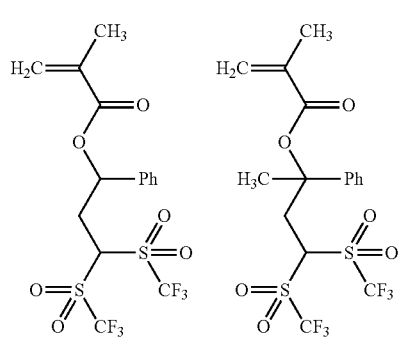
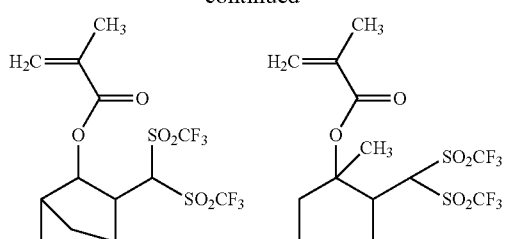
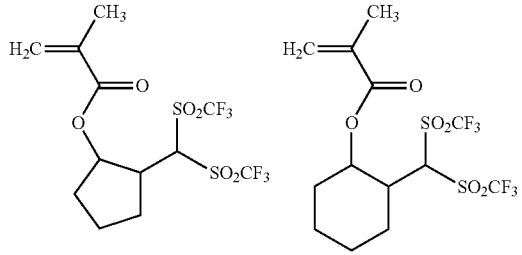
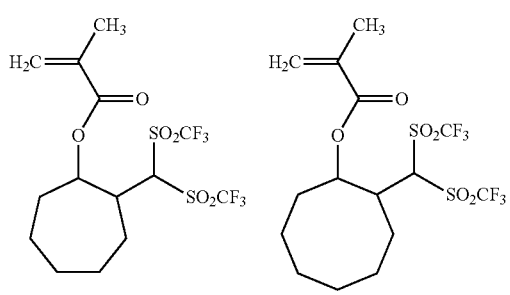
Ester-Based Fluorine-Containing Polymerizable Compound (II-a-1)-3
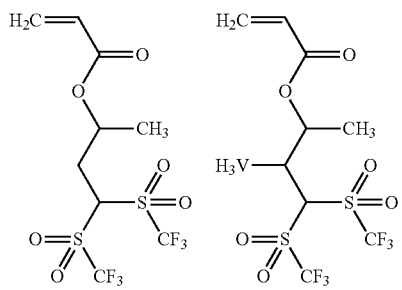
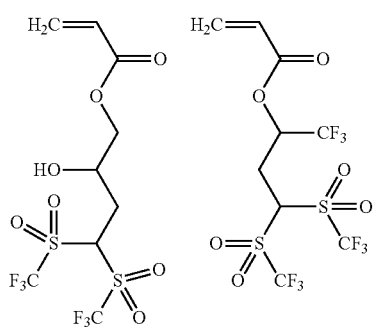

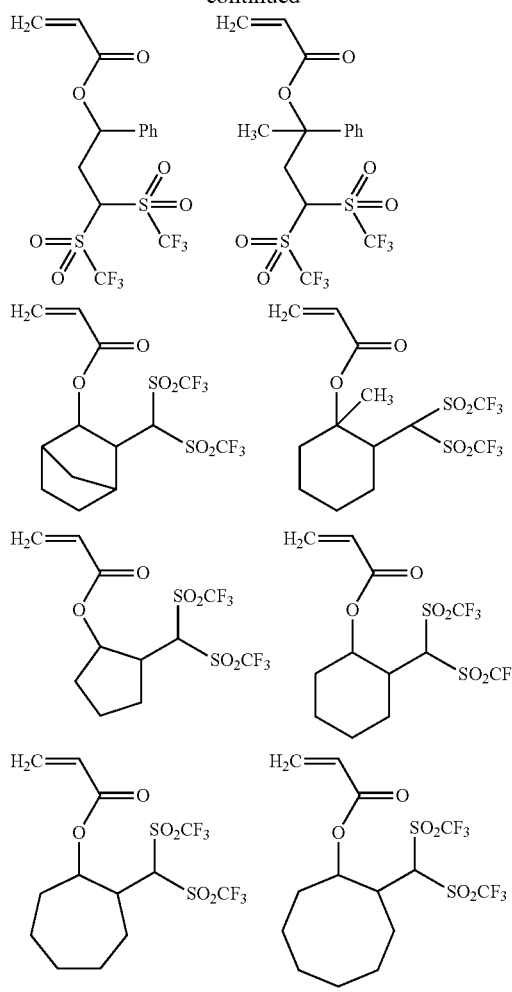

A fluorine-containing polymerizable compound (II-a-2) having a styrene bond and represented by general formula (II-3) as discussed in Invention II-3 is exemplified by the following styrene-based fluorine-containing polymerizable compound (II-a-2).

Styrene-Based Fluorine-Containing Polymerizable Compound (II-a-2)

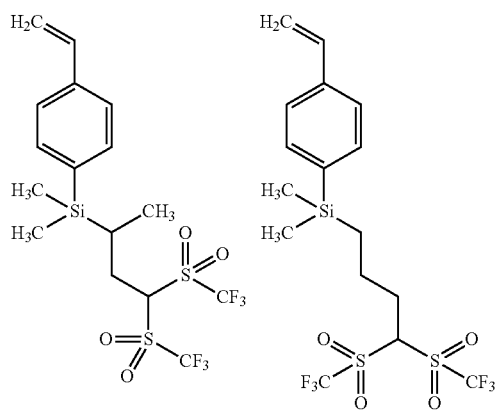

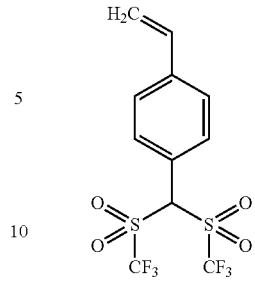

A fluorine-containing polymerizable compound (II-a-3) represented by general formula (II-4) as discussed in Invention II-4 is exemplified by a fluorine-containing polymerizable compound (II-a-3) having a norbornene ring in a main chain.

Fluorine-Containing Polymerizable Compound (II-a-3) Having Norbornene Ring in Main Chain

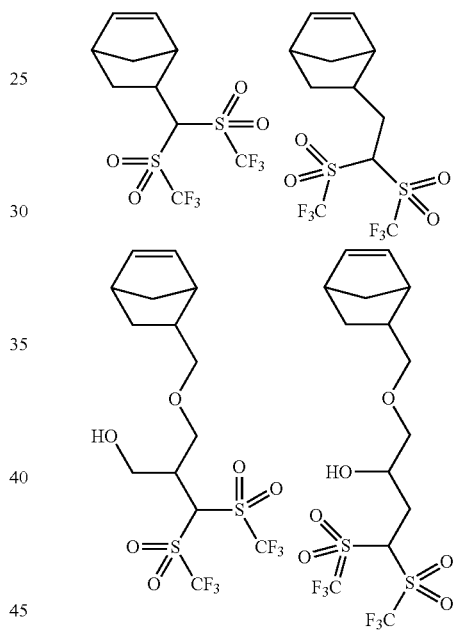

A fluorine-containing polymerizable compound (II-a) represented by general formula (II-1) as discussed in Invention II-1 is exemplified by a vinyl-based fluorine-containing polymerizable compound (II-a), an amide-based fluorine-containing polymerizable compound (II-a)-1, (II-a)-2 and the like, a fluorine-containing polymerizable compound (II-a) having a trismethide acid group, and the like.

Vinyl-Based Fluorine-Containing Polymerizable Compound (II-a)

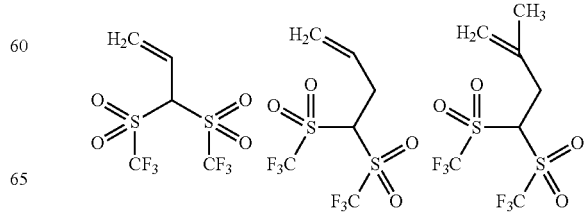

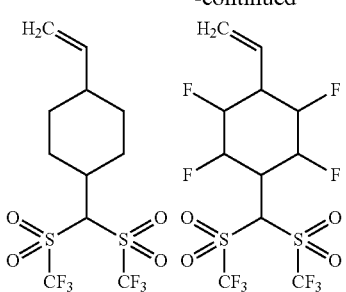
Amide-Based Fluorine-Containing Polymerizable Compound (II-a)-1
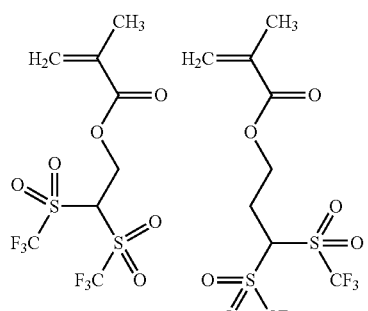
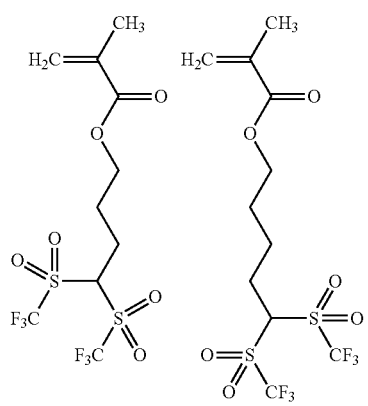
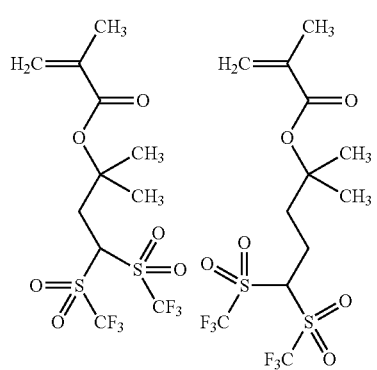
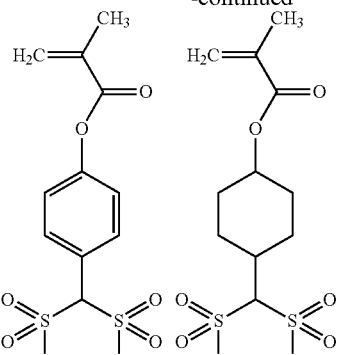
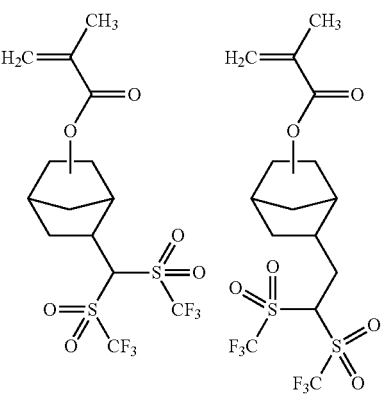
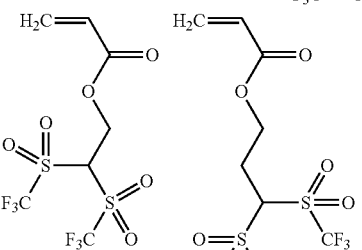
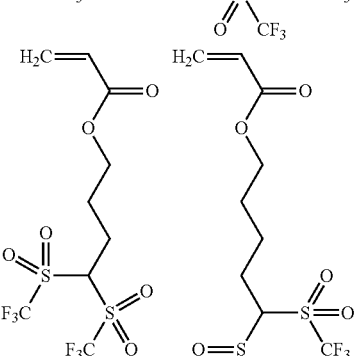
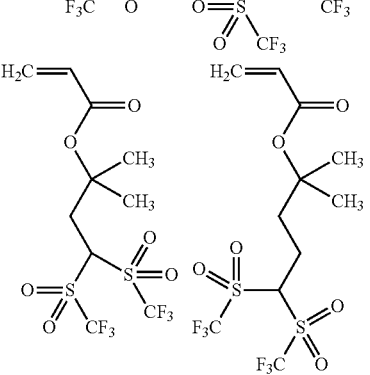

-continued
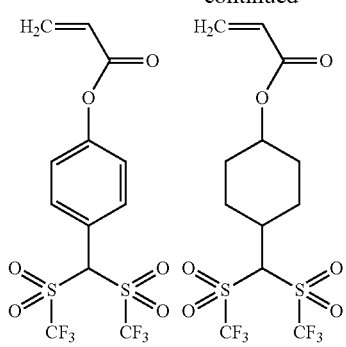
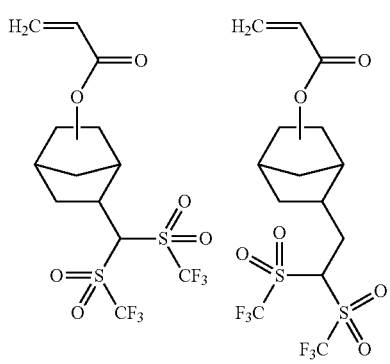
Amide-Based Fluorine-Containing Polymerizable Compound (II-a)-2
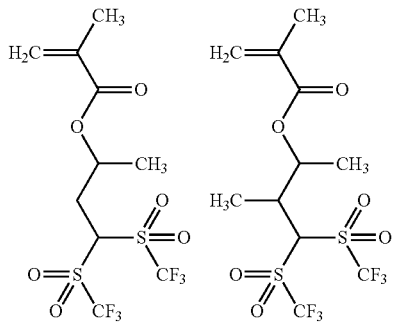
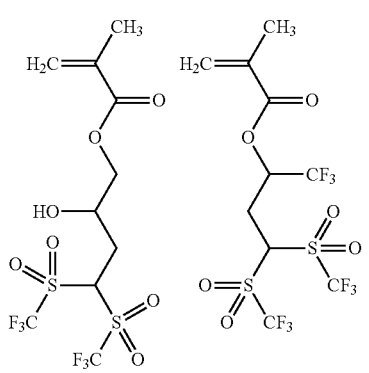
-continued
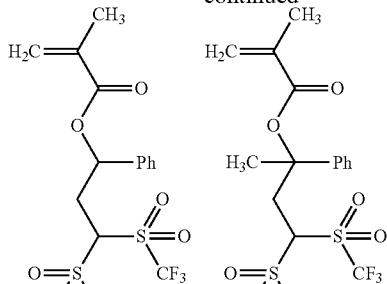
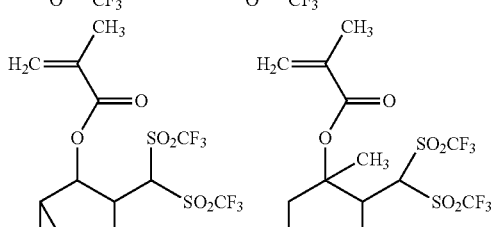
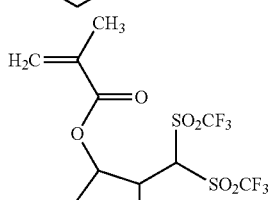
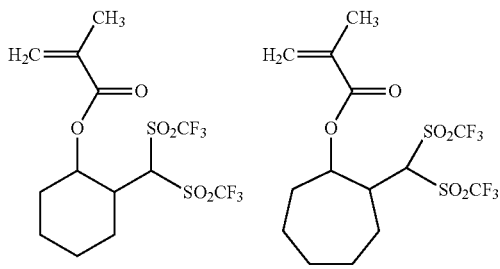
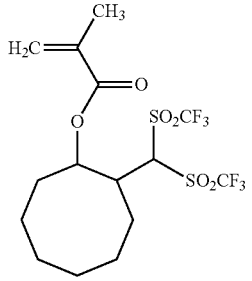
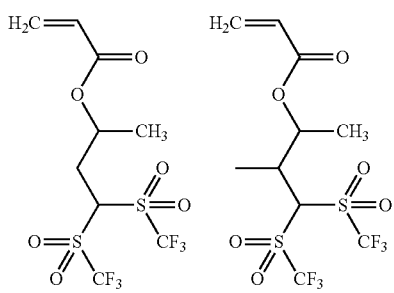

-continued

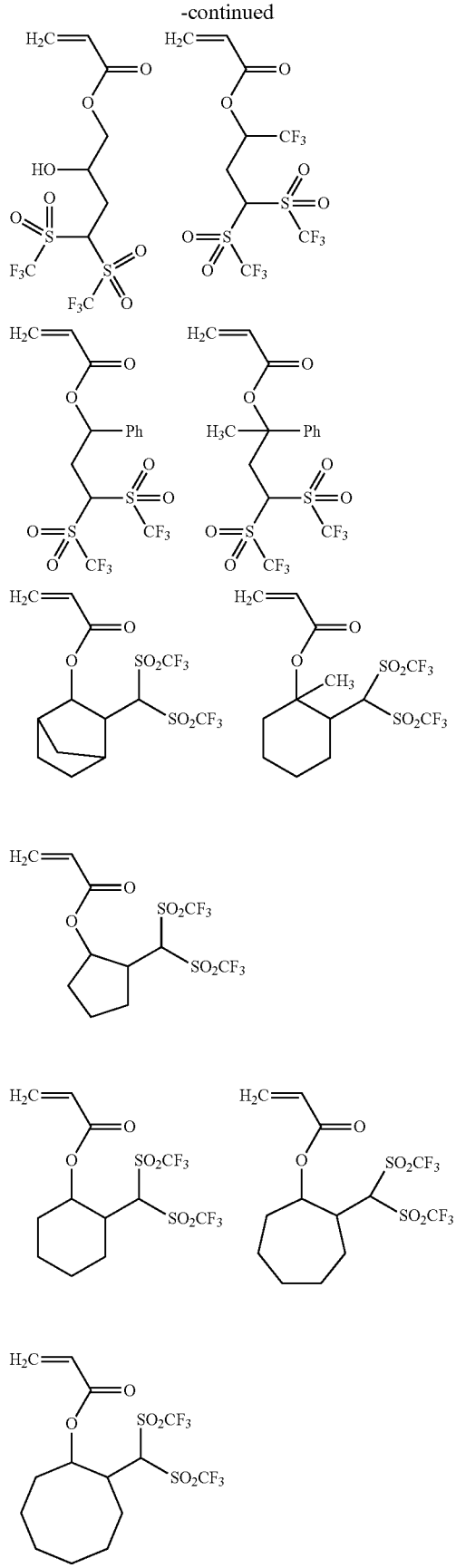

Fluorine-Containing Polymerizable Compound (II-a) Having Trismethide Acid Group

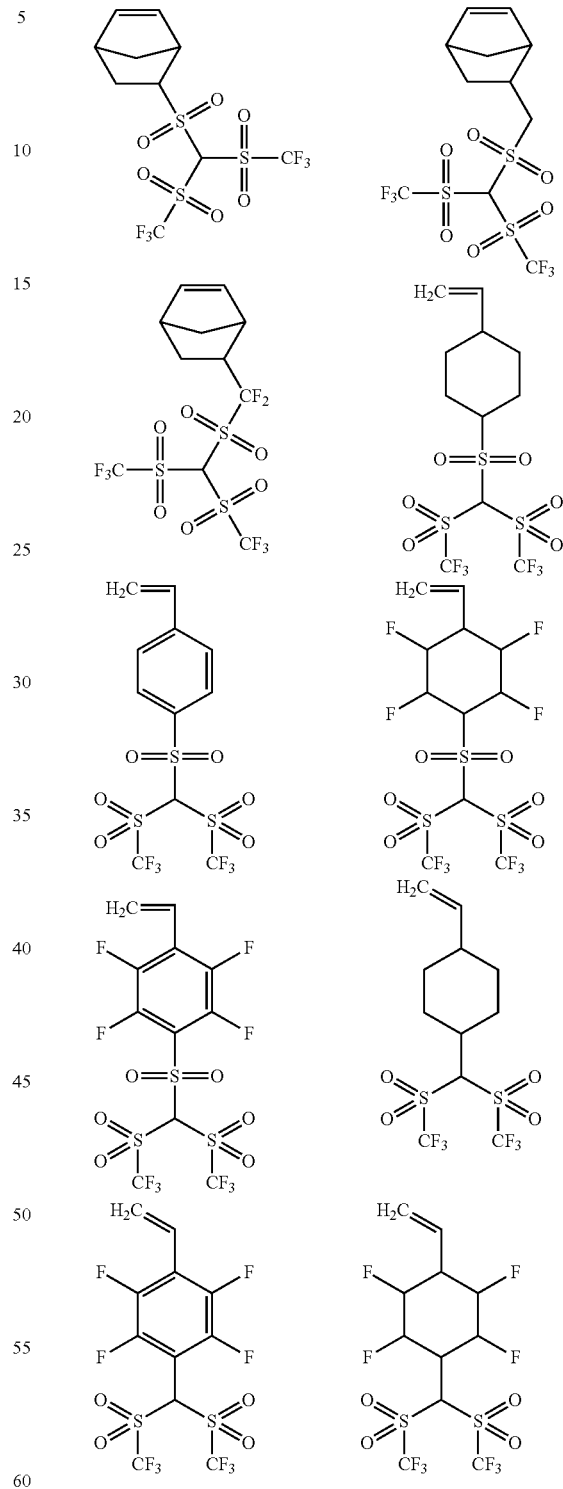

3. Polymerizable Compound (II-b-1) and (II-b-2)

Then, polymerizable compounds (II-b-1) and (II-b-2) contained in a resin used for an antibacterial agent of the present invention will be discussed.

It is possible in an antibacterial agent composition according to the present invention to use a polymerizable compound (II-b-1) represented by general formula (II-5) or a polymerizable compound (II-b-2) represented by general formula (II-6), in addition to a fluorine-containing polymerizable compound (II-a), for the purpose of adjusting the content of the active component (i.e., a bismethide acid group or an organic group including a bismethide acid salt) in an antibacterial agent or adjusting the solvent solubility, applicability and mechanical properties of a resin or introducing a cross-linkable functional group. The polymerizable compound (II-b-1) is a polymerizable compound having no cross-linkable group and the polymerizable compound (II-b-2) is a polymerizable compound having a cross-linkable group.

A polymerizable compound contained in an antibacterial agent composition of the present invention may include a fluorine-containing polymerizable compound (II-a) alone, or may include a fluorine-containing polymerizable compound (II-a) and a polymerizable compound (II-b-1) or polymerizable compound (II-b-2).

In a case of using a multifunctional polymerizable compound such as a multifunctional acrylate and the like as a polymerizable compound (II-b-1), a resin is allowed to have high mechanical strength and therefore preferably adopted.

Additionally, a further addition of a polymerizable compound (II-b-1) or a polymerizable compound (II-b-2) having a cross-linkable moiety such as hydroxyl group and the like allows providing a resin which is reacted with a curing agent such as isocyanate compound and the like to form a cross-linking structure and allows providing a resin having high mechanical strength. Therefore, this resin is preferably adopted.

A polymerizable compound (II-b-1) which may be contained in an antibacterial agent composition of the present invention is represented by general formula (II-5).

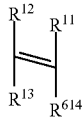

(II-5)

In this formula, $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with fluorine atom or hydroxyl group.

Additionally, $R^{11}$ and $R^{12}$, or $R^{13}$ and $R^{14}$ may be bonded to each other to form a ring and may contain a $C_3$-$C_{12}$ single, double or multi ring structure.

A polymerizable compound (II-b-2) which may be contained in an antibacterial agent composition of the present invention is represented by general formula (II-6).

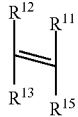

(II-6)

In this formula, $R^{11}$ represents a hydrogen atom, a $C_1$-$C_4$ alkyl group, a halogen atom or a $C_1$-$C_4$ fluoroalkyl group. $R^{12}$ and $R^{13}$ mutually independently represent a hydrogen atom, a $C_1$-$C_4$ alkyl group or a halogen atom. $R^{11}$ and $R^{12}$ or $R^{13}$ may be bonded to each other to form a ring and may contain a $C_3$-$C_{12}$ single, double or multi ring structure. $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with fluorine atom or hydroxyl group. $R^{15}$ is characterized by being at least one group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.

As a polymerizable compound (II-b-2), there is adopted at least one kind of compound selected from maleic anhydride, acrylic ester, fluorine-containing acrylic ester, methacrylic ester, fluorine-containing methacrylic ester, styrene-based compound, fluorine-containing styrene-based compound, vinyl ether, fluorine-containing vinyl ether, allyl ether, fluorine-containing allyl ether, olefins, fluorine-containing olefins, norbornene compound and fluorine-containing norbornene compound.

Acrylic ester or methacrylic ester, serving as a polymerizable compound (II-b-2) is required only to be able to form a copolymer together with a fluorine-containing polymerizable compound (II-a), a fluorine-containing polymerizable compound (II-a-1), a fluorine-containing polymerizable compound (II-a-2) or a fluorine-containing polymerizable compound (II-a-3), and therefore usable with no particular limit on its ester side chain.

If exemplifying acrylic ester and methacrylic ester by known compounds, it is possible to cite: alkyl esters of acrylic acid or methacrylic acid, such as methyl acrylate, methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, n-hexyl acrylate, n-hexyl methacrylate, n-octyl acrylate, n-octyl methacrylate, 2-ethylhexyl acrylate, 2-ethylhexyl methacrylate, lauryl acrylate, lauryl methacrylate, 2-hydroxyethyl acrylate, 2-hydroxyethyl methacrylate, 2-hydroxypropyl acrylate, 2-hydroxypropyl methacrylate and the like; and acrylates or methacrylates containing ethylene glycol, propylene glycol or tetramethylene glycol group. It is also possible to cite unsaturated amides such as acrylamide, methacrylamide, N-methylol acrylamide, N-methylol methacrylamide, diacetone acrylamide and the like. Furthermore, it is also possible to cite vinyl silanes and acrylic or methacrylic esters containing acrylonitrile, methacrylonitrile or alkoxysilane, tert-butyl acrylate, tert-butyl methacrylate, 3-oxocyclohexyl acrylate, 3-oxocyclohexyl methacrylate, adamantyl acrylate, adamantyl methacrylate, alkyladamantyl acrylate, alkyladamantyl methacrylate, cyclohexyl acrylate, cyclohexyl methacrylate, tricyclodecanyl acrylate, tricyclodecanyl methacrylate, an acrylate or methacrylate containing a ring structure selected from a lactone ring and a norbornene ring, acrylic acid, methacrylic acid, etc. Furthermore, it is also possible to cite the above-mentioned acrylate compounds containing a cyano group at its α-position, and analogous compounds such as maleic acid, fumaric acid and maleic anhydride.

A fluorine-containing acrylic ester or a fluorine-containing methacrylic ester serving as a polymerizable compound (II-b-2) can be exemplified by: a monomer containing a fluorine atom or a group having fluorine atom, at α-position of acryl; an acrylic ester or a methacrylic ester which includes at its ester moiety a substituent containing fluorine atom; and a fluorine-containing compound which contains fluorine at both α-position and the ester moiety. Furthermore, a cyano group may be introduced into α-position. As a polymerizable compound having α-position into which a fluorine-containing alkyl group is introduced, there may be adopted a polymerizable compound obtained by introducing a fluorine-containing group selected from a trifluoromethyl group, trifluoroethyl group and nonafluoro-n-butyl group into α-position of the non-fluorine-containing acrylic or methacrylic ester.

On the other hand, polymerizable compounds containing fluorine at its ester moiety are polymerizable compounds that have a fluorine alkyl group (perfluoroalkyl group or fluoroalkyl group) at ester moiety or polymerizable compounds having an ester moiety where a cyclic structure and a fluorine atom are coexistent, and exemplified by acrylic or methacrylic ester which contains a unit having a fluorine-containing benzene ring, a fluorine-containing cyclopentane ring, a fluorine-containing cyclohexane ring, a fluorine-containing cycloheptane ring and the like (i.e., a unit of which cyclic structure is substituted with a fluorine atom, a trifluoromethyl group or hexafluorocarbinol group). Additionally, acrylic or methacrylic esters of which ester moiety is a fluorine-containing t-butyl ester group are also usable.

It is also possible to use a polymerizable compound obtained by combining these fluorine-containing functional groups and a fluorine-containing alkyl group of α-position. Such a polymerizable compound can be exemplified by 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, 6-[3,3,3-trifluoro-2-hydroxy-2-(trifluoromethyl)propyl]bicyclo[2.2.1]hept-2-yl acrylate, 6-[3,3,3-trifluoro-2-hydroxy-2-(trifluoromethyl)propyl]bicyclo[2.2.1]hept-2-yl 2-(trifluoromethyl)acrylate, 6-[3,3,3-trifluoro-2-hydroxy-2-(trifluoromethyl)propyl]bicyclo[2.2.1]hept-2-yl methacrylate, 1,4-bis(1,1,1,3,3,3-hexafluoro-2-hydroxyisopropyl)cyclohexyl acrylate, 1,4-bis(1,1,1,3,3,3-hexafluoro-2-hydroxyisopropyl)cyclohexyl methacrylate, and 1,4-bis(1,1,1,3,3,3-hexafluoro-2-hydroxyisopropyl)cyclohexyl 2-trifluoromethyl acrylate. Fluorine-containing polymerizable compounds are effective at improving the solvent solubility of the obtained resin and improving surface properties and water repellency, so as to be preferably adoptable as a polymerizable compound providing a repeating unit (II-b-1) which is contained in an antibacterial agent composition of the present invention.

As a polymerizable compound (II-b-1), it is possible to cite a styrene-based compound and a fluorine-containing styrene-based compound, such as styrene, fluorinated styrene and hydroxystyrene. In addition, a compound to which one or a plurality of hexafluorocarbinol groups or functional groups formed by protecting the hexafluorocarbinl groups at hydroxyl group are bonded can be cited also. More specifically, it is possible to cite: styrene or hydroxystyrene where hydrogen is substituted with a fluorine atom or trifluoromethyl group; styrene having α-position to which halogen, alkyl group or a fluorine-containing alkyl group is bonded; and styrene having a perfluorovinyl group. Fluorine-containing styrene-based compounds are effective at improving solvent solubility and improving the surface properties and the water repellency of the obtained resin, similarly to fluorine-containing acrylic esters, so as to be preferably adoptable as a polymerizable compound (II-b-1) which is contained in an antibacterial agent composition of the present invention.

As a polymerizable compound (II-b-1), it is possible to cite: vinyl ethers; fluorine-containing vinyl ethers; allyl ethers; fluorine-containing allyl ethers; and alkyl vinyl ethers and alkyl allyl ethers having a methyl group, ethyl group, propyl group, butyl group or a hydroxyl group selected from hydroxyethyl group and hydroxybutyl group. Additionally, it is also possible to cite: cyclic vinyls and allyl ethers having a cyclohexyl group, norbornyl group or aromatic ring and those having hydrogen or a carbonyl bond in its cyclic structure; and fluorine-containing vinyl ethers and fluorine-containing allyl ethers in which some or all hydrogen atoms of the above-mentioned functional groups are substituted with fluorine atom(s).

Moreover, a polymerizable compound (II-b-1) is usable with no particular limitation insofar as it is a vinyl ester, vinyl silane, olefin, a fluorine-containing olefin, a norbornene compound, a fluorine-containing norbornene compound or other compound having a polymerizable unsaturated bond.

A hydrocarbon-based olefin that serves as a polymerizable compound (II-b-1) can be exemplified by ethylene, propylene, isobutene, cyclopentene and cyclohexene. A fluorinated hydrocarbon-based olefin can be exemplified by vinyl fluoride, vinylidene fluoride, trifluoroethylene, chlorotrifluoroethylene, tetrafluoroethylene, hexafluoropropylene and hexafluoroisobutene.

Additionally, a norbornene compound serving as a polymerizable compound (II-b-1) can be exemplified by norbornene, 1-methyl norbornene, 5-methyl norbornene, 5-ethyl norbornene, 5,6-dimethyl norbornene, 7-methyl norbornene, 5,5,6-trimethyl norbornene, tricyclo[4.3.0.1 2.5]-3-decene, tricyclo[4.4.0.1 2.5]-3-undecene, tetracyclo[4.4.0.1 2.5.1 7.10]-3-dodecene, 8-methyltetracyclo[4.4.0.1 2.5.1 7.10]-3-dodecene and 8-ethyltetracyclo[4.4.0.1 2.5.1 7.10]-3-dodecene. Incidentally, the above-mentioned polymerizable compounds may be used singly or in combination of two or more kinds.

As a polymerizable compound (II-b-2), it is particularly preferable to use the following polymerizable compounds.

It is possible to cite the following multifunctional polymerizable compounds including 2-hydroxyethyl acrylate, hydroxypropyl acrylate, 4-hydroxybutyl acrylate, 3-(trimethoxysilyl)propyl acrylate, 3-chloro-2-hydroxypropyl methacrylate, ethyl 2-(hydroxymethyl)acrylate, 2-hydroxyethyl methacrylate, hydroxypropyl methacrylate, 3-(trimethoxysilyl)propyl methacrylate, 3-[tris(trimethylsilyloxy)silyl]propyl methacrylate, 2-(trimethylsilyloxy)ethyl methacrylate, 2-(triethoxysilyl)propyl methacrylate, allytriethoxysilane, allytrimethoxysilane, 3-(acryloxy)propyltrimethoxysilane, [bicycle[2.2.1]hept-5-en-2-yl]triethoxysilane, vinyltrimethoxysilane, triethoxyvinylsilane, vinyltris(2-methoxyethoxy)silane, N-[2-(N-vinylbenzylamino)ethyl]-3-aminopropyltrimethoxysilane hydrochloride, allytrichlorosilane, trichlorovinylsilane, 3-methyl-1-penten-4-yn-3-ol, 2-(furfurylthio)ethylamine, trans-aconitic acid, acrylic acid, 4-aminocinnamic acid, angelic acid, 2-acetamideacrylic acid, 3-butene-1,2,3-tricarboxylic acid, 2-bromocinnamic acid, 2-benzylacrylic acid, caffeic acid, 4-chlorocinnamic acid, trans-cinnamic acid, citraconic acid, trans-p-coumaric acid, trans-o-coumaric acid, trans-m-coumaric acid, crotonic acid, α-cyanocinnamic acid, 1-cyclohexene-1-carboxylic acid, 1-cyclopentenecarboxylic acid, α-cyano-4-hydroxycinnamic acid, traumatic acid, trans-2-decenoic acid, 3,4-dimethoxycinnamic acid, trans-2,3-dimethoxycinnamic acid, trans-2,5-dichlorocinamic acid, fumaric acid, monoethyl fumarate, trans-2-hexenoic acid, 2-heptenoic acid, monoethyl itaconate, monoamide maleate, mesaconic acid, methacrylic acid, 4-methyl-2-pentenoic acid, trans, trans-muconic acid, mucobromic acid, mucochloric acid, 3-methylcrotonic acid, 4-methoxycinnamic acid, mono(2-acryloyloxyethyl) succinate, 3-(5-nitro-2-furyl)acrylic acid, 3-(3-pyridyl)crylic acid, α-phenylcinnamic acid, shikimic acid, tiglic acid, 2-thiopheneacrylic acid, 2-(trifluoromethyl)acrylic acid, 3-(trifluoromethyl)cinnamic acid, 4-(trifluoromethyl)cinnamic acid, 2-(trifluoromethyl)cinnamic acid, allyl mercaptan, allyl glycidyl ether, 1,3-butadiene monoepoxide, 1,2-epoxy-5-hexene, 1,2-epoxy-9-decene, allobarbital, 1,9-decadiene, 1,11-dodecadiene, dicyclopentadiene, 2,5-dimethyl-1,5-hexadiene, diisopropylidene acetone, 2,3-dimethyl-1,3-butadiene, diethyl diallylmalonate, 1,3-dibenzylidene-2-cyclohexanone, 2,6-dimethyl-2,4,6-octatriene, 1,5,9-decatriene, 9,10-epoxy-1,5-cyclododecadiene, farnesyl acetate, geranyl-linalool, geranyl nitrile, 1,5-hexadiene, 1,4-hexadiene, 1,5-hexadiene-3,4-diol, isoprene, (±)-limonene, myrcene, methylcyclopentadiene, 2,5-norbornadiene, 1,7-octadiene, monoethyl fumarate, ethyl hydrogen maleate, monooctyl maleate, monomethyl maleate, monoisopropyl fumarate, mono(2-acryloyloxyethyl) succinate, 6-acrylamide hexanoic acid, acrylamide, allylamine, 1-allyl-2-thiourea, 1-allyl-3-(2-hydroxyethyl)-2-thiourea, allylurea, methyl 3-aminocrotonate, 3-amino-5,5-dimethyl-2-cyclohexen-1-one, S-allyl-L-cysteine, ethyl 3-amino-4,4,4-trifluorocrotonate, 3-amino-2-cyclohexen-1-one, 3-benzalbutyramide, crotonamide, cinnamamide, 2-(1-cyclohexenyl)ethylamine, glycidyl methacrylate and polyethylene glycol diacrylate.

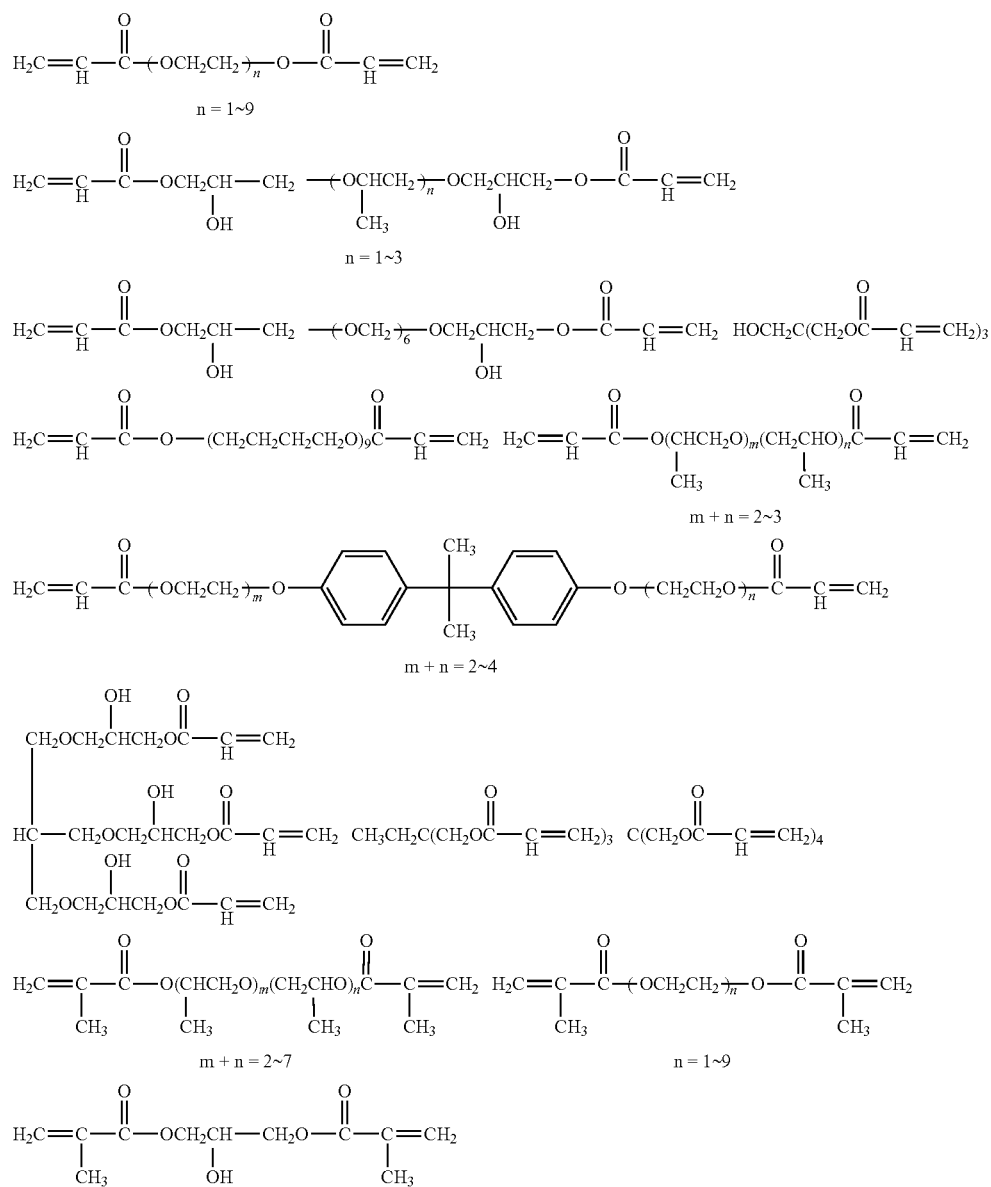

-continued

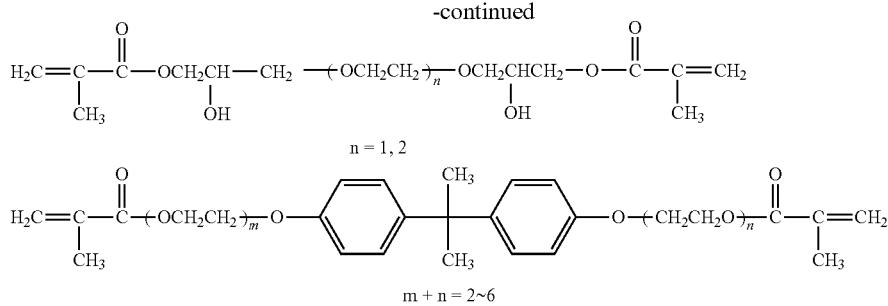

In particular, polyethylene glycol diacrylate, styrene, 2,3,4,5,6-pentafluorostyrene, 2-hydroxyethyl methacrylate, acrylonitrile, 2-norbornene and the like are preferably usable.

4. Cross-Linking Agent

A cross-linking agent will be discussed.

In the present invention, it is possible to use a cross-linking agent reactive with a functional group such as hydroxyl group, mercapto group, carboxyl group, amino group, epoxy group, alkenyl group, alkynyl group, acryloyl group, methacryloyl group, chlorosilyl group, alkoxysilyl group, hydrosilyl group and the like, for the purpose of improving the durability of an antibacterial agent.

The cross-linking agent is exemplified by isocyanate compounds, epoxy compounds, aldehyde-based compounds, chlorosilanes, alkoxysilanes, melamine-based compounds, sulfur and sulfur compounds. Of these compounds, multi-functional compounds are preferably adopted from the fact that when a resin serving as an active component of an antibacterial agent of the present invention is synthesized it becomes possible to increase the cross-linking density of the resin and the fact that a resin excellent in mechanical strength can be obtained.

In synthesizing a resin by using an antibacterial agent composition of the present invention, it is possible to employ a resin synthesis method where a peroxide compound or azo compound is used as a cross-linking agent and cross-linking is initiated by free-radical reaction. In that the resin is obtained to have durability, this method is particularly preferably adopted for the antibacterial agent of the present invention.

An isocyanate compound to be used as a cross-linking agent when synthesizing a resin by using an antibacterial agent composition of the present invention and reacted with hydroxyl group, amino group or the like to form a cross-linking structure in the resin is exemplified by diisocyanate compounds such as 1,4-phenylene diisocyanate, 4,4'-diphenylmethane diisocyanate, 3,3'-dichlorobiphenyl-4,4'-diisocyanate, dicyclohexylmethane-4,4'-diisocyanate, hexamethylene diisocyanate, m-xylylene diisocyanate, trilene-2,6-diisocyanate, trimethyl hexamethylene diisocyanate, naphthalene diisocyanate, isophorone diisocyanate and the like. Additionally, it is also possible to cite the above-mentioned diisocyanate compounds in the form of an uretidinedione-type dimer, a biuret-type trimer or an isocyanurate-type trimer, adducts of polyol such as 1,3-propanediol, trimethylol propane and the like. Furthermore, it is also possible to cite triisocyanates such as triphenylmethane isocyanate and tris(isocyanatephenyl)thiophosphate, and the like.

In synthesizing a resin by using an antibacterial agent composition of the present invention, hexamethylene diisocyanate is particularly preferably employed since it exhibits stability as a compound and the resin is obtained to have flexibility.

An epoxy compound to be used as a cross-linking agent when synthesizing a resin by using an antibacterial agent composition of the present invention and reacted with carboxyl group or the like to form a cross-linking structure is exemplified by glycidyl ether-based compounds, glycidyl ester-based compounds, glycidyl amine-based compounds, alicyclic compounds and the like. For example, it is possible to cite 1,4-butanediol diglycidyl ether, 2,2-bis(4-glycidyloxyphenyl)propane, diglycidyl 1,2-cyclohexanedicarboxylate, 1,7-octadiene diepoxide, 1,5-hexadiene diepoxide, triglycidyl isocyanurate, neopentyl glycol diglycidyl ether, 1,3-butadiene monoepoxide, 1,2-epoxy-5-hexene, 1,2-epoxy-9-decene and the like. In synthesizing a resin by using an antibacterial agent composition of the present invention, 1,4-butanediol diglycidyl ether is particularly preferably employed since it has a moderate reactivity.

An aldehyde-based compound to be used as a cross-linking agent when synthesizing a resin by using an antibacterial agent composition of the present invention and reacted with phenolic hydroxyl group or the like to form a cross-linking structure is exemplified by formaldehyde, formalin, paraformaldehyde, trioxane, acetaldehyde, polyoxymethylene and propionaldehyde. In synthesizing a resin by using an antibacterial agent composition of the present invention, paraformaldehyde is particularly preferably employed since it has a moderate reactivity and easy to handle.

Chlorosilanes to be used as a cross-linking agent when synthesizing a resin by using an antibacterial agent composition of the present invention and useful for the cross-linking reaction that forms siloxane bonds is exemplified by dimethyldichlorosilane, diethyldichlorosilane, diphenyldichlorosilane, divinyldichlorosilane, methyldichlorosilane, ethyldichlorosilane, phenyldichlorosilane, vinyldichlorosilane, dichlorosilane, methyltrichlorosilane, ethyltrichlorosilane, phenyltrichlorosilane, vinyltrichlorosilane, trichlorosilane, tetrachlorosilane, 1,2-bis(trichlorosilyl)ethane, bis(trichlorosilyl)acetylene, 3-chloropropyltrichlorosilane, cyclohexyltrichlorosilane, trichloro(1H,1H,2H, 2H-tridecafluoro-n-octyl)silane, trichloro-2-cyanoethylsilane, phenyltrichlorosilane and the like. In synthesizing a resin by using an antibacterial agent composition of the present invention, dimethyldichlorosilane is particularly preferably employed since it is well reactive, inexpensive and easily available.

Alkoxysilanes to be used as a cross-linking agent when synthesizing a resin by using an antibacterial agent composition of the present invention and useful for the cross-linking reaction that forms siloxane bonds is exemplified by dimethyldimethoxysilane, diethyldimethoxysilane, diphenyldimethoxysilane, divinyldimethoxysilane, methyldimethoxysilane, ethyldimethoxysilane, phenyldimethoxysilane, vinyldimethoxysilane, dimethoxysilane, methyltrimethoxysilane, ethyltrimethoxysilane, phenyltrimethoxysilane, vinyltrimethoxysilane, trimethoxysilane, tetramethoxysilane, dimethyldiethoxysilane, diethyldiethoxysilane, diphenyldiethoxysilane, divinyldiethoxysilane, methyldiethoxysilane, ethyldiethoxysilane, phenyldiethoxysilane, vinyldiethoxysilane, diethoxysilane, methyltriethoxysilane, ethyltriethoxysilane, phenyltriethoxysilane, vinyltriethoxysilane, triethoxysilane, tetraethoxysilane, 3-aminopropyltriethoxysilane, 3-(2-aminoethylamino)propyltrimethoxysilane, 3-(2-aminoethylamino)propyltriethoxysilane, bis[3-(trimethoxysilyl)propyl]amine, 1,2-bis(trimethoxysilyl)ethane, benzyltriethoxysilane, (3-bromopropyl)trimethoxysilane, 3-trimethoxysilylpropyl chloride, 2-cyanoethyltriethoxysilane, (chloromethyl)triethoxysilane, cyclohexyltrimethoxysilane, 2-(3,4-epoxycyclohexyl)ethyltrimethoxysilane, 3-glycidyloxypropyltrimethoxysilane, (3-mercaptopropyl)trimethoxysilane, (3-mercaptopropyl)triethoxysilane, 1,1,1-trifluoro-3-(trimethoxysilyl)propane, triethoxyphenylsilane, trimethoxyphenylsilane, trimethoxy(4-methoxyphenyl)silane and trimethoxy(p-tolyl)silane. In synthesizing a resin by using an antibacterial agent composition of the present invention, dimethyldimethoxysilane is particularly preferably employed since it is well reactive, inexpensive and easily available.

Melamine-based compounds to be used as a cross-linking agent when synthesizing a resin by using an antibacterial agent composition of the present invention and reacted with hydroxyl group or the like to form a cross-linking structure is exemplified by melamine, methylolated melamine, and a methylolated melamine derivative. Furthermore, it is also possible to use a compound partially or entirely etherified by reacting methylolated melamine with a lower alcohol. Additionally, the melamine-based compounds may be either a monomer or a polymer (having two or more monomers), and may be a combination of these.

In synthesizing a resin by using an antibacterial agent composition of the present invention, methylolated melamine and a derivative thereof are particularly preferably employed since these have good reactivity and easy to handle.

Sulfur or a sulfur compound to be used as a cross-linking agent when synthesizing a resin by using an antibacterial agent composition of the present invention and reacted with alkenyl group, alkynyl group, acryloyl group, methacryloyl group or the like to form a cross-linking structure is exemplified by sulfur, tetramethylthiuram disulfide, tetraethylthiuram disulfide, tetrabutylthiuram disulfide, tetrakis(2-ethylhexyl)thiuram disulfide, dipentamethylenethiuram tetrasulfide, morpholine disulfide, 2-(4'-morpholinodithio)benzothiazol and the like.

In synthesizing a resin by using an antibacterial agent composition of the present invention, sulfur is particularly preferably employed since it is inexpensive and easy to handle.

A peroxide compound to be used as a cross-linking agent when synthesizing a resin by using an antibacterial agent composition of the present invention and useful for cross-linking initiated by free-radical reaction (i.e., a radical reaction forming alkyl group and the like) is exemplified by benzoyl peroxide, dichlorobenzoyl peroxide, dicumyl peroxide, di-tert-butyl peroxide, 2,5-dimethyl-2,5-di(peroxybenzoate)hexyne-3,1,4-bis(tert-butylperoxyisopropyl)benzene, lauroyl peroxide, tert-butyl peracetate, 2,5-dimethyl-2,5-di(tert-butylperoxy)hexyne-3,2,5-trimethyl-2,5-di(tert-butylperoxy)hexane, tert-butyl perbenzoate, tert-butyl perphenylacetate, tert-butyl perisobutylate, tert-butyl per-sec-octoate, tert-butyl peroxypivalate, cumyl perpivalate, and tert-butyl perdiethylacetate.

In synthesizing a resin by using an antibacterial agent composition of the present invention, benzoyl peroxide is particularly preferably employed since it has a good reactivity and the resin is obtained to have great mechanical properties.

An azo compound to be used as a cross-linking agent when synthesizing a resin by using an antibacterial agent composition of the present invention and useful for cross-linking initiated by free-radical reaction (i.e., a radical reaction forming alkyl group and the like) is exemplified by azobisisobutyronitrile and dimethyl azoisobutyrate.

In synthesizing a resin by using an antibacterial agent composition of the present invention, azobisisobutyronitrile is particularly preferably employed since it is low-cost and easy to handle.

These cross-linking agents may be used singly or in combination by selecting two or more. It is also possible to adjust the cure rate, the pot life and the properties of a resin to be obtained suitably according to the kind or the amount of the cross-linking agent to be used.

Hereinafter, there will be discussed a polymerization method for polymerizing a fluorine-containing polymerizable compound (i.e., a precursor of the above-mentioned repeating units) singly by using a fluorine-containing polymerizable compound (II-a), a fluorine-containing polymerizable compound (II-a-1), a fluorine-containing polymerizable compound (II-a-2) or a fluorine-containing polymerizable compound (II-a-3) as an antibacterial agent composition of the present invention to obtain a resin. In addition, there will be discussed also a polymerization method where a fluorine-containing polymerizable compound (II-a), a fluorine-containing polymerizable compound (II-a-1), a fluorine-containing polymerizable compound (II-a-2) or a fluorine-containing polymerizable compound (II-a-3) is used as an antibacterial agent composition of the present invention and these fluorine-containing polymerizable compounds are copolymerized with a fluorine-containing polymerizable compound (II-b-1) or a fluorine-containing polymerizable compound (II-b-2) to obtain a resin.

5. Polymerization Method

Then a polymerization method will be discussed.

A polymerization method is exemplified by radical polymerization and a polymerization using a transition metal.

First of all, radical polymerization will be explained.

A polymerization method for obtaining a resin from an antibacterial agent composition of the present invention is not particularly limited insofar as the method is a generally usable one, but radical polymerization and ionic polymerization are preferable. It is also possible to employ coordination anionic polymerization, living anionic polymerization, cationic polymerization, ring-opening metathesis polymerization or vinylene polymerization.

Radical polymerization is conducted according to a known polymerization method selected from bulk polymerization, solution polymerization, suspension polymerization and emulsion polymerization in the presence of a radical polymerization initiator or a radical initiating source, with a batch-wise, semi-continuous or continuous operation.

The radical polymerization initiator is not particularly limited but exemplified by azo compounds, peroxide compounds and redox compounds. In order to synthesize a resin that serves as an active component of an antibacterial agent of the present invention, azobisisobutyronitrile, t-butylperoxypivalate, di-t-butylperoxide, i-butyrylperoxide, lauroyl peroxide, succinic acid peroxide, dicinnamylperoxide, di-n-propylperoxydicarbonate, t-butylperoxyallyl monocarbonate, benzoyl peroxide, hydrogen peroxide, and ammonium persulfate are preferably used to a polymerization reaction for obtaining a resin that serves as an active component of an antibacterial agent of the present invention.

In polymerization reaction for obtaining a resin by using an antibacterial agent composition of the present invention, a reaction vessel used for the polymerization reaction is not particularly limited. Additionally, a polymerization solvent may be used in the polymerization reaction. As the polymerization solvent used in the polymerization reaction for obtaining a resin that serves as an active component of an antibacterial agent of the present invention, one that does not interfere with radical polymerization is preferable, and usable examples thereof are: ester-based ones selected from ethyl acetate and n-butyl acetate; ketone-based ones selected from acetone and methyl isobutyl ketone; hydrocarbon-based ones selected from toluene and cyclohexane; and alcohol-based solvents selected from methanol, isopropyl alcohol, methyl isobutyl carbinol and ethylene glycol monomethyl ether. Additionally, it is also possible to use various types of solvents selected from water, ether-based ones, cyclic ether-based ones, fluorohydrocarbon-based ones and aromatic ones. These solvents may be used singly or in combination of not less than two kinds of them. Additionally, a molecular weight adjusting agent such as mercaptan may be used together therewith. In the polymerization reaction for obtaining a resin that serves as an active component of an antibacterial agent of the present invention, the reaction temperature in a copolymerization reaction is suitably changed according to the radical polymerization initiator or radical polymerization initiating source, and is preferably within a range of not lower than 20° C. and not higher than 200° C. in general, particularly preferably within a range of not lower than 30° C. and not higher than 140° C.

Then, a polymerization using a transition metal will be discussed.

Ring-opening metathesis polymerization is required only to use a transition metal catalyst of the group IV, V, VI or VII in the presence of a co-catalyst and to use a known method in the presence of a solvent. The transition metal catalyst is not particularly limited and exemplified by Ti-based, V-based, Mo-based and W-based catalysts. In particular, titanium(IV) chloride, vanadium(IV) chloride, vanadium trisacetylacetonate, vanadium bisacetylacetonatedichloride, molybdenum (VI) chloride and tungsten(VI) chloride are preferable in the polymerization reaction for obtaining a resin that serves as an active component of an antibacterial agent of the present invention. The amount of the catalyst is not lower than 0.001 mol % and not higher than 10 mol %, preferably not lower than 0.01 mol % and not higher than 1 mol % relative to the used monomer.

As a co-catalyst, it is possible to cite alkylaluminium and alkyltin. In particular, it is possible to cite: aluminium-based ones represented by trialkylaluminiums selected from trimethylaluminium, triethylaluminium, tripropylaluminium, triisopropylaluminium, triisobutylaluminium, tri-2-methylbutylaluminium, tri-3-methylbutylaluminium, tri-2-methylpentylaluminium, tri-3-methylpentylaluminium, tri-4-methylpentylaluminium, tri-2-methylhexylaluminium, tri-3-methylhexylaluminium and trioctylaluminium, dialkylaluminium halides selected from dimethylaluminium chloride, diethylaluminium chloride, diisopropylaluminium chloride and diisobutylaluminium chloride, monoalkylaluminium halides selected from methylaluminium dichloride, ethylaluminium dichloride, ethylaluminium diiodide, propylaluminium dichloride, isopropylaluminium dichloride, butylaluminium dichloride and isobutylaluminium dichloride, and alkylaluminium sesquichlorides selected from methylaluminium sesquichloride, ethylaluminium sesquichloride, propylaluminium sesquichloride and isobutylaluminium sesquichloride; tetra-n-butyltin; tetraphenyltin; and triphenylchlorotin. The amount of the co-catalyst to be used is within a range of 100 equivalents or less, preferably 30 equivalents or less by molar ratio relative to the transition metal catalyst.

A polymerization solvent will do unless it interferes with the polymerization reaction, and representative examples thereof are: aromatic hydrocarbon-based ones selected from benzene, toluene, xylene, chlorobenzene and dichlorobenzene; hydrocarbon-based ones selected from hexane, heptane and cyclohexane; and halogenated hydrocarbons selected from carbon tetrachloride, chloroform, methylene chloride and 1,2-dichloroethane. In the polymerization reaction for obtaining a resin that serves as an active component of an antibacterial agent of the present invention, these polymerization solvents may be used singly or in combination of two or more kinds. The reaction temperature is preferably not lower than −70° C. and not higher than 200° C. in general, particularly preferably not lower than −30° C. and not higher than 60° C.

Vinylene polymerization is required only to use a transition metal catalyst of the group VIII such as iron, nickel, rhodium, palladium, platinum and the like, or a metal catalyst of the groups IVB to VIB selected from zirconium, titanium, vanadium, chromium, molybdenum and tungsten in the presence of a co-catalyst, and to adopt a known method in the presence of a solvent. The polymerization catalyst is not particularly limited but, in the polymerization reaction for obtaining a resin that serves as an active component of an antibacterial agent of the present invention, it is particularly preferable to use: transition metal compounds of the group VIII, selected from iron(II) chloride, iron(III) chloride, iron(II) bromide, iron(III) bromide, iron(II) acetate, iron(III) acetylacetonate, ferrocene, nickelocene, nickel(II) acetate, nickel bromide, nickel chloride, dichlorohexylnickel acetate, nickel lactate, nickel oxide, nickel tetrafluoroborate, bis(allyl)nickel, bis (cyclopentadienyl)nickel, nickel(II) hexafluoroacetylacetonatetetrahydrate, nickel(II) trifluoroacetylacetonatedihydrate, nickel(II) acetylacetonatetetrahydrate, rhodium(III) chloride, rhodium tris(triphenylphosphine)trichloride, palladium(II) bis(trifluoroacetate), palladium(II) bis(acetylacetonate), palladium(II) 2-ethylhexanoate, palladium(II) bromide, palladium(II) chloride, palladium(II) iodide, palladium (II) oxide, monoacetonitriletris(triphenylphosphine) palladium(II) tretrafluoroborate, tetrakis(acetonitrile) palladium(II) tetrafluoroborate, dichlorobis(acetonitrile) palladium(II), dichlorobis(triphenylphosphine)palladium (II), dichlorobis(benzonitrile)palladium(II), palladium acetylacetonate, palladium bis(acetonitrile)dichloride, palladium bis(dimethylsulfoxide)dichloride and platinum bis(triethylphosphine)hydrobromide; and transition metal compounds of the groups IVB to VIB, selected from vanadium (IV) chloride, vanadium trisacetylacetonate, vanadium bisacetylacetonatedichloride, trimethoxy(pentamethylcyclopentadienyl)titanium(IV), bis(cyclopentadienyl)titanium dichloride and bis(cyclopentadienyl)zirconium dichloride. The amount of the catalyst is not lower than 0.001 mol % and not higher than 10 mol %, preferably not lower than 0.01 mol % and not higher than 1 mol % relative to the used monomer. The co-catalyst is exemplified by alkylaluminoxane and alkylaluminium, and in the polymerization reaction for obtaining a resin that serves as an active component of an antibacterial agent of the present invention, it is possible to particularly cite: methylaluminoxane (MAO); trialkylaluminiums such as trimethylaluminium, triethylaluminium, tripropylaluminium, triisopropylaluminium, triisobutylaluminium, tri-2- methylbutylaluminium, tri-3-methylbutylaluminium, tri-2-methylpentylaluminium, tri-3-methylpentylaluminium, tri-4-methylpentylaluminium, tri-2-methylhexylaluminium, tri-3-methylhexylaluminium, trioctylaluminium and the like; dialkylaluminium halides selected from dimethylaluminium chloride, diethylaluminium chloride, diisopropylaluminium chloride and diisobutylaluminium chloride; monoalkylaluminium halides selected from methylaluminium dichloride, ethylaluminium dichloride, ethylaluminium diiodide, propylaluminium dichloride, isopropylaluminium dichloride, butylaluminium dichloride and isobutylaluminium dichloride; and alkylaluminium sesquichlorides selected from methylaluminium sesquichloride, ethylaluminium sesquichloride, propylaluminium sesquichloride and isobutylaluminium sesquichloride. In the case of methylaluminoxane, the amount of the co-catalyst is not lower than 50 equivalents and not higher than 500 equivalents in terms of Al conversion. In the case of other alkylaluminiums, the amount of the co-catalyst is within a range of 100 equivalents or less, preferably 30 equivalents or less by molar ratio relative to the transition metal catalyst. Additionally, the polymerization solvent will do unless it interferes with the polymerization reaction, and representative examples thereof are aromatic hydrocarbon-based ones selected from benzene, toluene, xylene, chlorobenzene and dichlorobenzene, hydrocarbon-based ones selected from hexane, heptane and cyclohexane, halogenated hydrocarbon-based ones selected from carbon tetrachloride, chloroform, methylene chloride and 1,2-dichloroethane, dimethylformamide, N-methylpyrolidone and N-cyclohexylpyrolidone. These polymerization solvents may be used singly or in combination of two or more kinds. The reaction temperature is preferably not lower than −70° C. and not higher than 200° C. in general, particularly preferably not lower than −40° C. and not higher than 80° C.

As a method of removing a medium such as an organic solvent and water from the thus obtained solution or dispersion liquid (of a resin that serves as an active component of an antibacterial agent of the present invention), any known method can be used. For example, it is possible to cite methods such as reprecipitation, filtration, heating distillation under reduced pressure and the like.

6. Substrate Surface Treatment Method

Then, a substrate surface treatment method will be explained.

It is possible to conduct a substrate surface treatment in such as manner as to coat a target substrate with an antibacterial agent composition of the present invention. It is possible to dissolve the antibacterial agent composition of the present invention in a solvent and then apply it to a substrate and then dry it to form a film. Additionally, it is also possible to lead a fluorine-containing polymerizable compound or polymerizable compound contained in the antibacterial agent composition to a polymerization reaction to prepare a resin by mixing a curing agent at the time of application thereby improving the strength of the film, which is preferably adopted in the present invention.

Furthermore, it is also possible to cure a film by applying an antibacterial agent composition of the present invention obtained by mixing a curing agent in a fluoroine-containing polymerizable compound or a polymerizable compound to a substrate and then react it with heat, light or a catalyst to form a resin. Application with no solvent is also possible, which is especially effective at improving the fabrication environment.

A solvent for use in an antibacterial agent composition of the present invention is not particularly limited insofar as the solvent is not reactive with the antibacterial agent composition and the antibacterial agent composition is soluble therein. Usable examples are ketones selected from acetone, methyl ethyl ketone, cyclohexanone, methyl isoamyl ketone and 2-heptanone, polyalcohols selected from ethylene glycol, ethylene glycol monoacetate, diethylene glycol, diethylene glycol monoacetate, propylene glycol, propylene glycol monoacetate, dipropylene glycol, dipropylene glycol monoacetate, monomethyl ether, monoethyl ether, monopropyl ether, monobutyl ether and monophenyl ether, monovalent alcohols selected from methanol, ethanol, isopropyl alcohol and methyl isobutyl carbinol and derivatives of these, cyclic ethers such as dioxane, esters selected from methyl lactate, ethyl lactate, methyl acetate, ethyl acetate, butyl acetate, methyl pyruvate, ethyl pyruvate, methyl methoxypropionate and ethyl ethoxypropionate, aromatic solvents selected from xylene and toluene, fluorine-based solvents selected from chlorofluorocarbons, alternative chlorofluorocarbons, perfluoro compounds and hexafluoroisopropyl alcohol, and terpene-based petroleum naphtha solvents and paraffinic solvents serving as high-boiling-point weak solvents for the purpose of increasing the application properties. These may be used singly or in combination of two or more kinds.

In the present invention, antibacterial agent compositions as discussed in Invention II-1 to II-7 are applied to a substrate surface thereby forming a film.

More specifically, the present invention is a substrate surface treatment method characterized by applying an antibacterial agent as discussed in any of Inventions II-1 to II-7 to a substrate surface thereby forming a film.

In addition to a polymerizable compound providing a fluorine-containing polymerizable compound (II-a) of Invention II-2, a fluorine-containing polymerizable compound (II-a-1) of Invention II-3, a fluorine-containing polymerizable compound (II-a-2) of Invention II-4 and a fluorine-containing polymerizable compound (II-a-3) of Invention II-5, it is possible to add a polymerizable compound providing a polymerizable compound (II-b-1) of general formula (II-5) or a polymerizable compound (II-b-2) of general formula (II-6), and it is also possible to add a cross-linking agent of Invention II-7.

There was prepared a multifunctional polymerizable compound having two or more polymerizable double bonds, for synthesizing a resin by using an antibacterial agent composition of Inventions II-1 to II-7. More specifically, there were prepared polymerizable compounds providing a fluorine-containing polymerizable compound (II-a) that has a bismethide acid group as discussed in Inventions II-1 to II-4, a polymerizable compound (II-b-1) of general formula (II-5) and a polymerizable compound (II-b-2) of general formula (II-6). These compounds were polymerized after being applied directly to a glass substrate with no solvent by a bar coater, spraying, spin coating or the like or after being applied to a glass substrate in the form of a solution containing these compounds by a bar coater, spraying, spin coating or the like, thereby obtaining a film that uses a colorless and transparent antibacterial agent composition of the present invention (i.e., an antibacterial film).

According to compound, it is possible to apply it directly to a substrate surface with no solvent and therefore a drying step is not necessary after polymerization, contrary to a case where a compound is made into a solution by using a solvent. It is therefore preferable to obtain a film with no solvent.

Incidentally, at the time of applying a solution, it is preferable to use as the solvent a solvent usable for polymerization. In this case, there can be employed an ester-based solvent such as ethyl acetate, n-butyl acetate and the like, a ketone-based solvent such as acetone, methyl isobutyl ketone, cyclohexanone and the like, a hydrocarbon-based solvent such as n-hexane, n-heptane and the like, an alcohol-based solvent such as methanol, isopropyl alcohol, methyl isobutyl carbinol, ethylene glycol monomethyl ether and the like, water, an ether-based solvent, a cyclic ether-based solvent, a chlorofluorocarbon-based solvent, and aromatic solvent such as toluene, xylene and the like. These solvents may be used singly or in combination of two or more kinds, as a polymerization solvent.

An initiator for radical polymerization reaction is exemplified by azo compounds, peroxide compounds and redox compounds. It is particularly preferable to use azobisisobutyronitrile, tert-butyl peroxypivalate, di-tert-butylperoxide, i-butyrylperoxide, lauroyl peroxide, succinic acid peroxide, dicinnamylperoxide, di-n-propylperoxydicarbonate, tert-butylperoxyallyl monocarbonate, benzoyl peroxide, hydrogen peroxide, and ammonium persulfate. In view of availability and good reactivity, t-butylperoxypivalate is particularly preferably used in the present invention.

In order to initiate radical polymerization reaction, a photopolymerization initiator may be used. It is preferable to use alkylphenones such as 2,2-dimethoxy-1,2-diphenylethan-1-one, 1-hydroxycyclohexyl phenyl ketone, 2-hydroxy-2-methyl-1-phenylpropan-1-one, 1-[4-(2-hydroxyethoxyl)phenyl]-2-hydroxy-2-methyl-1-propan-1-one, 2-hydroxy-1-{4-[4-(2-hydroxy-2-methylpropionyl)benzyl]phenyl}-2-methylpropan-1-one, 2-methyl-1-(4-methylphenyl)-2-morpholinopropan-1-one, 2-benzyl-2-dimethylamino-1-(4-morpholinophenyl)butanone-1,2,-(dimethylamino)-2-[(4-methylphenyl)methyl]-1-[4-(4-morpholinyl)phenyl]-1-butanone and oligo{2-hydroxy-2-methyl-[4-(1-methylvinyl) phenyl]}propanone, and acylphosphone oxides such as 2,4,6-trimethylbenzoylphenylphosphineoxide and bis(2,4,6-trimethylbenzoyl)phenylphosphineoxide. As the photopolymerization initiator, it is particularly preferable to use 1-hydroxycyclohexyl phenyl ketone in view of its availability and good reactivity.

The reaction temperature for polymerization differs according to the kind of an initiator to be used. In the case of using a thermal polymerization initiator, the temperature is preferably not lower than 50° C. and not higher than 150° C. in general, particularly preferably from 80° C. to 120° C. in terms of handling.

Meanwhile, in the case of using a photopolymerization initiator, it is possible to initiate radical polymerization on a substrate relatively low in heat resistance, such as a PET film. The substrate is irradiated with a high-pressure mercury lamp for 10 minutes under a condition of about 10 mW/cm$^2$ thereby accomplishing photo-curing. The reaction temperature for the polymerization reaction is preferably not lower than 0° C. and not higher than 100° C. in general, particularly preferably not lower than 20° C. and not higher than 50° C. in terms of handling.

A substrate which can be subjected to application is exemplified by glass, plastic, metal and the like, and more specifically electrical components, electronic appliances, building materials, craft products, apparel industrial products, medical supplies and the like.

It is possible to immerse an antibacterial resin obtained by using an antibacterial agent composition of the present invention in an aqueous solution of hydrochloric acid or sulfuric acid as necessary and then rinse it with ion exchange water.

Moreover, it is also possible to impregnate a porous film with a raw material solution that contains a fluorine-containing polymerizable compound, a polymerizable compound and a cross-linkable compound or to mix a filler such as nano-silica particles, glass fibers and the like in the raw material solution, in order to enhance the mechanical strength of an antibacterial resin using an antibacterial agent composition of the present invention.

The thickness of an antibacterial resin using an antibacterial agent composition of the present invention is not particularly limited but it is preferably not smaller than 20 nm and not larger than 1 mm. It is difficult to apply the resin to have a thickness of smaller than 20 nm, and it is not necessary to make the thickness larger than 1 mm. The film thickness is adjusted by the thickness of application to a substrate, i.e., an application quantity per unit area.

EXAMPLES

Examples for Invention "I"

In regard to the invention "I", concrete examples will be provided as follows; however, the present invention is not limited to these examples.

Of Examples of the present invention, examples using MA-ABMD as a polymerizable compound for incorporating an acrylic repeating unit (I-a-1) that has a bismethide acid group of Invention I-3 into a resin will be discussed in Resin Synthesis Examples I-1 to I-11 and Examples I-1 to I-11.

Furthermore, examples using BTSB-DMSS as a polymerizable compound for incorporating a styrene-based repeating unit (I-a-2) that has a bismethide acid group of Invention I-4 into a resin will be discussed in Synthesis Examples I-12 and I-13 and Examples I-12 and I-13.

Furthermore, examples using BTSB-NB-OH as a polymerizable compound for incorporating a norbornene-based repeating unit (I-a-3) that has a bismethide acid group of Invention I-5 into a resin will be discussed in Synthesis Examples I-14 and I-15 and Examples I-14 and I-15.

Moreover, matters obtained by Resin Synthesis Examples I-1 to I-15 were formed into resin films as discussed in Examples I-1 to I-19, and then the obtained resin films serving as specimens were subjected to an antibacterial property test by using *Escherichia coli* (NBRC3972) according to a method introduced by Japanese Industrial Standard JIS Z 2801 (2006) as "Test for antibacterial activity", thereby evaluating their antibacterial properties.

The test for antibacterial activity was conducted by using: a resin as Comparative Example I-1, obtained by reacting polyethylene glycol diacrylate with MA-EATf that has a structure including a monomethide acid group; a resin as Comparative Example I-2, obtained by reacting polyethylene glycol diacrylate with MA-3,5-HFA-CHOH that has a hexafluorocarbinol group (—(CF$_3$)$_2$OH); a resin as Comparative Example I-3, obtained by reacting polyethylene glycol diacrylate alone; and a polyethylene film as Comparative Example I-4. With this, comparisons were made with the resins containing a bismethide acid group according to the present invention (Examples I-1 to I-19) in terms of antibacterial property.

The resins used in Resin Synthesis Examples I-1 to I-19 and containing a bismethide acid group are easy to synthesize and easy to handle so as to be particularly preferably used for an antibacterial agent of the present invention.

More specifically, a resin having a repeating unit (I-a) that includes a bismethide acid group, obtained by polymerizing MA-ABMD, BTSB-DMSS or BTSB-NB-OG.

Structural formulas of MA-ABMD, BTSB-DMSS, BTSB-NB-OH, MA-EATf, MA-3,5-HFA-CHOH, BTSB-CDMS, NBOG and A-200 are shown below.

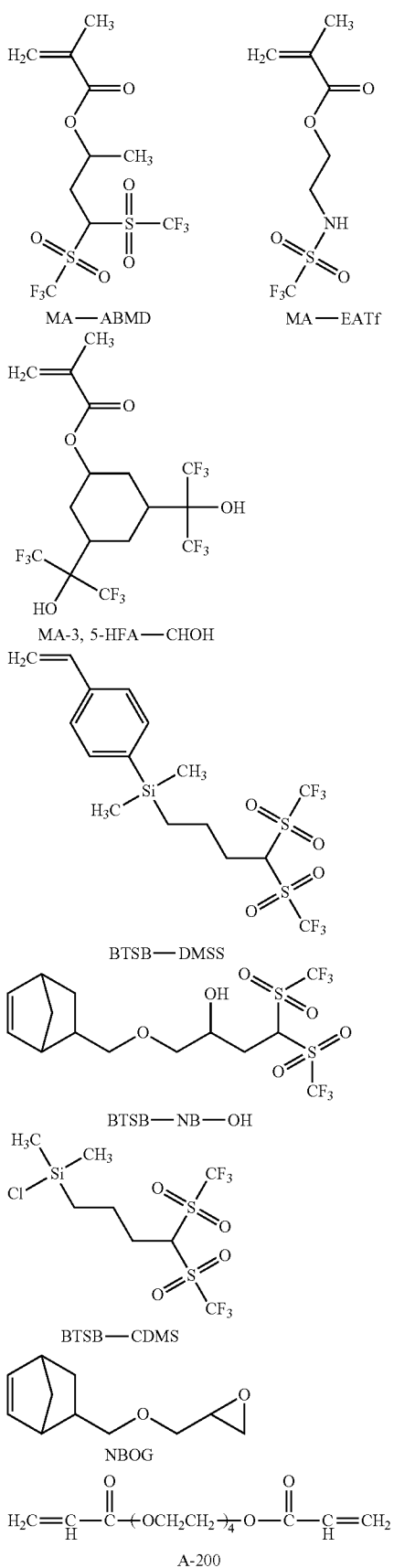

Hereinafter, there will be discussed a synthesis example of a polymerizable monomer which provides a repeating unit to be incorporated into a resin that serves as an active component of an antibacterial agent composition of the present invention.

BTSB-DMSS Synthesis Example

A 100 ml three-neck flask provided with a reflux condenser was charged with 2.08 g of magnesium and 22 ml of tetrahydrofuran under a nitrogen atmosphere, followed by stirring at 23° C. Subsequently, under a nitrogen atmosphere at the same temperature, a mixed liquid of 14.50 g of p-bromostyrene, 0.31 g of dibromoethylene and 62 ml of tetrahydrofuran was added to the three-neck flask bit by bit and dropwise during 1 hour. After the dropwise addition the liquid was stirred during 2 hours, and then 9.81 g of BTSB-CDMS was added thereto bit by bit and dropwise during 30 minutes at 23° C. After the dropwise addition, the liquid was stirred during 30 minutes and then 1 N hydrochloric acid aqueous solution and toluene were added thereto, followed by conducting a rinsing operation (which involved stirring and mixing) two times. The contents obtained after the rinsing operations were subjected to a dehydrating operation that involved azeotropic distillation with toluene, followed by the addition of 0.25 g of Nonflex MBP. Then distillation was performed under a reduced pressure of 150 Pa at 138 to 142° C. to distill 4-(4,4-bis (trifluoromethanesulfonyl)butyldimethylsilyl)styrene (hereinafter abbreviated as BTSB-DMSS) thereby obtaining 11.42 g of the same. The yield thereof was 53.9%. Incidentally, an equation of this synthesis example is as represented by Reaction Formula (I-1).

[Spectral Data of BTSB-DMSS]
$^1$H-NMR (Solvent: $CDCl_3$); δ=6.15-5.97 (m, 2H), 5.72-5.67 (m, 1H), 4.78 (t, J=8.0 Hz, 1H), 2.49-2.47 (m, 2H), 1.76-1.69 (m, 2H), 0.63 (t, J=8.0 Hz, 2H), 0.10 (s, 6H) ppm
$^{19}$F-NMR (Solvent: $CDCl_3$); δ=−73.30 ppm

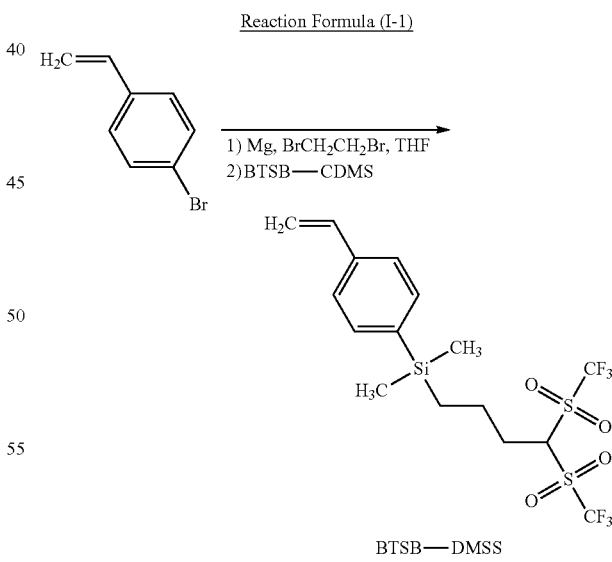

Reaction Formula (I-1)

BTSB-DMSS Synthesis Example

A 100 ml three-neck flask provided with a reflux condenser was charged with 10.06 g (0.0359 mol) of a bismethide acid and 17 ml of tetrahydrofuran under a nitrogen atmosphere, followed by stirring at 0° C. Subsequently, under a nitrogen atmosphere at the same temperature, 24 ml of methylmagnesium chloride (3 M) was added to the three-neck flask bit by bit and dropwise during 30 minutes. After the dropwise addition the liquid was stirred during 30 minutes at 23° C., and then a solution obtained by dissolving 6.46 g (0.0359 mol) of NBOG (having the above-mentioned structure) in 24 ml of tetrahydrofuran was added thereto bit by bit and dropwise during 10 minutes at the same temperature. After the dropwise addition, the liquid was stirred during 3 hours and then 1 N hydrochloric acid aqueous solution and toluene were added thereto, followed by conducting a rinsing operation (which involves stirring and mixing) two times. The contents obtained after the rinsing operations were subjected to a dehydrating operation that involves azeotropic distillation with toluene, followed by the addition of 0.25 g of Nonflex MBP. Then distillation was performed under a reduced pressure of 130 Pa at 149 to 152° C. to distill a norbornene compound (hereinafter abbreviated as BTSB-NB-OH) thereby obtaining 11.4 g of the same. The yield thereof was 68.9%. Incidentally, an equation of this synthesis example is as represented by Reaction Formula (I-2).

[Spectral Data of BTSB-NB-OH]

$^1$H-NMR (Solvent: CDCl$_3$); δ=6.15 (m, 1H), 5.92 (m, 1H), 5.57 (m, 1H), 4.04 (m, 1H), 3.63-3.59 (m, 2H), 3.27-3.23 (m, 2H), 2.58-2.52 (m, 2H), 2.36 (m, 1H), 1.82 (m, 1H), 1.58 (m, 1H), 1.50 (m, 1H), 1.27 (m, 1H), 1.14 (m, 1H), 0.51 (m, 1H) ppm 19F-NMR (Solvent: CDCl$_3$); δ=−72.80 (s, 3F), −73.80 (s, 3F) ppm

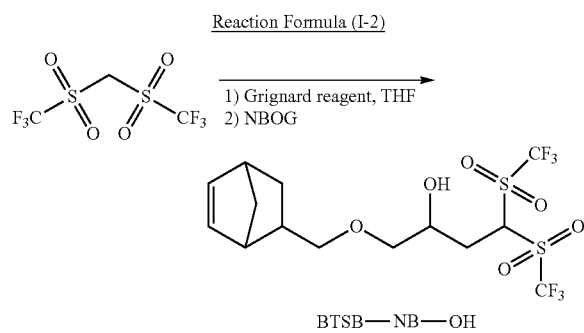

A polymerization method for a resin used in an antibacterial agent according to the present invention will hereinafter be discussed.

Resin Synthesis Example I-1

A glass flask was charged with 1.51 g (0.0037 mol) of 3-methacryloxy-1,1-bis(trifluoromethanesulfonyl)butyric acid (hereinafter abbreviated as MA-ABMD), 2.68 g (0.0088 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas.

On a glass plate, 5 ml of the solution was dropped, and applied by using a bar coater. The glass plate was put into an inert oven previously adjusted to have a temperature of 80° C. and provided with a nitrogen-introducing apparatus, and heated for 30 minutes at 80° C. The temperature was increased at a rate of 1° C. per minute and then kept at 120° C. for 60 minutes to cause curing, thereby forming a cured coating on the glass substrate.

Meanwhile, two glass plates were previously prepared and a thin glass piece (0.2 mm thickness) was inserted therebetween as a spacer, so as to form a peripheral portion defining a space. Into the space, the above-mentioned solution was poured under the favor of capillarity. It was put into an oven increased to 80° C. and kept for 30 minutes under a nitrogen atmosphere. Thereafter, the temperature was increased at a rate of 1° C. per minute and then kept at 120° C. for 60 minutes to cause curing. The glass plates were taken out of the oven to be cooled to room temperature, followed by being immersed in a water-filled vat. After a lapse of 1 hour, a resin film was peeled from the glass plates and water was wiped off with waste. The resin film was set aside at room temperature to be dried, thereby obtaining a cured independent film.

Resin Synthesis Example I-2

A glass flask was charged with 4.06 g (0.0100 mol) of MA-ABMD, 0.76 g (0.0025 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example I-1 was repeated thereby curing the solution.

Resin Synthesis Example I-3

A glass flask was charged with 0.528 g (0.0013 mol) of MA-ABMD, 3.435 g (0.0113 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example I-1 was repeated thereby curing the solution.

Resin Synthesis Example I-4

A glass flask was charged with 0.053 g (0.00013 mol) of MA-ABMD, 3.760 g (0.01237 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example I-1 was repeated thereby curing the solution.

Resin Synthesis Example I-5

A glass flask was charged with 0.053 g (0.00013 mol) of MA-ABMD, 7.864 g (0.02587 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas.

Thereafter, the procedure of Resin Synthesis Example I-1 was repeated thereby curing the solution.

Resin Synthesis Example I-6

A glass flask was charged with 0.0053 g (0.000013 mol) of MA-ABMD, 3.7960 g (0.012487 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example I-1 was repeated thereby curing the solution.

Resin Synthesis Example I-7

In a glass flask, 5.00 g (0.0123 mol) of MA-ABMD was dissolved in 10.4 g of 2-butanone and mixed. To this solution 0.057 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 240 g of n-heptane, thereby obtaining a white precipitate. The precipitate was filtered out and subjected to drying under reduced pressure at 75° C., thereby obtaining 4.08 g of a white solid.

GPC measurement results: Mw=80,100, Mw/Mn=2.77
DSC measurement results: Tg=160° C.

Resin Synthesis Example I-8

In a glass flask, 3.90 g (0.0096 mol) of MA-ABMD and 1.00 g (0.0096 mol) of styrene (produced by Tokyo Chemical Industry Co., Ltd.) were dissolved in 9.8 g of 2-butanone and mixed. To this solution 0.094 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 100 g of n-heptane, thereby obtaining a white precipitate. The precipitate was filtered out and subjected to drying under reduced pressure at 75° C., thereby obtaining 1.59 g of a white solid.

GPC measurement results: Mw=31,200, Mw/Mn=1.98
DSC measurement results: Tg=116° C.

Resin Synthesis Example I-9

In a glass flask, 2.03 g (0.0050 mol) of MA-ABMD and 0.97 g (0.0050 mol) of 2,3,4,5,6-pentafluorostyrene (produced by Tokyo Chemical Industry Co., Ltd.) were dissolved in 9.8 g of 2-butanone and mixed. To this solution 0.049 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 200 g of n-heptane, thereby obtaining a white precipitate. The precipitate was filtered out and subjected to drying under reduced pressure at 75° C., thereby obtaining 2.31 g of a white solid.

GPC measurement results: Mw=74,500, Mw/Mn=2.02
DSC measurement results: Tg=132° C.

Resin Synthesis Example I-10

In a glass flask, 1.80 g (0.0044 mol) of MA-ABMD and 0.07 g (0.0005 mol) of 2-hydroxyethyl methacrylate were dissolved in 1.4 g of 2-butanone and mixed. To this solution 0.024 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 100 g of n-heptane, thereby obtaining a white precipitate. The precipitate was filtered out and subjected to drying under reduced pressure at 75° C., thereby obtaining 1.77 g of a white solid.

GPC measurement results: Mw=429,400, Mw/Mn=4.87
DSC measurement results: Tg=148° C.

Resin Synthesis Example I-11

In a glass flask, 0.20 g (0.0005 mol) of MA-ABMD and 4.96 g (0.0495 mol) of methyl methacrylate (produced by Tokyo Chemical Industry Co., Ltd.) were dissolved in 10.3 g of 2-butanone and mixed. To this solution 0.123 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 105 g of n-heptane, thereby obtaining a white precipitate. The precipitate was filtered out and subjected to drying under reduced pressure at 75° C., thereby obtaining 4.13 g of a white solid.

GPC measurement results: Mw=36,400, Mw/Mn=1.71
DSC measurement results: Tg=123° C. [Resin Synthesis Example I-12]

In a glass flask, 5.08 g (0.0105 mol) of BTSB-DMSS was added to 2.8 g of butyl acetate and dissolved and mixed. To this solution 0.55 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 28 g of n-heptane, thereby obtaining a white precipitate. The precipitate was filtered out and subjected to drying under reduced pressure at 75° C., thereby obtaining 4.65 g of a white solid.

GPC measurement results: Mw=33,300, Mw/Mn=1.44

Resin Synthesis Example I-13

In a glass flask, 7.54 g (0.0156 mol) of BTSB-DMSS and 8.01 g (0.1511 mol) of acrylonitrile were added to 7.7 g of butyl acetate and dissolved and mixed. To this solution 0.41 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 120 g of n-heptane, thereby obtaining a white precipitate. The precipitate was filtered out and subjected to drying under reduced pressure at 75° C., thereby obtaining 14.90 g of a white solid.

GPC measurement results: Mw=500,000 or more

Resin Synthesis Example I-14

In a glass flask, 9.24 g (0.0201 mol) of BTSB-NB-OH was added to 4.4 g of toluene and dissolved and mixed. To this solution 0.141 g of dichlorobis(benzonitrile)palladium(II) and 2.15 g of boron trifluoride diethyl ether were added, and then degasification was carried out with sufficient stirring, followed by introducing thereto a nitrogen gas. Thereafter, a reaction of 4 hours was initiated at 23° C., and a solution obtained after the reaction terminated was added dropwise to 82 g of n-heptane, thereby obtaining a white precipitate. The precipitate was filtered out and subjected to drying under reduced pressure at 75° C., thereby obtaining 5.09 g of a white solid.

GPC measurement results: Mw=9,000, Mw/Mn=1.48

Resin Synthesis Example I-15

In a glass flask, 2.47 g (0.0054 mol) of BTSB-NB-OH and 4.59 g (0.0488 mol) of 2-norbornene were added to 4.4 g of toluene and dissolved and mixed. To this solution 0.200 g of dichlorobis(benzonitrile)palladium(II) and 2.05 g of boron trifluoride diethyl ether were added, and then degasification was carried out with sufficient stirring, followed by introducing thereto a nitrogen gas. Thereafter, a reaction of 4 hours was initiated at 23° C., and a solution obtained after the reaction terminated was added dropwise to 80 g of n-heptane, thereby obtaining a white precipitate. The precipitate was filtered out and subjected to drying under reduced pressure at 75° C., thereby obtaining 6.31 g of a white solid.

GPC measurement results: Mw=500,000 or more

A specimen was prepared in order to evaluate the antibacterial property of the synthesized resin. In the use of the prepared specimen, an antibacterial property test was performed according to a method of Japanese Industrial Standard JIS Z 2801 (2006) ("Test for antibacterial activity") by using *Escherichia coli* (NBRC3972). As an unprocessed specimen, a polyethylene film was employed. In Examples, there will be discussed processes for obtaining antibacterial resins from cured substances of Synthesis Examples I-1 to I-6 and from white solids of Synthesis Examples I-7 to I-15.

Example I-1

The cured substance obtained by Resin Synthesis Example I-1 was cooled to room temperature and then immersed in water, thereby obtaining a 50 mm×50 mm×0.05 mm resin film.

Example I-2

The procedure of Example I-1 was repeated thereby obtaining a resin film from the cured substance obtained by Resin Synthesis Example I-2.

Example I-3

The procedure of Example I-1 was repeated thereby obtaining a resin film from the cured substance obtained by Resin Synthesis Example I-3.

Example I-4

The procedure of Example I-1 was repeated thereby obtaining a resin film from the cured substance obtained by Resin Synthesis Example I-4.

Example I-5

The procedure of Example I-1 was repeated thereby obtaining a resin film from the cured substance obtained by Resin Synthesis Example I-5.

Example I-6

The procedure of Example I-1 was repeated thereby obtaining a resin film from the cured substance obtained by Resin Synthesis Example I-6.

Example I-7

In 3.8 g of N,N-dimethylformamide (hereinafter abbreviated as DMF), 0.2 g of the white solid obtained by Resin Synthesis Example I-7 was dissolved and mixed. This solution was applied to a glass plate and kept in an oven increased to 120° C., for 30 minutes. The temperature was increased at a rate of 1° C. per minute and kept at 160° C. for 60 minutes to cure the solution, thereby obtaining a resin film.

Example I-8

In 3.8 g of DMF, 0.2 g of the white solid obtained by Resin Synthesis Example I-8 was dissolved and mixed. The procedure of Example I-7 was repeated thereby obtaining a resin film.

Example I-9

In 3.8 g of DMF, 0.2 g of the white solid obtained by Resin Synthesis Example I-9 was dissolved and mixed. The procedure of Example I-7 was repeated thereby obtaining a resin film.

Example I-10

In 10.0 g of cyclohexanone, 1.50 g of the white solid obtained by Resin Synthesis Example I-10 was dissolved. Then, 0.33 g of pyridine and 0.10 g of hexamethylene diisocyanate were added thereto and stirred thereby obtaining a uniform solution. This solution was applied to a glass plate and provisionally dried for 1 hour at room temperature and then kept in an oven increased to 80° C., for 30 minutes. Thereafter, the temperature was increased at a rate of 1° C. per minute and kept at 130° C. for 60 minutes thereby obtaining a cured film. This film was immersed in a beaker filled with 1 L of 1 N hydrochloric acid aqueous solution at 80° C. for 1 hour and then rinsed with ion exchange water and then dried under reduced pressure at 75° C., thereby obtaining a resin film.

Example I-11

In 3.8 g of DMF, 0.2 g of the white solid obtained by Resin Synthesis Example I-11 was dissolved and mixed. The procedure of Example I-7 was repeated thereby obtaining a resin film.

Example I-12

In 3.8 g of DMF, 0.2 g of the white solid obtained by Resin Synthesis Example I-12 was dissolved and mixed. The procedure of Example I-7 was repeated thereby obtaining a resin film.

Example I-13

In 3.8 g of DMF, 0.2 g of the white solid obtained by Resin Synthesis Example I-13 was dissolved and mixed. The procedure of Example I-7 was repeated thereby obtaining a resin film.

Example I-14

In 3.8 g of DMF, 0.2 g of the white solid obtained by Resin Synthesis Example I-14 was dissolved and mixed. The procedure of Example I-7 was repeated thereby obtaining a resin film.

Example I-15

In 9.9 g of methyl isobutyl carbinol, 0.1 g of the white solid obtained by Resin Synthesis Example I-15 was dissolved and mixed. This solution was applied to a 4-inch silicon wafer substrate by spin coater and dried at 90° C. for 3 minutes thereby obtaining a cured film of 20 nm thickness.

Example I-16

A specimen having a size of 50 mm×50 mm was cut out of a resin film obtained by repeating the procedure of Example I-1, and then immersed in 200 mL of a 0.05 N sodium hydroxide aqueous solution. Upon letting it stand for 12 hours at room temperature, the film was taken out of the mixed solution and rinsed at its surface with distilled water. By virtue of sodium ions in liquid, a bismethide acid group contained in the resin film becomes an organic group having a sodium salt (a bismethide acid salt).

Example I-17

A specimen having a size of 50 mm×50 mm was cut out of a resin film obtained by repeating the procedure of Example I-2, and then immersed in 200 mL of a 0.05 N sodium hydroxide aqueous solution. Upon letting it stand for 12 hours at room temperature, the film was taken out of the mixed solution and rinsed at its surface with distilled water. By virtue of sodium ions in liquid, a bismethide acid group contained in the resin film becomes an organic group having a sodium salt (a bismethide acid salt).

Example I-18

A specimen having a size of 50 mm×50 mm was cut out of a resin film obtained by repeating the procedure of Example I-5, and then immersed in 500 mL of a 0.5 mass % silver acetate aqueous solution. Upon letting it stand for 12 hours at room temperature, the film was taken out of the mixed solution and rinsed at its surface with distilled water. By virtue of silver ions in liquid, a bismethide acid group contained in the resin film becomes an organic group having a silver salt (a bismethide acid salt).

Example I-19

A specimen having a size of 50 mm×50 mm was cut out of a resin film obtained by repeating the procedure of Example I-5, and then immersed in 500 mL of a 0.5 mass % imidazole aqueous solution. Upon letting it stand for 12 hours at room temperature, the film was taken out of the mixed solution and rinsed at its surface with distilled water. A bismethide acid group contained in the resin film becomes an organic group having an imidazolium salt (a bismethide acid salt).

Comparative Example I-1

A glass flask was charged with 0.97 g (0.0037 mol) of MA-EATf that has the above-mentioned structure (i.e., a structure including a monomethide acid group), 3.40 g (0.0088 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Example I-1 was repeated to cure the solution thereby obtaining a resin film.

Comparative Example I-21

A glass flask was charged with 1.85 g (0.0037 mol) of MA-3,5-HFA-CHOH that has the above-mentioned structure (i.e., a structure including a hexafluorocarbinol group ($—(CF_3)_2OH$)), 2.68 g (0.0088 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Example I-1 was repeated to cure the solution thereby obtaining a resin film.

Comparative Example I-31

A glass flask was charged with 3.80 g (0.0125 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Example I-1 was repeated to cure the solution thereby obtaining a resin film.

Comparative Example I-4

A polyethylene film as an unprocessed specimen.

Comparative Example I-5

A Nafion 117 film as a specimen for comparison. Incidentally, Nafion (trade name) is a perfluorocarbon material developed by American Chemical Company DuPont, including: hydrophobic skeleton consisting of carbon and fluorine; and a perfluoro side chain having a sulfonic acid group. It was used for comparison with an antibacterial agent containing a perfluorobismethide acid group according to the present invention.

[Evaluation of Antibacterial Property]

In order to evaluate the antibacterial property of the synthesized resin films, a 50 mm×50 mm specimen was cut out of each of the resin films formed of a resin having a bismethide acid group (Examples I-1 to I-19), the resin films not having a bismethide acid group (Comparative Examples I-1 to I-3 and I-5) and the resin film of 0.2 mm thickness formed of a polyethylene film as an unprocessed specimen (Comparative Example I-4), on which a test for antibacterial property was conducted according to a method of Japanese Industrial Standard JIS Z 2801 (2006) ("Test for antibacterial activity") by using *Escherichia coli* (NBRC3972). The results are shown in Table I-1.

"Amount of Methides" as shown in Table I-1 means a molar ratio of Monomer I-1 to the sum of a polymerizable compound having a bismethide acid group (Monomer I-1) and a polymerizable compound not having a bismethide acid group (Monomer I-2). Additionally, "Decrease Ratio of Bacteria" is calculated from the following equation. An antibacterial activity value is the logarithm of a number obtained by dividing the number of fungi (B) of an unprocessed specimen that has undergone a cultivation of 24 hours by the number of fungi (C) of an antibacterial-processed specimen that has undergone a cultivation of 24 hours, and is defined as bringing about the effect when the antibacterial activity value is not smaller than 2.0 (i.e., when the decrease ratio of bacteria is not smaller than 99%).

$$\text{Decrease Ratio of Bacteria } [\%] = 100\left(1 - \frac{1}{10^R}\right)$$

$R$: Antibacterial Activity Value

As shown in Table I-1, it was confirmed that an antibacterial member provided to have a surface coated with an antibacterial agent including a bismethide acid group and obtained by Examples I-1 to I-19 exhibited an excellent antibacterial activity. As compared with this, an antibacterial member provided not to have a bismethide acid group did not exhibit the antibacterial activity.

[Evaluation of Antifungal Property]

In order to evaluate the antifugal property of the synthesized resin films, a 40 mm×40 mm specimen was cut out of each of the resin films formed of a resin having a bismethide acid group (Examples I-1, I-3, I-4 and I-6), the polyethylene film as an unprocessed specimen (Comparative Example I-4) and the resin film of the Nafion 117 film (Comparative Example I-5).

A method for test was performed according to Japanese Industrial Standard JIS Z 2911 (2000) ("Methods of test for fungus resistance" with annex 1 (Test on plastic products)), in the use of a mixture of designated five kinds of strains as shown in Table I-2.

TABLE I-2

| No. | Kind of Fungas |
|---|---|
| 1 | *Aspergillus niger* (NBRC105649) |
| 2 | *Penicillium pinophilum* (NBRC33285) |
| 3 | *Paecilomyces variotii* (NBRC33284) |
| 4 | *Trichoderma virens* (NBRC6355) |
| 5 | *Chaetomium glabosum* (NBRC6347) |

TABLE I-1

| | Monomer I-1 | Monomer I-2 | Amount of Methides (%) | Decrease Ratio of Bacteria (%) |
|---|---|---|---|---|
| Example I-1 | MA-ABMD | A-200 | 30 | >99.9999 |
| Example I-2 | MA-ABMD | A-200 | 80 | >99.9999 |
| Example I-3 | MA-ABMD | A-200 | 10 | >99.9999 |
| Example I-4 | MA-ABMD | A-200 | 1 | >99.9999 |
| Example I-5 | MA-ABMD | A-200 | 0.5 | >99.9999 |
| Example I-6 | MA-ABMD | A-200 | 0.1 | 93.4 |
| Example I-7 | MA-ABMD | — | 100 | >99.9999 |
| Example I-8 | MA-ABMD | Styrene | 50 | >99.9999 |
| Example I-9 | MA-ABMD | Pentafluorostyrene | 50 | >99.9999 |
| Example I-10 | MA-ABMD | 2-Hydroxyethyl Methacrylate Hexamethylene Diisocyanate | 78 | >99.9999 |
| Example I-11 | MA-ABMD | Methyl Methacrylate | 1 | >99.9999 |
| Example I-12 | BTSB-DMSS | — | 100 | >99.9999 |
| Example I-13 | BTSB-DMSS | Acrylonitrile | 10 | >99.9999 |
| Example I-14 | BTSB-NB-OH | — | 100 | >99.9999 |
| Example I-15 | BTSB-NB-OH | 2-Norbornene | 10 | >99.9999 |
| Example I-16 | MA-ABMD | A-200 | 30 (Na Salt) | 68.4 |
| Example I-17 | MA-ABMD | A-200 | 80 (Na Salt) | 99.96 |
| Example I-18 | MA-ABMD | A-200 | 0.5 (Ag Salt) | >99.9999 |
| Example I-19 | MA-ABMD | A-200 | 0.5 (Imidazolium Salt) | >99.9999 |
| Comparative Example I-1 | MA-EATf | A-200 | — | 0 |
| Comparative Example I-2 | MA-3,5-HFA-CHOH | A-200 | — | 0 |
| Comparative Example I-3 | — | A-200 | — | 0 |
| Comparative Example I-4 | Polyethylene Film (Unprocessed Specimen) | | — | 0 |
| Comparative Example I-5 | Nafion 117 Film (Unprocessed Specimen) | | — | >99.9999 |

Criteria for evaluation in this test are as shown in Table I-3.

TABLE I-3

| Evaluation Result | Growth of Hypha |
|---|---|
| 0 | Growth of fungi was not observed by unaided eye and microscope. |
| 1 | Growth of fungi was not observed by unaided eye but observed by microscope. |
| 2 | Growth of hypha was observed by unaided eye but the hypha-growing area was not larger than 25% of the whole area of the specimen |
| 3 | Growth of hypha was observed by unaided eye and the hypha-growing area was larger than 25% of the whole area of the specimen |

The test results are as shown by Table I-4. It was confirmed that the films of Examples I-1, I-3, I-4 and I-6 exhibited an antifungal property while the films of Comparative Examples I-4 and I-5 did not exhibit an antifungal property.

TABLE I-4

| Polymer Film | Amount of Bismethide Acid Groups (mol %) | Judgement of Evaluation Results |
|---|---|---|
| Example I-1 | 30 | 0 |
| Example I-3 | 10 | 1 |
| Example I-4 | 1 | 1 |
| Example I-6 | 0.1 | 2 |
| Comparative Example I-4 | — | 2-3 |
| Comparative Example I-5 | — | 3 |

[Evaluation of Antiviral Property]

In order to evaluate the antiviral property of the synthesized resin films, a 50 mm×50 mm specimen was cut out of each of the resin films formed of a resin having a bismethide acid group (Examples I-3 and I-4) and the resin film of 0.2 mm thickness formed of a polyethylene film as an unprocessed specimen (Comparative Example I-4).

As viruses for evaluation, Influenzavirus A having an envelope and feline calicivirus having no envelope were employed.

A test was conducted in such a manner as to drop 200 mL of a virus liquid on a specimen and then place a 40 mm×40 mm polypropylene film thereon to enhance the contacting efficiency between the specimen and the virus.

After a lapse of 2 hours, the virus was recovered from the virus liquid that had been brought into contact with the specimen, thereby terminating the reaction. This liquid was diluted 10 times. A cell for viral infectivity measurement was infected with an undiluted solution or the diluted solution of the reaction-terminated liquid, thereby observing the cytopathic effect to be caused by multiplication of virus.

As a result, the resin films of Examples I-3 and I-4 had a high antiviral property against Influenzavirus A and feline calicivirus, and the cytopathic effect was not observed at all not only in the diluted solution but also in the undiluted solution of the reaction-terminated liquid.

Concerning the polyethylene film examined by the same method, the cytopathic effect was exhibited on Influenzavirus A by using the reaction-terminated liquid undiluted or diluted up to $10^5$ times, while it was not exhibited by using the reaction-terminated liquid diluted at least $10^6$ times. On feline calicivirus, the cytopathic effect was exhibited by using the reaction-terminated liquid undiluted or diluted up to $10^4$ times, while it was not exhibited at a dilution ratio of not lower than $10^5$ times.

Furthermore, the Nafion 117 film (Comparative Example I-5) was examined by the same method. As a result, the ratio of living cells of Influenzavirus A was not higher than 80% by using an undiluted eluate, so that the cytotoxicity was observed. Meanwhile, in the case of diluting the eluate 10 times or more, the cytotoxicity was not observed and therefore the antiviral property was exhibited. Feline calicivirus did not exhibit the cytotoxicity and the antiviral property was exhibited by using an undiluted eluate.

The Nafion 117 film exhibited an antiviral property, but it had cytotoxicity and therefore confirmed not to have an antifungal property.

Examples for Invention "II"

In regard to the invention "II", concrete examples will be provided as follows; however, the present invention is not limited to these examples.

Of Examples of the present invention, examples using MA-ABMD as an acrylic fluorine-containing polymerizable compound (II-a-1) that has a bismethide acid group of Invention II-2 will be discussed in Resin Synthesis Examples II-1 to II-11 and Examples II-1 to II-11.

Furthermore, examples using BTSB-DMSS as a styrene-based fluorine-containing polymerizable compound (II-a-2) that has a bismethide acid group of Invention II-3 will be discussed in Synthesis Examples II-12 and II-13 and Examples II-12 and II-13.

Furthermore, examples using BTSB-NB-OH as a norbornene-based fluorine-containing polymerizable compound (II-a-3) that has a bismethide acid group of Invention II-4 will be discussed in Synthesis Examples II-14 and II-15 and Examples II-14 and II-15.

Moreover, matters obtained by Resin Synthesis Examples II-1 to II-15 were formed into resin films as discussed in Examples II-1 to II-19, and then the obtained resin films serving as specimens were subjected to an antibacterial property test by using *Escherichia coli* (NBRC3972) according to a method introduced by Japanese Industrial Standard JIS Z 2801 (2006) as "Test for antibacterial activity", thereby evaluating their antibacterial properties.

The test for antibacterial activity was conducted by using: a resin as Comparative Example II-1, obtained by reacting polyethylene glycol diacrylate with MA-EATf that has a structure including a monomethide acid group; a resin as Comparative Example II-2, obtained by reacting polyethylene glycol diacrylate with MA-3,5-HFA-CHOH that has a hexafluorocarbinol group ($-(CF_3)_2OH$); a resin as Comparative Example II-3, obtained by reacting polyethylene glycol diacrylate alone; and a polyethylene film as Comparative Example II-4. With this, comparisons were made with the resins containing a bismethide acid group according to the present invention (Examples II-1 to II-15) in terms of antibacterial property.

The resins used in Resin Synthesis Examples II-1 to II-15 and containing a bismethide acid group are easy to synthesize and easy to handle so as to be particularly preferably used for an antibacterial agent of the present invention.

More specifically, a resin having a fluorine-containing polymerizable compound (II-a) that includes a bismethide acid group, obtained by polymerizing MA-ABMD, BTSB-DMSS or BTSB-NB-OG.

Structural formulas of MA-ABMD, BTSB-DMSS, BTSB-NB-OH, MA-EATf, MA-3,5-HFA-CHOH, BTSB-CDMS, NBOG and A-200 are shown below.

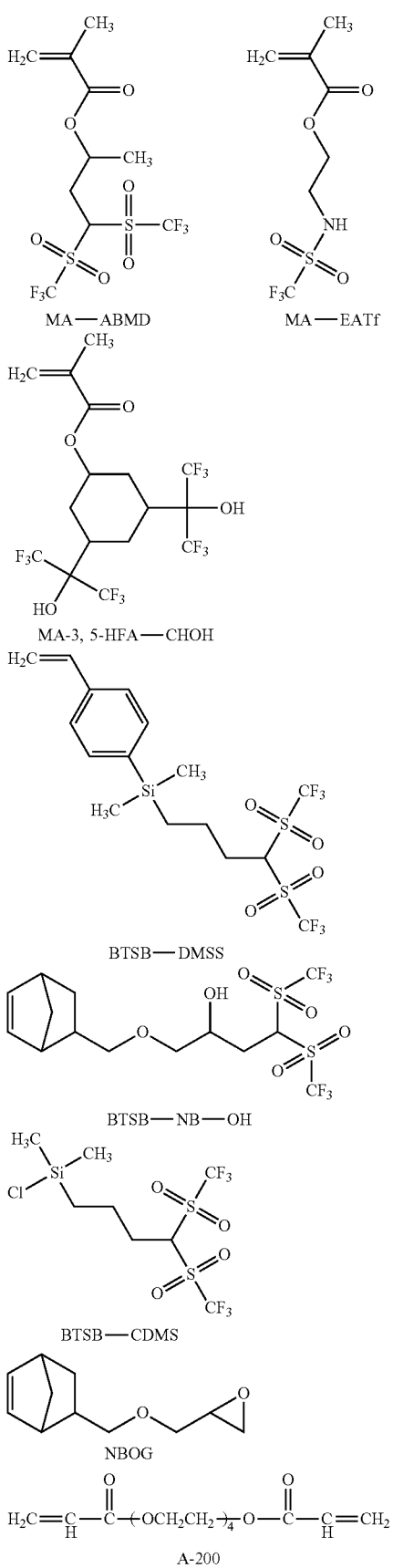

Hereinafter, there will be discussed a synthesis example of a fluorine-containing polymerizable compound to be incorporated into an antibacterial agent composition of the present invention.

BTSB-DMSS Synthesis Example

A 100 ml three-neck flask provided with a reflux condenser was charged with 2.08 g of magnesium and 22 ml of tetrahydrofuran under a nitrogen atmosphere, followed by stirring at 23° C. Subsequently, under a nitrogen atmosphere at the same temperature, a mixed liquid of 14.50 g of p-bromostyrene, 0.31 g of dibromoethylene and 62 ml of tetrahydrofuran was added to the three-neck flask bit by bit and dropwise during 1 hour. After the dropwise addition the liquid was stirred during 2 hours, and then 9.81 g of BTSB-CDMS was added thereto bit by bit and dropwise during 30 minutes at 23° C. After the dropwise addition, the liquid was stirred during 30 minutes and then 1 N hydrochloric acid aqueous solution and toluene were added thereto, followed by conducting a rinsing operation (which involved stirring and mixing) two times. The contents obtained after the rinsing operations were subjected to a dehydrating operation that involved azeotropic distillation with toluene, followed by the addition of 0.25 g of Nonflex MBP. Then distillation was performed under a reduced pressure of 150 Pa at 138 to 142° C. to distill 4-(4,4-bis (trifluoromethanesulfonyl)butyldimethylsilyl)styrene (hereinafter abbreviated as BTSB-DMSS) thereby obtaining 11.42 g of the same. The yield thereof was 53.9%. Incidentally, an equation is as represented by Reaction Formula (II-1).

[Spectral Data of BTSB-DMSS]
$^1$H-NMR (Solvent: CDCl$_3$); δ=6.15-5.97 (m, 2H), 5.72-5.67 (m, 1H), 4.78 (t, J=8.0 Hz, 1H), 2.49-2.47 (m, 2H), 1.76-1.69 (m, 2H), 0.63 (t, J=8.0 Hz, 2H), 0.10 (s, 6H) ppm
$^{19}$F-NMR (Solvent: CDCl$_3$); δ=−73.30 ppm

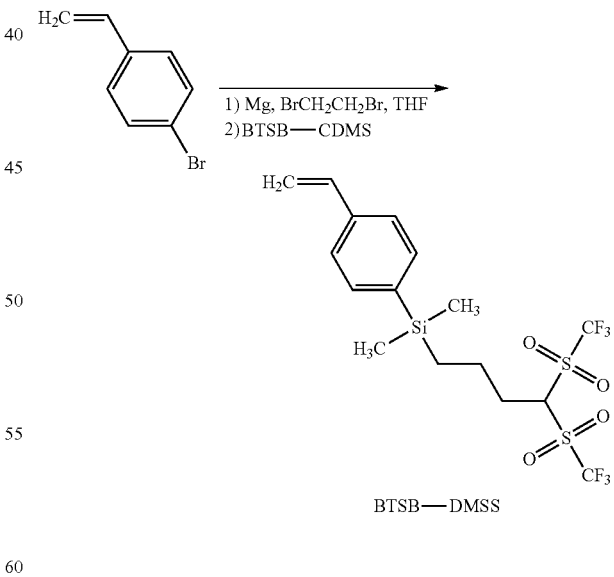

Reaction Formula (II-1)

BTSB-DMSS Synthesis Example

A 100 ml three-neck flask provided with a reflux condenser was charged with 10.06 g (0.0359 mol) of a bismethide acid and 17 ml of tetrahydrofuran under a nitrogen atmosphere, followed by stirring at 0° C. Subsequently, under a nitrogen atmosphere at the same temperature, 24 ml of methylmagnesium chloride (3 M) was added to the three-neck flask bit by bit and dropwise during 30 minutes. After the dropwise addition the liquid was stirred during 30 minutes at 23° C., and then a solution obtained by dissolving 6.46 g (0.0359 mol) of NBOG (having the above-mentioned structure) in 24 ml of tetrahydrofuran was added thereto bit by bit and dropwise during 10 minutes at the same temperature. After the dropwise addition, the liquid was stirred during 3 hours and then 1 N hydrochloric acid aqueous solution and toluene were added thereto, followed by conducting a rinsing operation (which involves stirring and mixing) two times. The contents obtained after the rinsing operations were subjected to a dehydrating operation that involves azeotropic distillation with toluene, followed by the addition of 0.25 g of Nonflex MBP. Then distillation was performed under a reduced pressure of 130 Pa at 149 to 152° C. to distill a norbornene compound (hereinafter abbreviated as BTSB-NB-OH) thereby obtaining 11.4 g of the same. The yield thereof was 68.9%. Incidentally, an equation is as represented by Reaction Formula (II-2).

[Spectral Data of BTSB-NB-OH]

$^1$H-NMR (Solvent: CDCl$_3$); δ=6.15 (m, 1H), 5.92 (m, 1H), 5.57 (m, 1H), 4.04 (m, 1H), 3.63-3.59 (m, 2H), 3.27-3.23 (m, 2H), 2.58-2.52 (m, 2H), 2.36 (m, 1H), 1.82 (m, 1H), 1.58 (m, 1H), 1.50 (m, 1H), 1.27 (m, 1H), 1.14 (m, 1H), 0.51 (m, 1H) ppm 19F-NMR (Solvent: CDCl$_3$); δ=−72.80 (s, 3F), −73.80 (s, 3F) ppm Reaction Formula (II-2)

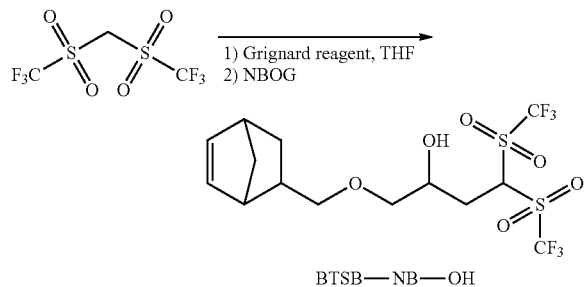

BTSB—NB—OH

A polymerization method for a resin using an antibacterial agent composition of the present invention will hereinafter be discussed.

Resin Synthesis Example II-1

A glass flask was charged with 1.51 g (0.0037 mol) of 3-methacryloxy-1,1-bis(trifluoromethanesulfonyl)butyric acid (hereinafter abbreviated as MA-ABMD), 2.68 g (0.0088 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas.

On a glass plate, 5 ml of the solution was dropped, and applied by using a bar coater. The glass plate was put into an inert oven previously adjusted to have a temperature of 80° C. and provided with a nitrogen-introducing apparatus, and heated for 30 minutes at 80° C. The temperature was increased at a rate of 1° C. per minute and then kept at 120° C. for 60 minutes to cause curing, thereby forming a cured coating on the glass substrate.

Meanwhile, two glass plates were previously prepared and a thin glass piece (0.2 mm thickness) was inserted therebetween as a spacer, so as to form a peripheral portion defining a space. Into the space, the above-mentioned solution was poured under the favor of capillarity. It was put into an oven increased to 80° C. and kept for 30 minutes under a nitrogen atmosphere. Thereafter, the temperature was increased at a rate of 1° C. per minute and then kept at 120° C. for 60 minutes to cause curing. The glass plates were taken out of the oven to be cooled to room temperature, followed by being immersed in a water-filled vat. After a lapse of 1 hour, a resin film was peeled from the glass plates and water was wiped off with waste. The resin film was set aside at room temperature to be dried, thereby obtaining a cured independent film.

Resin Synthesis Example II-2

A glass flask was charged with 4.06 g (0.0100 mol) of MA-ABMD, 0.76 g (0.0025 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example II-1 was repeated thereby curing the solution.

Resin Synthesis Example II-3

A glass flask was charged with 0.528 g (0.0013 mol) of MA-ABMD, 3.435 g (0.0113 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example II-1 was repeated thereby curing the solution.

Resin Synthesis Example II-4

A glass flask was charged with 0.053 g (0.00013 mol) of MA-ABMD, 3.760 g (0.01237 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example II-1 was repeated thereby curing the solution.

Resin Synthesis Example II-5

A glass flask was charged with 0.053 g (0.00013 mol) of MA-ABMD, 7.864 g (0.02587 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example II-1 was repeated thereby curing the solution.

Resin Synthesis Example II-6

A glass flask was charged with 0.0053 g (0.000013 mol) of MA-ABMD, 3.7960 g (0.012487 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Resin Synthesis Example II-1 was repeated thereby curing the solution.

Resin Synthesis Example II-7

In a glass flask, 5.00 g (0.0123 mol) of MA-ABMD was dissolved in 10.4 g of 2-butanone and mixed. To this solution 0.057 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 240 g of n-heptane, thereby obtaining a white precipitate. The precipitate was filtered out and subjected to drying under reduced pressure at 75° C., thereby obtaining 4.08 g of a white solid.
GPC measurement results: Mw=80,100, Mw/Mn=2.77
DSC measurement results: Tg=160° C.

Resin Synthesis Example II-8

In a glass flask, 3.90 g (0.0096 mol) of MA-ABMD and 1.00 g (0.0096 mol) of styrene (produced by Tokyo Chemical Industry Co., Ltd.) were dissolved in 9.8 g of 2-butanone and mixed. To this solution 0.094 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 100 g of n-heptane, thereby obtaining a white precipitate. The precipitate was filtered out and subjected to drying under reduced pressure at 75° C., thereby obtaining 1.59 g of a white solid.
GPC measurement results: Mw=31,200, Mw/Mn=1.98
DSC measurement results: Tg=116° C.

Resin Synthesis Example II-9

In a glass flask, 2.03 g (0.0050 mol) of MA-ABMD and 0.97 g (0.0050 mol) of 2,3,4,5,6-pentafluorostyrene (produced by Tokyo Chemical Industry Co., Ltd.) were dissolved in 9.8 g of 2-butanone and mixed. To this solution 0.049 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 200 g of n-heptane, thereby obtaining a white precipitate. The precipitate was filtered out and subjected to drying under reduced pressure at 75° C., thereby obtaining 2.31 g of a white solid.
GPC measurement results: Mw=74,500, Mw/Mn=2.02
DSC measurement results: Tg=132° C.

Resin Synthesis Example II-10

In a glass flask, 1.80 g (0.0044 mol) of MA-ABMD and 0.07 g (0.0005 mol) of 2-hydroxyethyl methacrylate were dissolved in 1.4 g of 2-butanone and mixed. To this solution 0.024 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 100 g of n-heptane, thereby obtaining a white precipitate. The precipitate was filtered out and subjected to drying under reduced pressure at 75° C., thereby obtaining 1.77 g of a white solid.
GPC measurement results: Mw=429,400, Mw/Mn=4.87
DSC measurement results: Tg=148° C.

Resin Synthesis Example II-11

In a glass flask, 0.20 g (0.0005 mol) of MA-ABMD and 4.96 g (0.0495 mol) of methyl methacrylate (produced by Tokyo Chemical Industry Co., Ltd.) were dissolved in 10.3 g of 2-butanone and mixed. To this solution 0.123 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 105 g of n-heptane, thereby obtaining a white precipitate. The precipitate was filtered out and subjected to drying under reduced pressure at 75° C., thereby obtaining 4.13 g of a white solid.
GPC measurement results: Mw=36,400, Mw/Mn=1.71
DSC measurement results: Tg=123° C.

Resin Synthesis Example II-12

In a glass flask, 5.08 g (0.0105 mol) of BTSB-DMSS was added to 2.8 g of butyl acetate and dissolved and mixed. To this solution 0.55 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 28 g of n-heptane, thereby obtaining a white precipitate.
The precipitate was filtered out and subjected to drying under reduced pressure at 75° C., thereby obtaining 4.65 g of a white solid.
GPC measurement results: Mw=33,300, Mw/Mn=1.44

Resin Synthesis Example II-13

In a glass flask, 7.54 g (0.0156 mol) of BTSB-DMSS and 8.01 g (0.1511 mol) of acrylonitrile were added to 7.7 g of butyl acetate and dissolved and mixed. To this solution 0.41 g of tert-butyl peroxypivalate (available from NOF CORPORATION under the trade name of "PERBUTYL PV") as a polymerization initiator was added, and then degasification was carried out with sufficient stirring, followed by introducing thereto a nitrogen gas. Thereafter, a reaction of 16 hours was initiated at 70° C., and a solution obtained after the reaction terminated was added dropwise to 120 g of n-heptane, thereby obtaining a white precipitate. The precipitate was filtered out and subjected to drying under reduced pressure at 75° C., thereby obtaining 14.90 g of a white solid.

GPC measurement results: Mw=500,000 or more

Resin Synthesis Example II-14

In a glass flask, 9.24 g (0.0201 mol) of BTSB-NB-OH was added to 4.4 g of toluene and dissolved and mixed. To this solution 0.141 g of dichlorobis(benzonitrile)palladium(II) and 2.15 g of boron trifluoride diethyl ether were added, and then degasification was carried out with sufficient stirring, followed by introducing thereto a nitrogen gas. Thereafter, a reaction of 4 hours was initiated at 23° C., and a solution obtained after the reaction terminated was added dropwise to 82 g of n-heptane, thereby obtaining a white precipitate. The precipitate was filtered out and subjected to drying under reduced pressure at 75° C., thereby obtaining 5.09 g of a white solid.

GPC measurement results: Mw=9,000, Mw/Mn=1.48

Resin Synthesis Example II-15

In a glass flask, 2.47 g (0.0054 mol) of BTSB-NB-OH and 4.59 g (0.0488 mol) of 2-norbornene were added to 4.4 g of toluene and dissolved and mixed. To this solution 0.200 g of dichlorobis(benzonitrile)palladium(II) and 2.05 g of boron trifluoride diethyl ether were added, and then degasification was carried out with sufficient stirring, followed by introducing thereto a nitrogen gas. Thereafter, a reaction of 4 hours was initiated at 23° C., and a solution obtained after the reaction terminated was added dropwise to 80 g of n-heptane, thereby obtaining a white precipitate. The precipitate was filtered out and subjected to drying under reduced pressure at 75° C., thereby obtaining 6.31 g of a white solid.

GPC measurement results: Mw=500,000 or more

A specimen was prepared in order to evaluate the antibacterial property of the resin synthesized by using an antibacterial agent composition of the present invention. In the use of the prepared specimen, an antibacterial property test was performed according to a method of Japanese Industrial Standard JIS Z 2801 (2006) ("Test for antibacterial activity") by using *Escherichia coli* (NBRC3972). As an unprocessed specimen, a polyethylene film was employed. In Examples, there will be discussed processes for obtaining antibacterial resins from cured substances of the above-mentioned Resin Synthesis Examples II-1 to II-6 and from white solids of Synthesis Examples II-7 to II-15.

Example II-1

The cured substance obtained by Resin Synthesis Example II-1 was cooled to room temperature and then immersed in water, thereby obtaining a 50 mm×50 mm×0.05 mm resin film.

Example II-2

The procedure of Example II-1 was repeated thereby obtaining a resin film from the cured substance obtained by Resin Synthesis Example II-2.

Example II-3

The procedure of Example II-1 was repeated thereby obtaining a resin film from the cured substance obtained by Resin Synthesis Example II-3.

Example II-4

The procedure of Example II-1 was repeated thereby obtaining a resin film from the cured substance obtained by Resin Synthesis Example II-4.

Example II-5

The procedure of Example II-1 was repeated thereby obtaining a resin film from the cured substance obtained by Resin Synthesis Example II-5.

Example II-6

The procedure of Example II-1 was repeated thereby obtaining a resin film from the cured substance obtained by Resin Synthesis Example II-6.

Example II-7

In 3.8 g of N,N-dimethylformamide (hereinafter abbreviated as DMF), 0.2 g of the white solid obtained by Resin Synthesis Example II-7 was dissolved and mixed. This solution was applied to a glass plate and kept in an oven increased to 120° C., for 30 minutes. The temperature was increased at a rate of 1° C. per minute and kept at 160° C. for 60 minutes to cure the solution, thereby obtaining a resin film.

Example II-8

In 3.8 g of DMF, 0.2 g of the white solid obtained by Resin Synthesis Example II-8 was dissolved and mixed. The procedure of Example II-7 was repeated thereby obtaining a resin film.

Example II-9

In 3.8 g of DMF, 0.2 g of the white solid obtained by Resin Synthesis Example II-9 was dissolved and mixed. The procedure of Example II-7 was repeated thereby obtaining a resin film.

Example II-10

In 10.0 g of cyclohexanone, 1.50 g of the white solid obtained by Resin Synthesis Example II-10 was dissolved. Then, 0.33 g of pyridine and 0.10 g of hexamethylene diisocyanate were added thereto and stirred thereby obtaining a uniform solution. This solution was applied to a glass plate and provisionally dried for 1 hour at room temperature and then kept in an oven increased to 80° C., for 30 minutes. Thereafter, the temperature was increased at a rate of 1° C. per minute and kept at 130° C. for 60 minutes thereby obtaining a cured film. This film was immersed in a beaker filled with 1 L of 1 N hydrochloric acid aqueous solution at 80° C. for 1 hour and then rinsed with ion exchange water and then dried under reduced pressure at 75° C., thereby obtaining a resin film.

Example II-11

In 3.8 g of DMF, 0.2 g of the white solid obtained by Resin Synthesis Example II-11 was dissolved and mixed. The procedure of Example II-6 was repeated thereby obtaining a resin film.

Example II-12

In 3.8 g of DMF, 0.2 g of the white solid obtained by Resin Synthesis Example II-12 was dissolved and mixed. The procedure of Example II-6 was repeated thereby obtaining a resin film.

Example II-13

In 3.8 g of DMF, 0.2 g of the white solid obtained by Resin Synthesis Example II-13 was dissolved and mixed. The procedure of Example II-7 was repeated thereby obtaining a resin film.

Example II-14

In 3.8 g of DMF, 0.2 g of the white solid obtained by Resin Synthesis Example II-14 was dissolved and mixed. The procedure of Example II-7 was repeated thereby obtaining a resin film.

Example II-15

In 9.9 g of methyl isobutyl carbinol, 0.1 g of the white solid obtained by Resin Synthesis Example II-15 was dissolved and mixed. This solution was applied to a 4-inch silicon wafer substrate by spin coater and dried at 90° C. for 3 minutes thereby obtaining a cured film of 20 nm thickness.

Example II-16

A specimen having a size of 50 mm×50 mm was cut out of a resin film obtained by repeating the procedure of Example II-1, and then immersed in 200 mL of a 0.05 N sodium hydroxide aqueous solution. Upon letting it stand for 12 hours at room temperature, the film was taken out of the mixed solution and rinsed at its surface with distilled water. By virtue of sodium ions in liquid, a bismethide acid group contained in the resin film becomes an organic group having a sodium salt (a bismethide acid salt).

Example II-17

A specimen having a size of 50 mm×50 mm was cut out of a resin film obtained by repeating the procedure of Example II-2, and then immersed in a mixed solution of 200 mL of a 0.05 N sodium hydroxide aqueous solution. Upon letting it stand for 12 hours at room temperature, the film was taken out of the mixed solution and rinsed at its surface with distilled water. By virtue of sodium ions in liquid, a bismethide acid group contained in the resin film becomes an organic group having a sodium salt (a bismethide acid salt).

Example II-18

A specimen having a size of 50 mm×50 mm was cut out of a resin film obtained by repeating the procedure of Example II-5, and then immersed in 500 mL of a 0.5 weight % silver acetate aqueous solution. Upon letting it stand for 12 hours at room temperature, the film was taken out of the mixed solution and rinsed at its surface with distilled water. By virtue of silver ions in liquid, a bismethide acid group contained in the resin film becomes an organic group having a silver salt (a bismethide acid salt).

Example II-19

A specimen having a size of 50 mm×50 mm was cut out of a resin film obtained by repeating the procedure of Example II-5, and then immersed in 500 mL of a 0.5 weight % imidazole aqueous solution. Upon letting it stand for 12 hours at room temperature, the film was taken out of the mixed solution and rinsed at its surface with distilled water. A bismethide acid group contained in the resin film becomes an organic group having an imidazolium salt (a bismethide acid salt).

Comparative Example II-1

A glass flask was charged with 0.97 g (0.0037 mol) of MA-EATf that has the above-mentioned structure (i.e., a structure including a monomethide acid group), 3.40 g (0.0088 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Example II-1 was repeated to cure the solution thereby obtaining a resin film.

Comparative Example II-2

A glass flask was charged with 1.85 g (0.0037 mol) of MA-3,5-HFA-CHOH that has the above-mentioned structure (i.e., a structure including a hexafluorocarbinol group ($-(CF_3)_2OH$)), 2.68 g (0.0088 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Example II-1 was repeated to cure the solution thereby obtaining a resin film.

Comparative Example II-3

A glass flask was charged with 3.80 g (0.0125 mol) of polyethylene glycol diacrylate (available from Shin-Nakamura Chemical Co., Ltd. under the trade name of A-200) and 0.10 g of tert-butyl peroxypivalate (available from NOF CORPORATION under the trade name of "PERBUTYL PV") as a polymerization initiator, and then subjected to degasification with sufficient stirring, followed by introducing thereto a nitrogen gas. Thereafter, the procedure of Example II-1 was repeated to cure the solution thereby obtaining a resin film.

Comparative Example II-4

A polyethylene film as an unprocessed specimen.

Comparative Example II-5

The above-mentioned Nafion 117 film serving as a specimen for comparison.

[Evaluation of Antibacterial Property]

In order to evaluate the antibacterial property of the synthesized resin films, a 50 mm×50 mm specimen was cut out of each of the resin films formed of a resin having a bismethide acid group (Examples II-1 to II-18), the resin films not having a bismethide acid group (Comparative Examples II-1 to II-3 and II-5) and the resin film of 0.2 mm thickness formed of a polyethylene film as an unprocessed specimen (Comparative Example II-4), on which a test for antibacterial property was conducted according to a method of Japanese Industrial Standard JIS Z 2801 (2006) ("Test for antibacterial activity") by using *Escherichia coli* (NBRC3972). The results are shown in Table II-1.

"Amount of Methides" as shown in Table II-1 means a molar ratio of Monomer II-1 to the sum of a polymerizable compound having a bismethide acid group (Monomer II-1) and a polymerizable compound not having a bismethide acid group (Monomer II-2). Additionally, "Decrease Ratio of Bacteria" is calculated from the following equation. An antibacterial activity value is the logarithm of a number obtained by dividing the number of fungi (B) of an unprocessed specimen that has undergone a cultivation of 24 hours by the number of fungi (C) of an antibacterial-processed specimen that has undergone a cultivation of 24 hours, and is defined as bringing about the effect when the antibacterial activity value is not smaller than 2.0 (i.e., when the decrease ratio of bacteria is not smaller than 99%).

$$\text{Decrease Ratio of Bacteria } [\%] = 100\left(1 - \frac{1}{10^R}\right)$$

$R$: Antibacterial Activity Value

As shown in Table II-1, it was confirmed that an antibacterial member provided to have a surface coated with an antibacterial agent including a bismethide acid group and obtained by Examples II-1 to II-19 exhibited an excellent antibacterial activity. As compared with this, an antibacterial member provided not to have a bismethide acid group did not exhibit the antibacterial activity.

[Evaluation of Antifungal Property]

In order to evaluate the antifungal property of the synthesized resin films, a 40 mm×40 mm specimen was cut out of each of the resin films formed of a resin having a bismethide acid group (Examples II-1, II-3, II-4 and II-6), the polyethylene film as an unprocessed specimen (Comparative Example II-4) and the resin film of the Nafion 117 film (Comparative Example II-5).

A method for test was performed according to Japanese Industrial Standard JIS Z 2911 (2000) ("Methods of test for fungus resistance" with annex 1 (Test on plastic products)), in the use of a mixture of designated five kinds of strains as shown in Table II-2.

TABLE II-2

| No. | Kind of Fungas |
|---|---|
| 1 | *Aspergillus niger* (NBRC105649) |
| 2 | *Penicillium pinophilum* (NBRC33285) |
| 3 | *Paecilomyces variotii* (NBRC33284) |

TABLE II-1

| | Monomer II-1 | Monomer II-2 | Amount of Methides (%) | Decrease Ratio of Bacteria (%) |
|---|---|---|---|---|
| Example II-1 | MA-ABMD | A-200 | 30 | >99.9999 |
| Example II-2 | MA-ABMD | A-200 | 80 | >99.9999 |
| Example II-3 | MA-ABMD | A-200 | 10 | >99.9999 |
| Example II-4 | MA-ABMD | A-200 | 1 | >99.9999 |
| Example II-5 | MA-ABMD | A-200 | 0.5 | >99.9999 |
| Example II-6 | MA-ABMD | A-200 | 0.1 | 93.4 |
| Example II-7 | MA-ABMD | — | 100 | >99.9999 |
| Example II-8 | MA-ABMD | Styrene | 50 | >99.9999 |
| Example II-9 | MA-ABMD | Pentafluorostyrene | 50 | >99.9999 |
| Example II-10 | MA-ABMD | 2-Hydroxyethyl Methacrylate Hexamethylene Diisocyanate | 78 | >99.9999 |
| Example II-11 | MA-ABMD | Methyl Methacrylate | 1 | >99.9999 |
| Example II-12 | BTSB-DMSS | — | 100 | >99.9999 |
| Example II-13 | BTSB-DMSS | Acrylonitrile | 10 | >99.9999 |
| Example II-14 | BTSB-NB-OH | — | 100 | >99.9999 |
| Example II-15 | BTSB-NB-OH | 2-Norbornene | 10 | >99.9999 |
| Example II-16 | MA-ABMD | A-200 | 30 (Na Salt) | 68.4 |
| Example II-17 | MA-ABMD | A-200 | 80 (Na Salt) | 99.96 |
| Example II-18 | MA-ABMD | A-200 | 0.5 (Ag Salt) | >99.9999 |
| Example II-19 | MA-ABMD | A-200 | 0.5 (Imidazolium Salt) | >99.9999 |
| Comparative Example II-1 | MA-EATf | A-200 | — | 0 |
| Comparative Example II-2 | MA-3,5-HFA-CHOH | A-200 | — | 0 |
| Comparative Example II-3 | — | A-200 | — | 0 |
| Comparative Example II-4 | Polyethylene Film (Unprocessed Specimen) | | — | 0 |
| Comparative Example II-5 | Nafion 117 Film (Unprocessed Specimen) | | — | >99.9999 |

TABLE II-2-continued

| No. | Kind of Fungas |
|---|---|
| 4 | *Trichoderma virens* (NBRC6355) |
| 5 | *Chaetomium glabosum* (NBRC6347) |

Criteria for evaluation in this test are as shown in Table II-3.
[Table II-3]

TABLE II-3

| Evaluation Result | Growth of Hypha |
|---|---|
| 0 | Growth of fungi was not observed by unaided eye and microscope. |
| 1 | Growth of fungi was not observed by unaided eye but observed by microscope. |
| 2 | Growth of hypha was observed by unaided eye but the hypha-growing area was not larger than 25% of the whole area of the specimen |
| 3 | Growth of hypha was observed by unaided eye and the hypha-growing area was larger than 25% of the whole area of the specimen |

The test results are as shown by Table II-4. It was confirmed that the films of Examples II-1, II-3, II-4 and II-6 exhibited an antifungal property while the films of Comparative Examples II-4 and II-5 did not exhibit an antifungal property.

TABLE II-4

| Polymer Film | Amount of Bismethide Acid Groups (mol %) | Judgement of Evaluation Results |
|---|---|---|
| Example II-1 | 30 | 0 |
| Example II-3 | 10 | 1 |
| Example II-4 | 1 | 1 |
| Example II-6 | 0.1 | 2 |
| Comparative Example II-4 | — | 2-3 |
| Comparative Example II-5 | — | 3 |

[Evaluation of Antiviral Property]

In order to evaluate the antiviral property of the synthesized resin films, a 50 mm×50 mm specimen was cut out of each of the resin films formed of a resin having a bismethide acid group (Examples II-3 and II-4) and the resin film of 0.2 mm thickness formed of a polyethylene film as an unprocessed specimen (Comparative Example II-4).

As viruses for evaluation, Influenzavirus A having an envelope and feline calicivirus having no envelope were employed.

A test was conducted in such a manner as to drop 200 mL of a virus liquid on a specimen and then place a 40 mm×40 mm polypropylene film thereon to enhance the contacting efficiency between the specimen and the virus.

After a lapse of 2 hours, the virus was recovered from the virus liquid that had been brought into contact with the specimen, thereby terminating the reaction. This liquid was diluted 10 times. A cell for viral infectivity measurement was infected with an undiluted solution or the diluted solution of the reaction-terminated liquid, thereby observing the cytopathic effect to be caused by multiplication of virus.

As a result, the resin films of Examples II-3 and II-4 had a high antiviral property against Influenzavirus A and feline calicivirus, and the cytopathic effect was not observed at all not only in the diluted solution but also in the undiluted solution of the reaction-terminated liquid.

Concerning the polyethylene film examined by the same method, the cytopathic effect was exhibited on Influenzavirus A by using the reaction-terminated liquid undiluted or diluted up to $10^5$ times, while it was not exhibited by using the reaction-terminated liquid diluted at least $10^6$ times. On feline calicivirus, the cytopathic effect was exhibited by using the reaction-terminated liquid undiluted or diluted up to $10^4$ times, while it was not exhibited at a dilution ratio of not lower than $10^5$ times.

Furthermore, the Nafion 117 film (Comparative Example II-5) was examined by the same method. As a result, the ratio of living cells of Influenzavirus A was not higher than 80% by using an undiluted eluate, so that the cytotoxicity was observed. Meanwhile, in the case of diluting the eluate 10 times or more, the cytotoxicity was not observed and therefore the antiviral property was exhibited. Feline calicivirus did not exhibit the cytotoxicity and the antiviral property was exhibited by using an undiluted eluate.

The Nafion 117 film exhibited an antiviral property, but it had cytotoxicity and therefore confirmed not to have an antifungal property.

The invention claimed is:

1. A method of imparting antibacterial properties to a member, comprising the steps of:
   a) synthesizing a resin having an organic group represented by general formula (I-1)

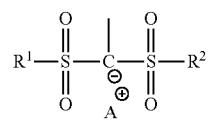

(I-1)

wherein $R^1$ and $R^2$ mutually independently represent a $C_1$-$C_4$ fluoroalkyl group,
   "C" and "A" are bonded to each other through a covalent bond or an ionic bond, and
   "A" represents a hydrogen atom or a cation; and
   b) preparing an antibacterial agent containing the resin as an active component.

2. A method as claimed in claim 1, wherein the resin comprises a repeating unit represented by general formula (I-2)

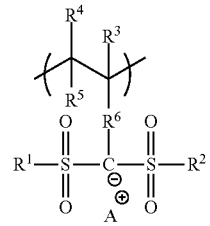

(I-2)

wherein $R^1$ and $R^2$ mutually independently represent a $C_1$-$C_4$ fluoroalkyl group;
   $R^3$ represents a hydrogen atom, a $C_1$-$C_4$ alkyl group, a halogen atom or a $C_1$-$C_4$ fluoroalkyl group;
   $R^4$ and $R^5$ mutually independently represent a hydrogen atom, a $C_1$-$C_4$ alkyl group or a halogen atom;
   $R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with a fluorine atom or a hydroxyl group;

$R^3$ and $R^4$, or $R^5$ and $R^6$ may be bonded to each other to form a ring and may contain a $C_3$-$C_{12}$ single, double or multi ring structure;

"C" and "A" are bonded to each other through a covalent bond or an ionic bond; and "A" represents a hydrogen atom or a cation.

3. A method as claimed in claim 2, wherein the repeating unit is represented by general formula (I-3)

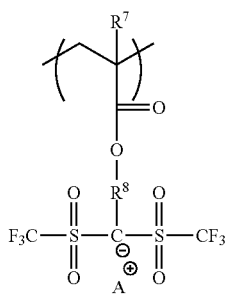

(I-3)

wherein $R^7$ represents a hydrogen atom, an alkyl group, a halogen atom or a trifluoromethyl group;

$R^8$ represents a single bond, a $C_1$-$C_{12}$ linear, branched or cyclic divalent hydrocarbon group, or a divalent hydrocarbon group having any combination of these, wherein $R^8$ may have an ether bond, an ester bond, an amide bond or an urethane bond, some carbon atoms contained in $R^8$ may be substituted with silicon, and some or all hydrogen atoms may be substituted with a fluorine atom or a hydroxyl group;

"C" and "A" are bonded to each other through a covalent bond or an ionic bond; and "A" represents a hydrogen atom or a cation.

4. A method as claimed in claim 2, wherein the repeating unit is represented by general formula (I-4)

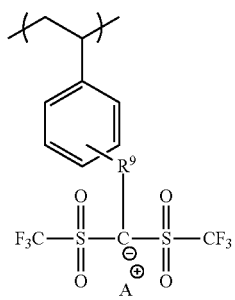

(I-4)

wherein $R^9$ represents a single bond, a $C_1$-$C_{12}$ linear, branched or cyclic divalent hydrocarbon group, or a divalent hydrocarbon group having any combination of these, wherein $R^9$ may have an ether bond, an ester bond, an amide bond or an urethane bond, some carbon atoms contained in $R^9$ may be substituted with silicon, and some or all hydrogen atoms may be substituted with a fluorine atom or a hydroxyl group;

"C" and "A" are bonded to each other through a covalent bond or an ionic bond; and "A" represents a hydrogen atom or a cation.

5. A method as claimed in claim 2, wherein the repeating unit is represented by general formula (I-5)

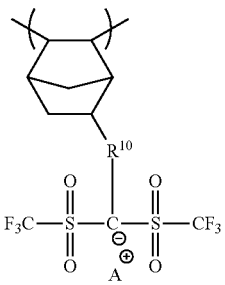

(I-5)

wherein $R^{10}$ represents a single bond, a $C_1$-$C_{12}$ linear, branched or cyclic divalent hydrocarbon group, or a divalent hydrocarbon group having any combination of these, wherein $R^{10}$ may have an ether bond, an ester bond, an amide bond or an urethane bond, some carbon atoms contained in $R^{10}$ may be substituted with silicon, and some or all hydrogen atoms may be substituted with a fluorine atom or a hydroxyl group;

"C" and "A" are bonded to each other through a covalent bond or an ionic bond; and "A" represents a hydrogen atom or a cation.

6. A method as claimed in claim 2, wherein the resin further comprises a repeating unit represented by general formula (I-6)

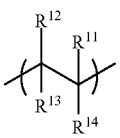

(I-6)

wherein $R^{11}$ represents a hydrogen atom, a $C_1$-$C_4$ alkyl group, a halogen atom or a $C_1$-$C_4$ fluoroalkyl group;

$R^{12}$ and $R^{13}$ mutually independently represent a hydrogen atom, a $C_1$-$C_4$ alkyl group or a halogen atom;

$R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with a fluorine atom or a hydroxyl group; and wherein $R^{11}$ and $R^{12}$, or $R^{13}$ and $R^{14}$ may be bonded to each other to form a ring and may contain a $C_3$-$C_{12}$ single, double or multi ring structure.

7. A method as claimed in claim 2, wherein the resin further comprises a repeating unit represented by general formula (I-7)

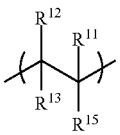

(I-7)

wherein $R^{11}$ represents a hydrogen atom, a $C_1$-$C_4$ alkyl group, a halogen atom or a $C_1$-$C_4$ fluoroalkyl group, $R^{12}$ and $R^{13}$ mutually independently represent a hydrogen atom, a $C_1$-$C_4$ alkyl group or a halogen atom;

$R^{11}$ and $R^{12}$ or $R^{13}$ may be bonded to each other to form a ring and may contain a $C_3$-$C_{12}$ single, double or multi ring structure;

$R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with a fluorine atom or a hydroxyl group, and wherein $R^{15}$ has a group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.

8. A method as claimed in claim 7, wherein
the antibacterial agent is curable,
the resin further comprises a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group, and
the resin is cross-linked by the cross-linking agent.

9. A method as claimed in claim 1, further comprising a substrate surface treatment step wherein the antibacterial agent is applied or adhered to a substrate surface, thereby forming a film.

10. A method as claimed in claim 1, further comprising a substrate surface treatment step,
wherein a film of the antibacterial agent is obtained by applying or adhering a polymerizable compound serving as a precursor of a repeating unit to a substrate surface,
wherein the polymerizable compound is represented by general formula (II-1)

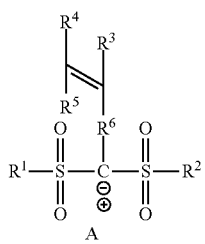

(II-1)

wherein $R^1$ and $R^2$ mutually independently represent a $C_1$-$C_4$ fluoroalkyl group;
$R^3$ represents a hydrogen atom, a $C_1$-$C_4$ alkyl group, a halogen atom or a $C_1$-$C_4$ fluoroalkyl group;
$R^4$ and $R^5$ mutually independently represent a hydrogen atom, a $C_1$-$C_4$ alkyl group or a halogen atom;
$R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with a fluorine atom or a hydroxyl group;

$R^3$ and $R^4$, or $R^5$ and $R^6$ may be bonded to each other to form a ring and may contain a $C_3$-$C_{12}$ single, double or multi ring structure;
"C" and "A" are bonded to each other through a covalent bond or an ionic bond; and
"A" represents a hydrogen atom or a cation.

11. A method as claimed in claim 10, wherein the substrate surface treatment step is conducted by adding another polymerizable compound represented by general formula (II-5)

(II-5)

or general formula (II-6)

(II-6)

to the polymerizable compound represented by general formula (II-1),

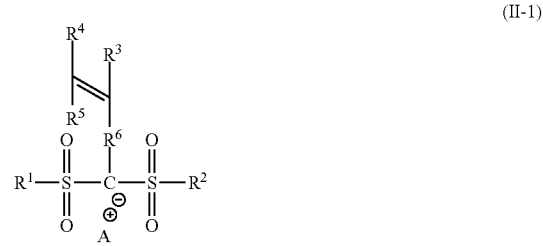

(II-1)

and then applying or attaching it to a substrate surface thereby forming a film formed of the antibacterial agent,
wherein $R^1$ and $R^2$ mutually independently represent a $C_1$-$C_4$ fluoroalkyl group;
$R^3$ represents a hydrogen atom, a $C_1$-$C_4$ alkyl group, a halogen atom or a $C_1$-$C_4$ fluoroalkyl group;
$R^4$ and $R^5$ mutually independently represent a hydrogen atom, a $C_1$-$C_4$ alkyl group or a halogen atom;
$R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with a fluorine atom or a hydroxyl group;
$R^3$ and $R^4$, or $R^5$ and $R^6$ may be bonded to each other to form a ring and may contain a $C_3$-$C_{12}$ single, double or multi ring structure;
"C" and "A" are bonded to each other through a covalent bond or an ionic bond, "A" represents a hydrogen atom or a cation;

$R^{11}$ represents a hydrogen atom, a $C_1$-$C_4$ alkyl group, a halogen atom or a $C_1$-$C_4$ fluoroalkyl group;

$R^{12}$ and $R^{13}$ mutually independently represent a hydrogen atom, a $C_1$-$C_4$ alkyl group or a halogen atom;

$R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with a fluorine atom or a hydroxyl group;

$R^{11}$ and $R^{12}$, or $R^{13}$ and $R^{14}$ may be bonded to each other to form a ring and may contain a $C_3$-$C_{12}$ single, double or multi ring structure; and $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with a fluorine atom or a hydroxyl group, and wherein $R^{15}$ has a group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.

12. A method as claimed in claim 9, wherein the antibacterial agent is formed after further adding a cross-linking agent.

13. A method as claimed in claim 12, further comprising a step of heating the film to cause polymerization or cross-linking, thereby curing the film.

14. A method as claimed in claim 12, further comprising a step of irradiating the film with light to cause polymerization or cross-linking, thereby curing the film.

15. A method for producing an antibacterial member, characterized by conducting a surface treatment according to the method as claimed in claim 9.

16. A method of imparting antibacterial properties to a member, comprising the steps of:

a) synthesizing a fluorine-containing polymerizable compound represented by general formula (II-1);

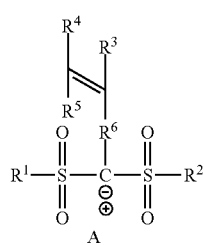

(I-2-1)

wherein $R^1$ and $R^2$ mutually independently represent a $C_1$-$C_4$ fluoroalkyl group;

$R^3$ represents a hydrogen atom, a $C_1$-$C_4$ alkyl group, a halogen atom or a $C_1$-$C_4$ fluoroalkyl group;

$R^4$ and $R^5$ mutually independently represent a hydrogen atom, a $C_1$-$C_4$ alkyl group or a halogen atom;

$R^6$ represents a single bond, a $C_1$-$C_{12}$ linear, branched or cyclic divalent hydrocarbon group, or a divalent hydrocarbon group having any combination of these, wherein $R^6$ may have an ether bond, an ester bond, an amide bond or an urethane bond, some carbon atoms contained in $R^6$ may be substituted with silicon, and some or all hydrogen atoms may be substituted with a fluorine atom or a hydroxyl group;

$R^3$ and $R^4$, or $R^5$ and $R^6$ may be bonded to each other to form a ring and may contain a $C_3$-$C_{12}$ single, double or multi ring structure;

"C" and "A" are bonded to each other through a covalent bond or an ionic bond; and "A" represents a hydrogen atom or a cation; and b) preparing an antibacterial agent composition comprising the fluorine-containing polymerizable compound.

17. A method as claimed in claim 16, wherein the antibacterial agent composition comprises a fluorine-containing polymerizable compound represented by general formula (II-2)

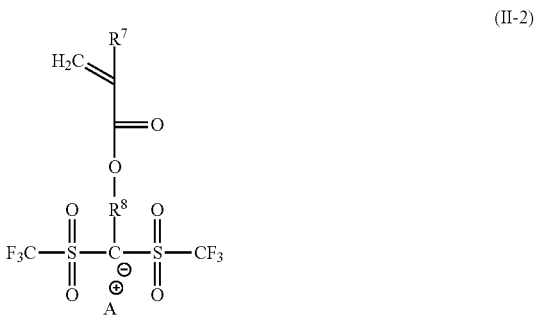

(II-2)

wherein $R^7$ represents a hydrogen atom, an alkyl group, a halogen atom or a trifluoromethyl group;

$R^8$ represents a single bond, a $C_1$-$C_{12}$ linear, branched or cyclic divalent hydrocarbon group, or a divalent hydrocarbon group having any combination of these, wherein $R^8$ may have an ether bond, an ester bond, an amide bond or an urethane bond, some carbon atoms contained in $R^8$ may be substituted with silicon, and some or all hydrogen atoms may be substituted with a fluorine atom or a hydroxyl group;

"C" and "A" are bonded to each other through a covalent bond or an ionic bond; and "A" represents a hydrogen atom or a cation.

18. A method as claimed in claim 16, wherein the antibacterial agent composition comprises a fluorine-containing polymerizable compound represented by general formula (II-3)

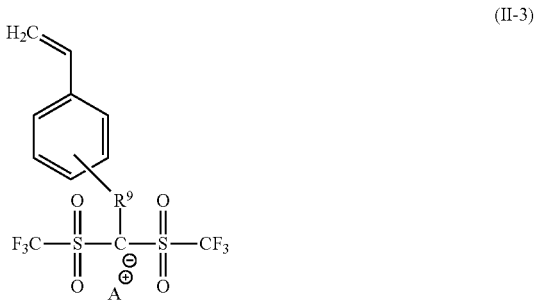

(II-3)

wherein $R^9$ represents a single bond, a $C_1$-$C_{12}$ linear branched or cyclic divalent hydrocarbon group, or a divalent hydrocarbon group having any combination of these, wherein $R^9$ may have an ether bond, an ester bond, an amide bond or an urethane bond, some carbon atoms contained in $R^9$ may be substituted with silicon, and some or all hydrogen atoms may be substituted with a fluorine atom or a hydroxyl group;

"C" and "A" are bonded to each other through a covalent bond or an ionic bond; and "A" represents a hydrogen atom or a cation.

19. A method as claimed in claim 16, wherein the antibacterial agent composition comprises a fluorine-containing polymerizable compound represented by general formula (II-4)

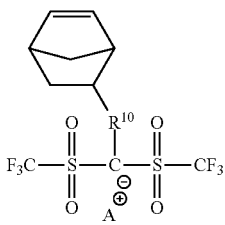

(II-4)

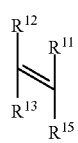

wherein $R^{10}$ represents a single bond, a $C_1$-$C_{12}$ linear, branched or cyclic divalent hydrocarbon group, or a divalent hydrocarbon group having any combination of these, wherein $R^{10}$ may have an ether bond, an ester bond, an amide bond or an urethane bond, some carbon atoms contained in $R^{10}$ may be substituted with silicon, and some or all hydrogen atoms may be substituted with a fluorine atom or a hydroxyl group;

"C" and "A" are bonded to each other through a covalent bond or an ionic bond; and "A" represents a hydrogen atom or a cation.

20. A method as claimed in claim 16, wherein the antibacterial agent composition further comprises a polymerizable compound represented by general formula (II-5)

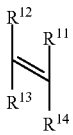

(II-5)

wherein $R^{11}$ represents a hydrogen atom, a $C_1$-$C_4$ alkyl group, a halogen atom or a $C_1$-$C_4$ fluoroalkyl group;

$R^{12}$ and $R^{13}$ mutually independently represent a hydrogen atom, a $C_1$-$C_4$ alkyl group or a halogen atom;

$R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with a fluorine atom or a hydroxyl group;

wherein $R^{11}$ and $R^{12}$, or $R^{13}$ and $R^{14}$ may be bonded to each other to form a ring and may contain a $C_3$-$C_{12}$ single, double or multi ring structure;

"C" and "A" are bonded to each other through a covalent bond or an ionic bond; and "A" represents a hydrogen atom or a cation.

21. A method as claimed in claim 16, wherein the antibacterial agent composition further comprises a polymerizable compound represented by general formula (II-6)

(II-6)

wherein $R^{11}$ represents a hydrogen atom, a $C_1$-$C_4$ alkyl group, a halogen atom or a $C_1$-$C_4$ fluoroalkyl group;

$R^{12}$ and $R^{13}$ mutually independently represent a hydrogen atom, a $C_1$-$C_4$ alkyl group or a halogen atom;

$R^{11}$ and $R^{12}$ or $R^{13}$ may be bonded to each other to form a ring and may contain a $C_3$-$C_{12}$ single, double or multi ring structure;

$R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with a fluorine atom or a hydroxyl group; and $R^{15}$ has one or more kinds of functional groups selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.

22. A method as claimed in claim 20, wherein the antibacterial agent composition further comprises a cross-linking agent having one or more kinds of groups selected from isocyanate group, hydroxyl group, mercapto group, carboxyl group, amino group, epoxy group, alkenyl group, alkynyl group, acryloyl group, methacryloyl group, chlorosilyl group, alkoxysilyl group and hydrosilyl group.

23. A method as claimed in claim 16, further comprising a step of producing an antibacterial resin by polymerization reaction or cross-linking reaction of the antibacterial agent composition.

24. A method as claimed in claim 16, further comprising a substrate surface treatment step wherein the antibacterial agent composition is applied or adhered to a substrate surface, thereby forming a film.

25. A method as claimed in claim 24, further comprising a step of adding a polymerizable compound represented by general formula (II-5)

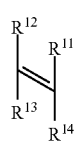

(I-6-1)

or general formula (II-6)

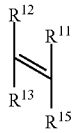
(I-7-1)

to the antibacterial agent composition before applying or adhering the antibacterial agent composition to the substrate surface, thereby forming the film;

wherein $R^{11}$ represents a hydrogen atom, a $C_1$-$C_4$ alkyl group, a halogen atom or a $C_1$-$C_4$ fluoroalkyl group;

$R^{12}$ and $R^{13}$ mutually independently represent a hydrogen atom, a $C_1$-$C_4$ alkyl group or a halogen atom;

$R^{14}$ represents a hydrogen atom, a halogen atom, a $C_1$-$C_{35}$ linear, branched or cyclic monovalent hydrocarbon group, or a monovalent hydrocarbon group having any combination of these, wherein $R^{14}$ may have an ether bond, an ester bond, an amide bond or an urethane bond, some carbon atoms contained in $R^{14}$ may be substituted with silicon, and some or all hydrogen atoms may be substituted with a fluorine atom or a hydroxyl group; and wherein $R^{11}$ and $R^{12}$, or $R^{13}$ and $R^{14}$ may be bonded to each other to form a ring and may contain a $C_3$-$C_{12}$ single, double or multi ring structure; and $R^{15}$ represents a hydrogen atom, a halogen atom, a $C_1$-$C_{35}$ linear, branched or cyclic monovalent hydrocarbon group, or a monovalent hydrocarbon group having any combination of these, wherein $R^{15}$ may have an ether bond, an ester bond, an amide bond or an urethane bond, some carbon atoms contained in $R^{15}$ may be substituted with silicon, and some or all hydrogen atoms may be substituted with a fluorine atom or a hydroxyl group, and wherein $R^{15}$ has a group reactive with a cross-linking agent, the group being selected from hydroxyl group, mercapto group, carboxyl group, amino group, epoxy group, alkenyl group, alkynyl group, acryloyl group, methacryloyl group, chlorosilyl group, alkoxysilyl group and hydrosilyl group.

26. A method as claimed in claim 24, wherein the film is formed after further adding a cross-linking agent.

27. A method as claimed in claim 26, wherein the film is heated to cause polymerization or cross-linking, thereby curing the film.

28. A method as claimed in claim 26, wherein the film is irradiated with light to cause polymerization or cross-linking, thereby curing the film.

29. A method for producing an antibacterial member, characterized by conducting a surface treatment according to the method as claimed in claim 24.

30. A method of imparting antibacterial properties to a member, comprising the steps of synthesizing a fluorine-containing polymerizable compound represented by general formula (II-7)

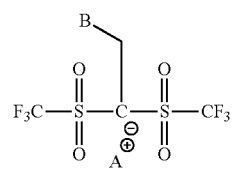
(II-7)

wherein $R^{16}$ represents a $C_1$-$C_{12}$ linear, branched or cyclic divalent hydrocarbon group, or a divalent group having any combination of these and having carbon atoms partially or entirely substituted with silicon, wherein $R^{16}$ may have an ether bond, an ester bond, an amide bond or an urethane bond, and some or all hydrogen atoms contained in $R^{16}$ may be substituted with a fluorine atom or a hydroxyl group;

"C" and "A" are bonded to each other through a covalent bond or an ionic bond;

"A" represents a hydrogen atom or a cation; and

"B" is either one of groups represented by the following structures

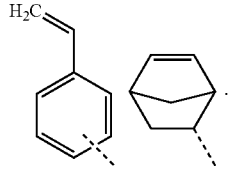

* * * * *